US009943673B2

(12) United States Patent
Kendall et al.

(10) Patent No.: US 9,943,673 B2
(45) Date of Patent: Apr. 17, 2018

(54) PATCH APPLYING APPARATUS

(75) Inventors: Mark Anthony Fernance Kendall, Chelmer (AU); Alexander Bernard Ansaldo, Indooroopilly (AU); Michael Lawrence Crichton, Auchenflower (AU); Robert John Falconer, Sheffield (GB)

(73) Assignee: VAXXAS PTY LIMITED, Sydney (AU)

( * ) Notice: Subject to any disclaimer, the term of this patent is extended or adjusted under 35 U.S.C. 154(b) by 293 days.

(21) Appl. No.: 13/810,174

(22) PCT Filed: Jul. 14, 2011

(86) PCT No.: PCT/AU2011/000890
§ 371 (c)(1),
(2), (4) Date: Apr. 9, 2013

(87) PCT Pub. No.: WO2012/006677
PCT Pub. Date: Jan. 19, 2012

(65) Prior Publication Data
US 2013/0190794 A1 Jul. 25, 2013

(30) Foreign Application Priority Data
Jul. 14, 2010 (AU) ................................ 2010903137

(51) Int. Cl.
*A61B 17/00* (2006.01)
*A61M 37/00* (2006.01)
(Continued)

(52) U.S. Cl.
CPC ..... *A61M 37/0015* (2013.01); *A61B 5/14503* (2013.01); *A61B 5/14514* (2013.01); *A61B 5/6833* (2013.01); *A61B 17/205* (2013.01)

(58) Field of Classification Search
CPC ...... A61M 37/0015; A61M 2037/0023; A61M 2037/0046; A61M 2037/0061;
(Continued)

(56) References Cited

U.S. PATENT DOCUMENTS 2,213,830 A * 9/1940 Anastasi ................ A61B 17/04
606/145
2,881,500 A * 4/1959 Furness ........................... 24/542
(Continued)

FOREIGN PATENT DOCUMENTS

CN 101214395 A 7/2008
CN 101297989 A 11/2008
(Continued)

OTHER PUBLICATIONS

International Preliminary Report on Patentability, dated Nov. 14, 2012, for International Application No. PCT/AU2011/000890, 6 pages.
(Continued)

*Primary Examiner* — Jonathan Miles
*Assistant Examiner* — Mohamed Gabr
(74) *Attorney, Agent, or Firm* — Seed IP Law Group LLP

(57) ABSTRACT

Apparatus for applying a patch to a subject, the patch having a number of projections thereon, the apparatus including opposable jaws movable between open and engaging positions, wherein in the open position the jaws can receive at least part of the subject, and in the engaging position the jaws can engage the at least part of the subject and a patch support for supporting a patch, and wherein the patch support is for urging the patch against the at least part of the subject.

21 Claims, 31 Drawing Sheets

(51) Int. Cl.
    *A61B 5/145* (2006.01)
    *A61B 5/00* (2006.01)
    *A61B 17/20* (2006.01)

(58) Field of Classification Search
    CPC ....... A61M 2005/14506; A61M 5/1454; A61L
        35/14503; A61L 35/6833; A61B 17/205;
        A61B 17/122; A61B 17/1227; A61B
        17/083; A61B 5/14503; A61B 5/6833;
        A61B 5/14514; A61B 2017/2825; A61B
        2017/2808; A61B 10/0045
    USPC ....... 606/151, 157, 158, 186, 205, 206, 207,
        606/213; 604/46, 136, 173, 506;
        623/23.72
    See application file for complete search history.

(56) References Cited

U.S. PATENT DOCUMENTS

| | | |
|---|---|---|
| 4,702,799 A | 10/1987 | Tuot |
| 5,201,992 A | 4/1993 | Marcus et al. |
| 5,353,792 A | 10/1994 | Lübbers et al. |
| 5,449,064 A | 9/1995 | Hogan et al. |
| 5,457,041 A | 10/1995 | Ginaven et al. |
| 5,499,474 A * | 3/1996 | Knooihuizen ............ 47/1.5 |
| 5,527,288 A | 6/1996 | Gross et al. |
| 5,611,806 A | 3/1997 | Jang |
| 5,859,937 A | 1/1999 | Nomura |
| 5,922,356 A | 7/1999 | Koseki et al. |
| 5,928,207 A | 7/1999 | Pisano et al. |
| 6,052,652 A | 4/2000 | Lee |
| 6,287,556 B1 | 9/2001 | Portnoy et al. |
| 6,299,621 B1 * | 10/2001 | Fogarty et al. ............ 606/151 |
| 6,334,856 B1 | 1/2002 | Allen et al. |
| 6,352,697 B1 | 3/2002 | Cox et al. |
| 6,454,755 B1 | 9/2002 | Godshall |
| 6,463,312 B1 | 10/2002 | Bergveld et al. |
| 6,478,738 B1 | 11/2002 | Hirabayashi et al. |
| 6,503,231 B1 | 1/2003 | Prausnitz et al. |
| 6,537,242 B1 | 3/2003 | Palmer |
| 6,537,264 B1 | 3/2003 | Cormier et al. |
| 6,551,849 B1 | 4/2003 | Kenney |
| 6,557,849 B2 | 5/2003 | Wyss |
| 6,558,361 B1 | 5/2003 | Yeshurun |
| 6,565,532 B1 | 5/2003 | Yuzhakov et al. |
| 6,589,202 B1 | 7/2003 | Powell |
| 6,591,124 B2 | 7/2003 | Sherman et al. |
| 6,610,382 B1 * | 8/2003 | Kobe ............ A63B 49/08 |
| | | 128/849 |
| 6,743,211 B1 | 6/2004 | Prausnitz et al. |
| 6,749,575 B2 | 6/2004 | Matriano et al. |
| 6,855,372 B2 | 2/2005 | Trautman et al. |
| 6,881,203 B2 | 4/2005 | Delmore et al. |
| 6,908,453 B2 | 6/2005 | Fleming et al. |
| 6,923,764 B2 | 8/2005 | Aceti et al. |
| 6,931,277 B1 | 8/2005 | Yuzhakov et al. |
| 6,945,952 B2 | 9/2005 | Kwon |
| 7,022,071 B2 | 4/2006 | Schaupp et al. |
| 7,045,069 B2 | 5/2006 | Ozeryansky |
| 7,097,631 B2 | 8/2006 | Trautman et al. |
| 7,169,600 B2 | 1/2007 | Hoss et al. |
| 7,211,062 B2 | 5/2007 | Kwon |
| 7,250,037 B2 | 7/2007 | Shermer et al. |
| 7,753,888 B2 | 7/2010 | Mukerjee et al. |
| 8,052,633 B2 | 11/2011 | Kendall |
| 8,062,573 B2 | 11/2011 | Kwon |
| 8,414,548 B2 | 4/2013 | Yuzhakov |
| 8,734,697 B2 | 5/2014 | Chen et al. |
| 8,883,015 B2 | 11/2014 | Kendall et al. |
| 9,283,365 B2 | 3/2016 | Kendall et al. |
| 2002/0008530 A1 | 1/2002 | Kim et al. |
| 2002/0016562 A1 | 2/2002 | Cormier et al. |
| 2002/0032415 A1 | 3/2002 | Trautman et al. |
| 2002/0128599 A1 | 9/2002 | Cormier et al. |
| 2002/0133129 A1 | 9/2002 | Arias et al. |
| 2002/0177839 A1 | 11/2002 | Cormier et al. |
| 2003/0036710 A1 | 2/2003 | Matriano et al. |
| 2003/0199810 A1 | 10/2003 | Trautman et al. |
| 2003/0199811 A1 | 10/2003 | Sage, Jr. et al. |
| 2004/0002121 A1 | 1/2004 | Regan et al. |
| 2004/0039397 A1 * | 2/2004 | Weber et al. ............ 606/90 |
| 2004/0087992 A1 | 5/2004 | Gartstein et al. |
| 2005/0042866 A1 | 2/2005 | Klapproth et al. |
| 2005/0089553 A1 | 4/2005 | Cormier et al. |
| 2005/0089554 A1 | 4/2005 | Cormier et al. |
| 2005/0126710 A1 | 6/2005 | Laermer et al. |
| 2005/0137531 A1 | 6/2005 | Prausnitz et al. |
| 2005/0143713 A1 | 6/2005 | Delmore et al. |
| 2005/0197308 A1 | 9/2005 | Dalton et al. |
| 2005/0261632 A1 | 11/2005 | Xu |
| 2006/0015061 A1 | 1/2006 | Kuo et al. |
| 2006/0055724 A1 | 3/2006 | Krawczyk et al. |
| 2006/0074376 A1 | 4/2006 | Kwon |
| 2006/0195125 A1 * | 8/2006 | Sakakine ............ A61B 17/083 |
| | | 606/157 |
| 2006/0202385 A1 | 9/2006 | Xu et al. |
| 2006/0264782 A1 | 11/2006 | Holmes et al. |
| 2007/0027474 A1 * | 2/2007 | Lasner ............ 606/219 |
| 2007/0060867 A1 | 3/2007 | Xu |
| 2007/0078376 A1 | 4/2007 | Smith |
| 2007/0224252 A1 | 9/2007 | Trautman et al. |
| 2007/0264749 A1 | 11/2007 | Birkmeyer |
| 2007/0270738 A1 * | 11/2007 | Wu et al. ............ 604/46 |
| 2007/0293815 A1 | 12/2007 | Chan et al. |
| 2007/0299388 A1 | 12/2007 | Chan et al. |
| 2008/0009811 A1 | 1/2008 | Cantor |
| 2008/0108959 A1 | 5/2008 | Jung et al. |
| 2008/0245764 A1 | 10/2008 | Pirk et al. |
| 2008/0312610 A1 | 12/2008 | Binks et al. |
| 2008/0312669 A1 * | 12/2008 | Vries et al. ............ 606/148 |
| 2009/0017210 A1 | 1/2009 | Andrianov et al. |
| 2009/0198189 A1 | 8/2009 | Simons et al. |
| 2009/0292254 A1 | 11/2009 | Tomono |
| 2010/0221314 A1 | 9/2010 | Matsudo et al. |
| 2010/0222743 A1 * | 9/2010 | Frederickson ........ A61B 17/205 |
| | | 604/136 |
| 2011/0021996 A1 | 1/2011 | Lee et al. |
| 2011/0028905 A1 | 2/2011 | Takada |
| 2011/0059150 A1 | 3/2011 | Kendall et al. |
| 2011/0160069 A1 | 6/2011 | Corrie et al. |
| 2011/0223542 A1 | 9/2011 | Kendall |
| 2011/0245776 A1 | 10/2011 | Kendall |
| 2011/0276027 A1 | 11/2011 | Trautman et al. |
| 2011/0288484 A1 | 11/2011 | Kendall et al. |
| 2012/0027810 A1 | 2/2012 | Chen et al. |
| 2012/0041412 A1 | 2/2012 | Roth et al. |
| 2012/0083741 A1 | 4/2012 | Kendall |
| 2012/0083762 A1 | 4/2012 | Kendall |
| 2012/0330250 A1 | 12/2012 | Kuwahara et al. |
| 2013/0131598 A1 | 5/2013 | Trautman et al. |
| 2013/0150822 A1 | 6/2013 | Ross |
| 2014/0243747 A1 | 8/2014 | Tokumoto et al. |
| 2014/0257188 A1 | 9/2014 | Kendall et al. |
| 2014/0276366 A1 | 9/2014 | Bourne et al. |
| 2016/0058697 A1 | 3/2016 | Kendall et al. |
| 2016/0220803 A1 | 8/2016 | Kendall et al. |
| 2017/0182301 A1 | 6/2017 | Kendall |

FOREIGN PATENT DOCUMENTS

| | | |
|---|---|---|
| EP | 0 139 286 A2 | 5/1985 |
| EP | 1 695 734 B1 | 6/2008 |
| EP | 2 213 284 A1 | 8/2010 |
| EP | 2 327 419 A1 | 6/2011 |
| JP | 2007-260889 A | 10/2007 |
| WO | 91/06571 A1 | 5/1991 |
| WO | 94/24281 A1 | 10/1994 |
| WO | 98/28037 A1 | 7/1998 |
| WO | 98/28038 A1 | 7/1998 |
| WO | 99/02694 A1 | 1/1999 |
| WO | 99/42564 A2 | 8/1999 |
| WO | 99/64580 A1 | 12/1999 |
| WO | 00/05339 A1 | 2/2000 |

(56) References Cited

FOREIGN PATENT DOCUMENTS

| | | |
|---|---|---|
| WO | 00/42215 A1 | 7/2000 |
| WO | 00/74763 A2 | 12/2000 |
| WO | 00/74764 A1 | 12/2000 |
| WO | 01/03361 A1 | 1/2001 |
| WO | 01/33614 A1 | 5/2001 |
| WO | 01/85207 A2 | 11/2001 |
| WO | 02/064193 A2 | 8/2002 |
| WO | 02/074173 A1 | 9/2002 |
| WO | 02/075794 A2 | 9/2002 |
| WO | 02/085446 A2 | 10/2002 |
| WO | 02/085447 A2 | 10/2002 |
| WO | 02/100476 A2 | 12/2002 |
| WO | 03/020359 A2 | 3/2003 |
| WO | 03/026732 A2 | 4/2003 |
| WO | 03/048031 A2 | 6/2003 |
| WO | 03/053258 A1 | 7/2003 |
| WO | 03/092785 A1 | 11/2003 |
| WO | 2004/000389 A2 | 12/2003 |
| WO | 2004/024224 A1 | 3/2004 |
| WO | 2005/049108 A2 | 6/2005 |
| WO | 2005/060621 A2 | 7/2005 |
| WO | 2005/069736 A2 | 8/2005 |
| WO | 2005/072360 A2 | 8/2005 |
| WO | 2005/072630 A1 | 8/2005 |
| WO | 2005/123173 A1 | 12/2005 |
| WO | 2006/055799 A1 | 5/2006 |
| WO | 2006/101459 A1 | 9/2006 |
| WO | 2006/108185 A1 | 10/2006 |
| WO | 2006/116281 A2 | 11/2006 |
| WO | 2006/138719 A2 | 12/2006 |
| WO | 2007/002123 A2 | 1/2007 |
| WO | 2007/002521 A2 | 1/2007 |
| WO | WO 2007002521 A2 * 1/2007 ........... A61B 17/205 | |
| WO | 2007/012114 A1 | 2/2007 |
| WO | 2007/030477 A2 | 3/2007 |
| WO | 2007/054090 A1 | 5/2007 |
| WO | 2007/061781 A1 | 5/2007 |
| WO | 2007/061871 A1 | 5/2007 |
| WO | 2007/070004 A2 | 6/2007 |
| WO | 2007/080427 A2 | 7/2007 |
| WO | 2007/127976 A2 | 11/2007 |
| WO | 2008/010681 A1 | 1/2008 |
| WO | 2008/011625 A2 | 1/2008 |
| WO | 2008/053481 A1 | 5/2008 |
| WO | 2008/069566 A1 | 6/2008 |
| WO | 2008/083209 A2 | 7/2008 |
| WO | 2008/091602 A2 | 7/2008 |
| WO | 2009/040548 A1 | 4/2009 |
| WO | 2009/066763 A1 | 5/2009 |
| WO | 2009/079712 A1 | 7/2009 |
| WO | 2009/081122 A1 | 7/2009 |
| WO | 2009/097660 A1 | 8/2009 |
| WO | 2009/140735 A1 | 11/2009 |
| WO | WO 2009140735 A1 * 11/2009 | |
| WO | 2010/042996 A1 | 4/2010 |
| WO | 2010/071918 A1 | 7/2010 |
| WO | 2010/109471 A1 | 9/2010 |
| WO | 2011/105496 A1 | 9/2011 |
| WO | 2011/116388 A1 | 9/2011 |
| WO | 2013/053022 A1 | 4/2013 |
| WO | 2013/055641 A1 | 4/2013 |

OTHER PUBLICATIONS

International Search Report, dated Oct. 25, 2011, for International Application No. PCT/AU2011/000890, 4 pages.
Aichele et al., "Antiviral Cytotoxic T Cell Response Induced by in Vivo Priming With a Free Synthetic Peptide," *J. Exp. Med.* 171:1815-1820, 1990.
Albert et al., "Dendritic cells acquire antigen from apoptotic cells and induce class I-restricted CTLs," *Nature* 392:86-89, 1998.
Albert et al., "Tumor-specific killer cells in paraneoplastic cerebellar degeneration," *Nature Medicine* 4(11):1321-1324, 1998.
Anderson, "Cutaneous Microdialysis: Is it Worth the Sweat?," *Journal of Investigative Dermatology* 126:1207-1209, 2006.
Athanasopoulos et al., "Gene therapy vectors based on adeno-associated virus: Characteristics and applications to acquired and inherited diseases (Review)," *International Journal of Molecular Medicine* 6:363-375, 2000.
Bachmann et al., "Dendritic cells process exogenous viral proteins and virus-like particles for class I presentation to $CD8^+$ cytotoxic T lymphocytes," *Eur. J. Immunol.* 26:2595-2600, 1996.
Camilli et al., "*Listeria monocytogenes* Mutants Lacking Phosphatidylinositol-specific Phospholipase C Are Avirulent," *J. Exp. Med.* 173:751-754, 1991.
Cormier et al., "Transdermal delivery of desmopressin using a coated microneedle array patch system," *Journal of Controlled Release* 97:503-511, 2004.
Cox et al., "Adjuvants—a classification and review of their modes of action," *Vaccine* 15(3):248-256, 1997.
Dreyer, "Microneedles: Microprocessing in Medicine," ENMA 465: Microprocessing, May 10, 2004, 23 pages.
Feng et al., "Molecular Biomarkers for Cancer Detection in Blood and Bodily Fluids," *Critical Reviews in Clinical Laboratory Sciences* 43(5-6):497-560, 2006.
Gao et al., "Priming of Influenza Virus-Specific Cytotoxic T Lymphocytes Vivo by Short Synthetic Peptides," *The Journal of Immunology* 147:3268-3273, 1991.
Gardeniers et al., "Silicon Micromachined Hollow Microneedles for Transdermal Liquid Transport," *Journal of Microelectromechanical Systems* 12(6):855-862, 2003.
Gill et al., "Coated microneedles for transdermal delivery," *Journal of Controlled Release* 117:227-237, 2007.
Gill et al., "Coating Formulations for Microneedles," *Pharmaceutical Research* 24(7):1369-1380, 2007.
International Preliminary Report on Patentability, dated Jul. 8, 2010, for International Application No. PCT/AU2008/001903, 8 pages.
International Preliminary Report on Patentability, dated Jun. 7, 2006, for International Application No. PCT/GB2005/000336, 11 pages.
International Search Report, dated Feb. 20, 2009, for International Application No. PCT/AU2008/001903, 5 pages.
International Search Report, dated Feb. 20, 2013, for International Application No. PCT/AU2012/001289, 13 pages.
Ito et al., "Feasibility of microneedles for percutaneous absorption of insulin," *European Journal of Pharmaceutical Sciences* 29:82-88, 2006.
Ito et al., "Self-dissolving microneedles for the percutaneous absorption of EPO in mice," *Journal of Drug Targeting* 14(5):255-261, 2006.
Ito et al., "Evaluation of self-dissolving needles containing low molecular weight heparin (LMWH) in rats," *International Journal of Pharmaceutics* 349:124-129, 2008.
Jondal et al., "MHC Class I-Restricted CTL Responses to Exogenous Antigens," *Immunity* 5:295-302, 1996.
Kay et al., "Viral vectors for gene therapy: the art of turning infectious agents into vehicles of therapeutics," *Nature Medicine* 7(1):33-40, 2001.
Kendall et al., "The mechanical properties of the skin epidermis in relation to targeted gene and drug delivery," *Biomaterials* 28:4968-4977, 2007.
Kuzu et al., "In vivo priming effect during various stages of ontogeny of an influenza A virus nucleoprotein peptide," *Eur. J. Immunol.* 23:1397-1400, 1993.
Kwon, "In Vitro Evaluation of Transdermal Drug Delivery by a Micro-needle Patch," Controlled Release Society $31^{st}$ Annual Meeting, 2004, 2 pages.
Kwon, "Acne Treatment by a Dissolvable Micro-Needle Patch," TheraJect Inc., 2006, 2 pages.
Kwon et al., "Rapid Intradermal Drug Delivery by a Dissolvable Micro-Needle Patch," Controlled Release Society $32^{nd}$ Annual Meeting, 2005, 2 pages.
Kwon et al., "In Vitro Modeling of Transdermal PTH Delivery by Dissolving Micro-needle Patch," TheraJect Inc., 2007, 2 pages.
Lee et al., "Dissolving microneedles for transdermal drug delivery," *Biomaterials* 29:2113-2124, 2008.

(56) References Cited

OTHER PUBLICATIONS

Lin et al., "Silicon-Processed Microneedles," *IEEE Journal of Microelectromechanical Systems* 8(1):78-84, 1999.

Matriano et al., "Macroflux® Microprojection Array Patch Technology: A New and Efficient Approach for Intracutaneous Immunization," *Pharmaceutical Research* 19(1):63-70, 2002.

Mengaud et al., "Expression in *Escherichia coli* and Sequence Analysis of the Listeriolysin O Determinant of *Listeria monocytogenes,*" *Infection and Immunity* 56(4):766-772, 1988.

Miyano et al., "Sugar Micro Needles as Transdermic Drug Delivery System," *Biomedical Microdevices* 7(3):185-188, 2005.

Miyano et al., "Hydrolytic Microneedles as Transdermal Drug Delivery System," *Transducers & Eurosensors '07*, The 14th International Conference on Solid-State Sensors, Actuators and Microsystems, Lyon, France, Jun. 10-14, 2007, 4 pages.

Moore et al., "Introduction of Soluble Protein into the Class I Pathway of Antigen Processing and Presentation," *Cell* 54:777-785, 1988.

Mukerjee et al., "Microneedle array for transdermal biological fluid extraction and in situ analysis," *Sensors and Actuators A* 114:267-275, 2004.

Office Action, dated Feb. 17, 2012, for Chinese Patent Application No. 200980104635.3, 7 pages. (English Translation).

Oh et al., "Intradermal influenza vaccine delivery using skin-penetrating dissolvable vaccine microneedles," 2006 AAPS Annual Meeting and Exposition, 1 page.

Oh et al., "Demonstration of Dose-controlled Delivery by Dissolvable Micro-needle Arrays," 34th Annual CRS Conference, Jun. 2007, 2 pages.

Palmer et al., "Streptolysin O: A Proposed Model of Allosteric Interaction between a Pore-Forming Protein and Its Target Lipid Bilayer," *Biochemistry* 37:2378-2383, 1998.

Park et al., "Biodegradable polymer microneedles: Fabrication, mechanics and transdermal drug delivery," *Journal of Controlled Release* 104:51-66, 2005.

Park et al., "Polymer Microneedles for Controlled-Release Drug Delivery," *Pharmaceutical Research* 23(5):1008-1019, 2006.

Park et al., "Towards the silicon nanowire-based sensor for intracellular biochemical detection," *Biosensors and Bioelectronics* 22:2065-2070, 2007.

Portnoy et al., "Capacity of Listeriolysin O, Streptolysin O, and Perfringolysin O to Mediate Growth of *Bacillus subtilis* within Mammalian Cells," *Infection and Immunity* 60(7):2710-2717, 1992.

Rossjohn et al., "Structure of a Cholesterol-Binding, Thiol-Activated Cytolysin and a Model of Its Membrane Form," *Cell* 89:685-692, 1997.

Schulz et al., "Peptide-induced antiviral protection by cytotoxic T cells," *Proc. Natl. Acad. Sci. USA* 88:991-993, 1991.

Silver et al., "Viscoelastic Properties of Young and Old Human Dermis: A Proposed Molecular Mechanism for Elastic Energy Storage in Collagen and Elastin," *J. Appl Polym Sci* 86:1978-1985, 2002.

Stoeber et al., "Arrays of Hollow Out-of-Plane Microneedles for Drug Delivery," *Journal of Microelectromechanical Systems* 14(3):472-479, 2005.

Sullivan et al., "Minimally Invasive Protein Delivery with Rapidly Dissolving Polymer Microneedles," *Adv. Mater.* 20:933-938, 2008.

Tao et al., "A systematic study of dry etch process for profile control of silicon tips," *Microelectronic Engineering* 78-79:147-151, 2005.

Tsuchiya et al., "Development of Blood Extraction System for Health Monitoring System," *Biomedical Microdevices* 7(4):347-353, 2005.

Tyagi et al., "Molecular Beacons: Probes that Fluoresce upon Hybridization," *Nature Biotechnology* 14:303-308, 1996.

Vigna et al., "Lentiviral vectors: excellent tools for experimental gene transfer and promising candidates for gene therapy," *The Journal of Gene Medicine* 2:308-316, 2000.

Walther et al., "Viral Vectors for Gene Transfer—A Review of Their Use in the Treatment of Human Diseases," *Drugs* 60(2):249-271, 2000.

Wang et al., "Label-free hybridization detection of a single nucleotide mismatch by immobilization of molecular beacons on an agarose film," *Nucleic Acids Research* 30(12):e61, 2002. (9 pages).

Widera et al., "Effect of delivery parameters on immunization to ovalbumin following intracutaneous administration by a coated microneedle array patch system," *Vaccine* 24:1653-1664, 2006.

Written Opinion of the International Searching Authority, dated Feb. 20, 2009, for International Application No. PCT/AU2008/001903, 6 pages.

Wu et al., "Production of viral vectors for gene therapy applications," *Current Opinions in Biotechnology* 11:205-208, 2000.

Yuan et la., "Measuring microelastic properties of stratum corneum," *Colloids and Surfaces B: Biointerfaces* 48:6-12, 2006.

Zheng et al., "Multiplexed electrical detection of cancer markers with nanowire sensor arrays," *Nature Biotechnology* 23(10):1294-1301, 2005.

Zhou et al., "Liposome-Mediated Cytoplasmic Delivery of Proteins: An Effective Means of Accessing the MHC Class I-Restricted Antigen Presentation Pathway," *Immunomethods* 4:229-235, 1994.

Extended European Search Report, dated Nov. 10, 2015, for European Application No. 12840561.0-1506 / 2765927, 11 pages.

Patent Examination Report No. 1, dated Apr. 11, 2016, for Australian Application No. 2012323782, 3 pages.

Crichton et al., "The viscoelastic, hyperelastic and scale dependent behaviour of freshly excised individual skin layers," *Biomaterials* 32:4670-4681, 2011 (13 pages).

Fernando et al., "Potent Immunity to Low Doses of Influenza Vaccine by Probabilistic Guided Micro-Targeted Skin Delivery in a Mouse Model," *PLoS One* 5(4):e10266, 2010 (11 pages).

Henry et al., "Microfabricated Microneedles: A Novel Approach to Transdermal Drug Delivery," *Journal of Pharmaceutical Sciences* 87(8):922-925, 1998 (4 pages).

McAllister et al., "Microfabricated needles for transdermal delivery of macromolecules and nanoparticles: Fabrication methods and transport studies," *PNAS* 100(24): 13755-13760, 2003 (6 pages).

Australian Examination report No. 2 for standard patent application, dated Jan. 9, 2017, for corresponding Australian application No. 2012323782, 4 pages.

Australian Patent Examination Report No. 1, dated Mar. 27, 2013, for corresponding Australian application No. 2009212106, 5 pages.

Canadian Examination Report, dated Apr. 23, 2015, for corresponding Canadian application No. 2,749,347, 4 pages.

Canadian Examination Report, dated Feb. 17, 2015, for corresponding Canadian application No. 2,745,339, 4 pages.

Chinese 2nd Office Action, dated Sep. 24, 2012, for corresponding Chinese application No. 200980104635.3, 9 pages. (with English Translation).

Chinese 3rd Office Action, dated Dec. 28, 2012, for corresponding Chinese application No. 200980104635.3, 6 pages. (with English Translation).

Extended European Search Report and Written Opinion, dated Jul. 20, 2012, for corresponding EP application No. 09833918.7, 9 pages.

Extended European Search Report and Written Opinion, dated Sep. 26, 2014, for corresponding EP application No. 09707729.1, 9 pages.

International Search Report and Written Opinion of the International Searching Authority, dated Mar. 7, 2016, for corresponding international application No. PCT/AU2016/050056, 13 pages.

International Search Report and Written Opinion of the International Searching Authority, dated Dec. 6, 2016, for corresponding international application No. PCT/AU2016/050867, 20 pages.

International Search Report and Written Opinion of the International Searching Authority, dated Dec. 22, 2016, for corresponding international application No. PCT/AU2016/050907, 14 pages.

Ma et al., "A PZT Insulin Pump Integrated with a Silicon Micro Needle Array for Transdermal Drug Delivery," 56th Electronic Components & Technology Conference, San Diego, CA, May 30-Jun. 2, 2006, 5 pages.

Crichton et al., "The effect of strain rate on the precision of

(56) References Cited

OTHER PUBLICATIONS penetration of short densely-packed microprojection array patches coated with vaccine," *Biomaterials* 31(16):4562-4572, 2010.

* cited by examiner

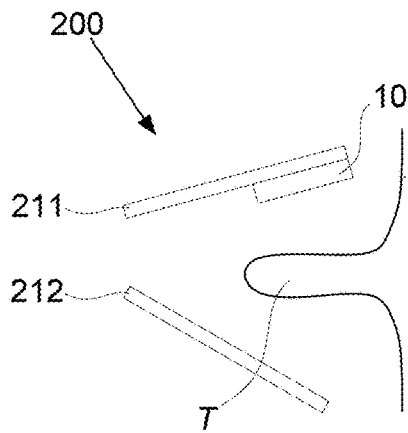
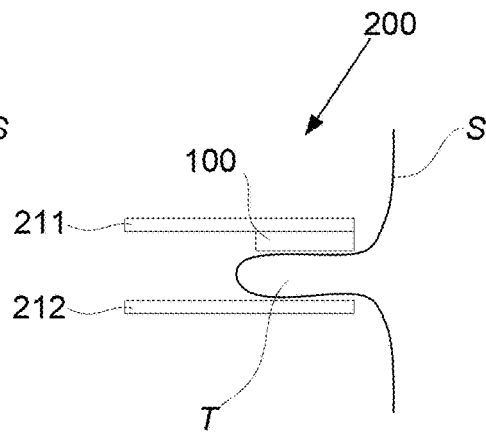
Fig. 2A  Fig. 2B
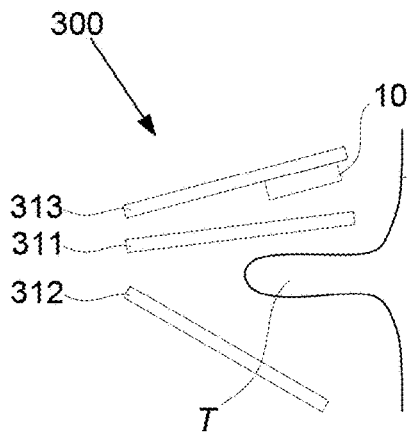
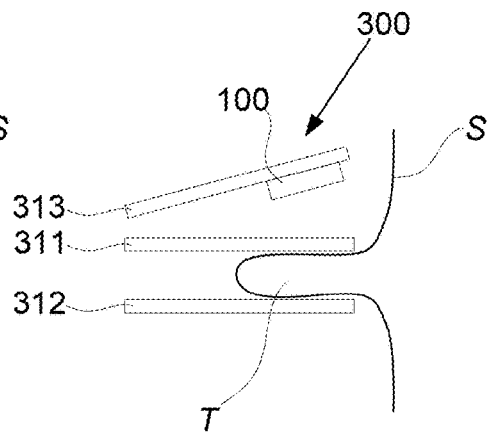
Fig. 3A  Fig. 3B
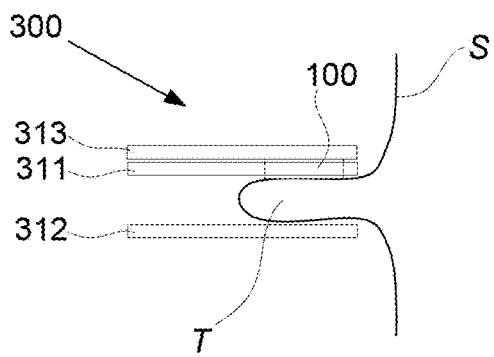
Fig. 3C

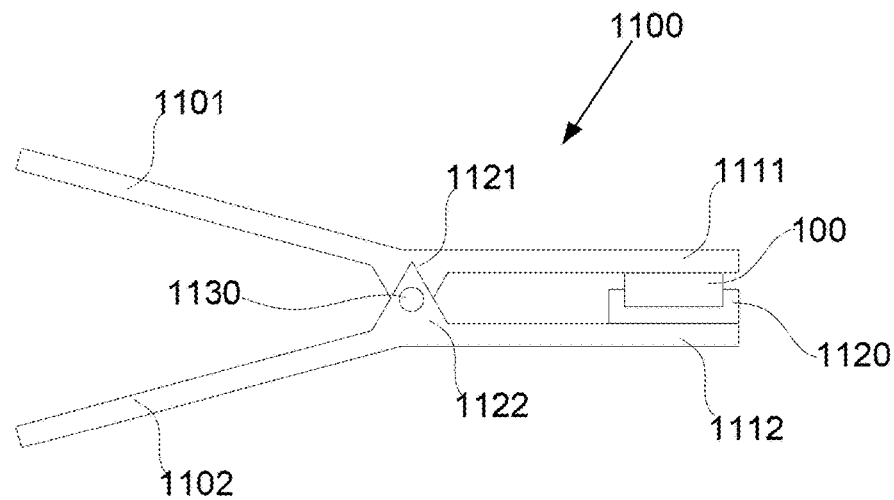
Fig. 11A
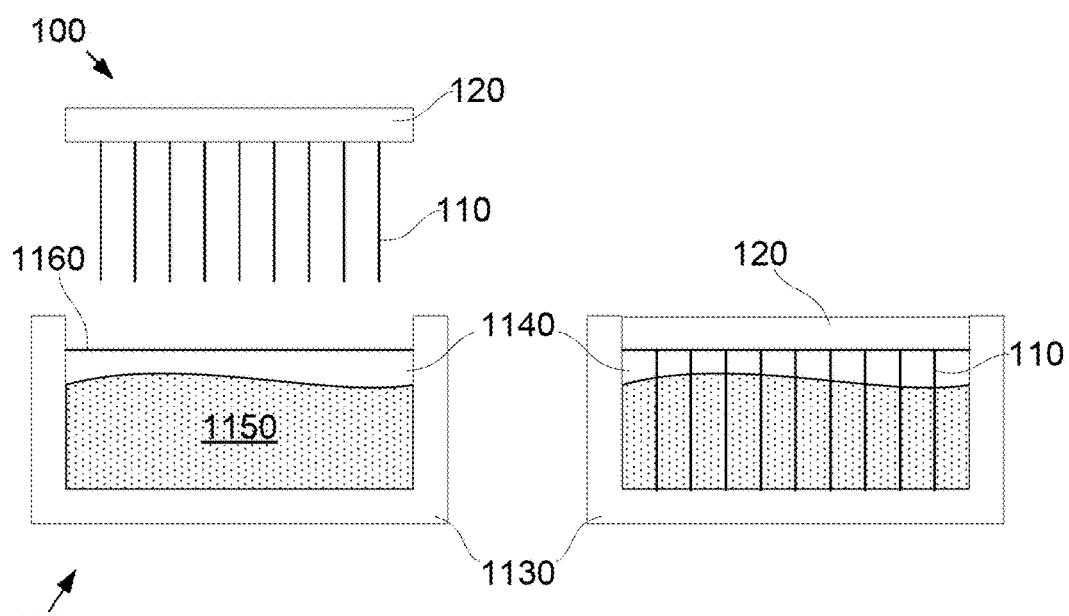
Fig. 11B  Fig. 11C

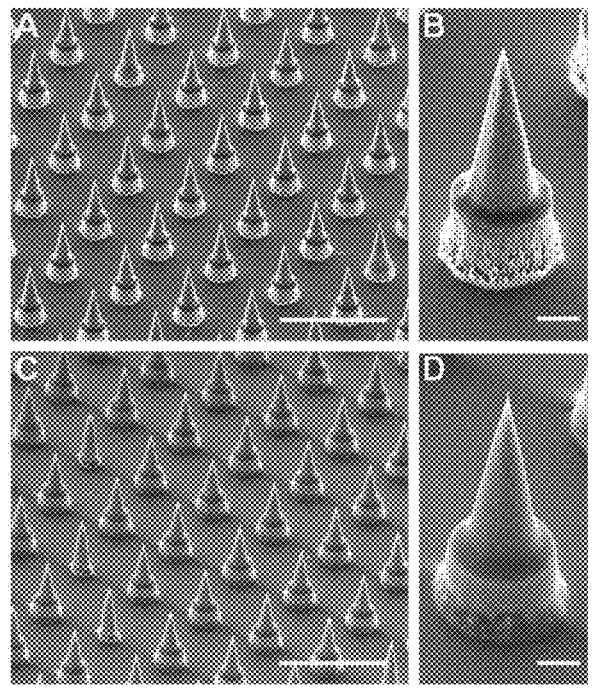
Fig. 16A  Fig. 16B
Fig. 16C  Fig. 16D
Fig. 17A
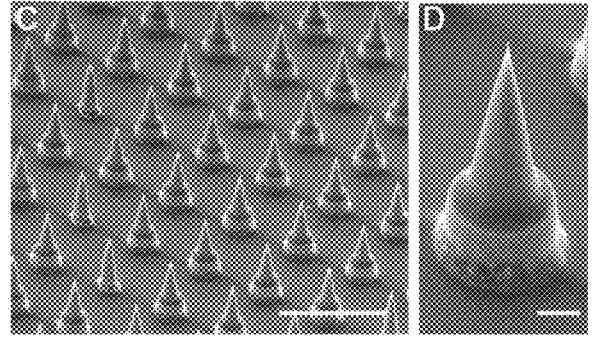
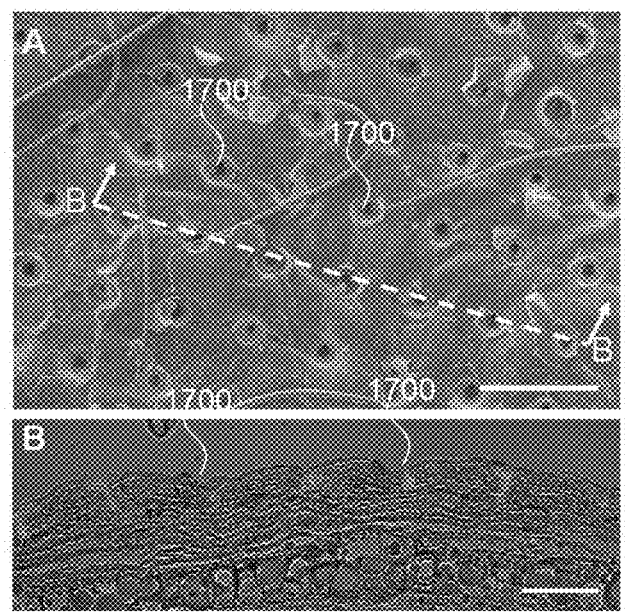
Fig. 17B Fig. 18A    Fig. 18B    Fig. 18C
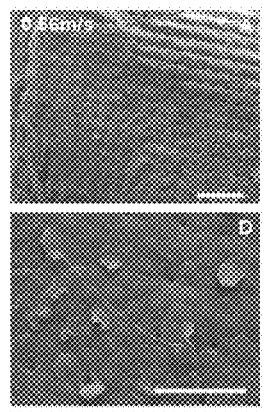 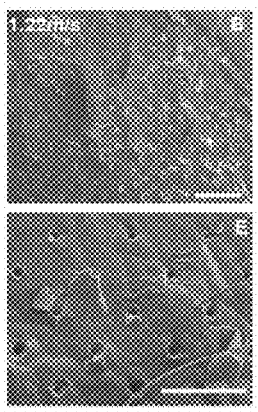 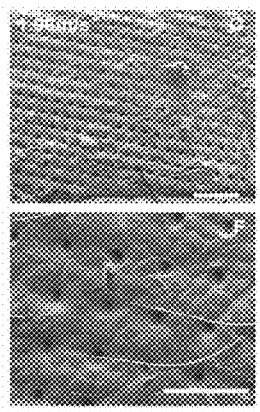
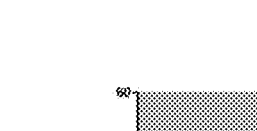  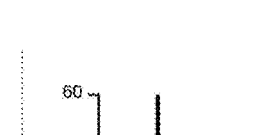
Fig. 18D    Fig. 18E    Fig. 18F
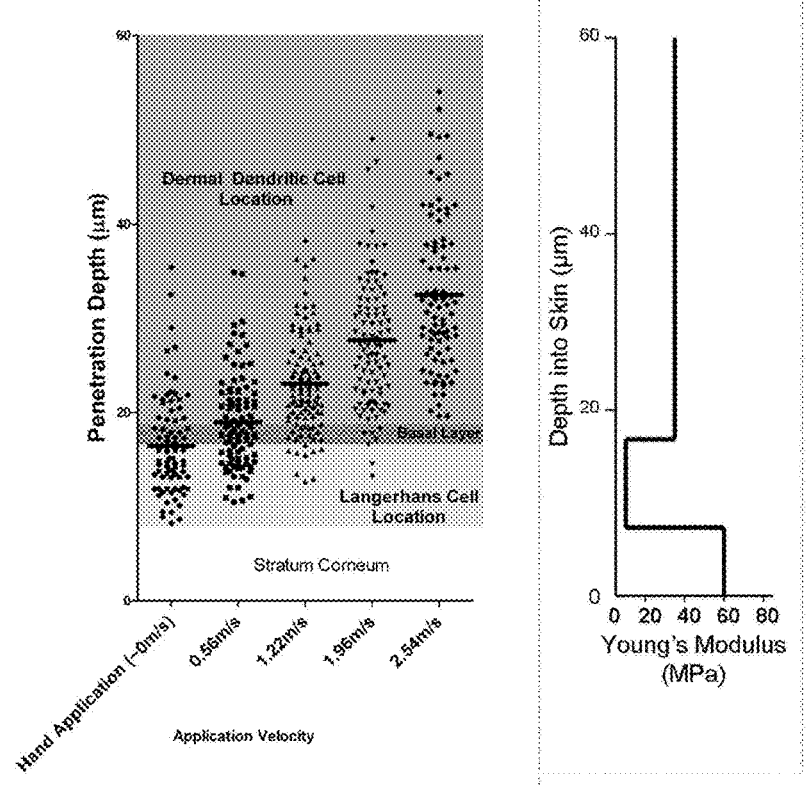
Fig. 19A

PATCH APPLYING APPARATUS

BACKGROUND OF THE INVENTION

The present invention relates to apparatus and a method for applying a patch to a subject, and in particular to apparatus and a method for applying a patch having a number of projections thereon.

DESCRIPTION OF THE PRIOR ART

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

It is known to provide patches including a number of projections thereon to allow bioactive material to be administered to a subject. Such arrays of projections or needles on a patch are an increasingly effective way of delivering therapeutic agents or biomarkers since there is minimal or no pain, little or no injury from the needle and highly reduced possibility of cross infection. The solid projections or needles on a patch can be coated with drugs or macromolecules. These can be subsequently delivered to a desired target by the penetration of the projections or needles into the skin.

For example, WO2005/072630 describes devices for delivering bioactive materials and other stimuli to living cells, methods of manufacture of the device and various uses of the device, including a number of medical applications. The device comprises a plurality of projections which can penetrate a body surface so as to deliver the bioactive material or stimulus to the required site. The projections are typically solid and the delivery end section of the projection is so dimensioned as to be capable of insertion into targeted cells or specific sites to deliver the bioactive material or stimulus without appreciable damage to the targeted cells or specific sites therein.

In order to apply the patches to a subject, it is known to provide applicator devices.

WO2005/123173 describes a patch application device wherein the patch is retained in position within the collar until delivery through contact of at least one obstruction inside the collar with a portion of an adhesive on the front surface (e.g., microneedle-containing surface) of the patch. The collar and patch can be used to form separate replaceable cartridges, and the combination can be provided as a kit.

U.S. Pat. No. 7,097,631 describes an applicator for applying a microprojection member to the stratum corneum of a patient having a housing, a piston moveable within the housing and a cap adapted to activate the applicator. The applicator is self-setting and auto-triggering, which allows the applicator to be used by patient's having neither the strength, nor the manual dexterity to pre-set and activate other types of applicator devices.

U.S. Pat. No. 7,211,062 describes a solid drug perforator (SSP) system and an associated drug reservoir for delivering therapeutic, prophylactic and/or cosmetic compounds, for nutrient delivery and for drug targeting. For drug delivery, the SSP system includes an active drug ingredient and a matrix of perforator material that biodegrades or dissolves quickly upon contact with a patient's body. The SSP system provides a skin barrier perforator and a controller for prompt initiation and cut-off of drug delivery. In a preferred method of transdermal drug delivery, an SSP system containing a selected drug penetrates into an epidermis or dermis, and the drug is promptly released from the (dissolving) SSP system perforator. An additional drug is optionally delivered from a patch reservoir through skin pores created by insertion of the perforator. Formulation and fabrication procedures for the SSP and associated reservoir are also provided. An SSP system can be fabricated with variety of shapes and dimensions.

WO2006/116281 describes a device including a microprotrusion member having a skin-contacting surface and plurality of stratum corneum-piercing microprotrusions thereon and the use thereof to treat skin disorders, such as acne.

WO2006/108185 describes a microneedle application device for moving a microneedle array toward a target skin location includes a feedback sensor. The feedback sensor is operably connected to the microneedle application device, and is capable of generating an output corresponding to forces between the target skin location and the microneedle application device.

The above described arrangements therefore utilise a piston or plunger, which is axially driven, to thereby urge the patch into engagement with the subject.

WO2007/02521 describes an applicator device including a housing, an impactor for impacting a microneedle array and accelerating the microneedle array toward the target site, wherein the impactor is capable of moving along an arcuate path to move the microneedle array toward the target site. Also, an applicator device including a housing, a patch applicator pivotally supported by the housing, and a torsion spring. The patch applicator has a retaining portion and a patch contacting portion, and the patch contacting portion is capable of moving along a substantially arcuate path between a first position and a second position. The torsion spring is capable of biasing the patch applicator relative to the housing.

U.S. Pat. No. 6,743,211 Microneedle devices and methods of use thereof are provided for the enhanced transport of molecules, including drugs and biological molecules, across tissue by improving the interaction of microneedles and a deformable, elastic biological barrier, such as human skin. The devices and methods act to (1) limit the elasticity, (2) adapt to the elasticity, (3) utilize alternate ways of creating the holes for the microneedles to penetrate the biological barrier, other than the simply direct pressure of the microneedle substrate to the barrier surface, or (4) any combination of these methods. In preferred embodiments for limiting the elasticity of skin, the microneedle device includes features suitable for stretching, pulling, or pinching the skin to present a more rigid, less deformable, surface in the area to which the microneedles are applied (i.e. penetrate). In a preferred embodiments for adapting the device to the elasticity of skin, the device comprising one or more extensions interposed between the substrate and the base end of at least a portion of the microneedles.

However, each of the above described arrangements are relatively complex requiring the use of a housing containing an movable applicator arm or plunger, thereby rendering the apparatus complex and expensive to manufacture. The applicator must also be carefully positioned and aligned to ensure penetration of the skin by the patch needles, which in makes the applicators difficult to use successfully.

SUMMARY OF THE PRESENT INVENTION

In a first broad form the present invention seeks to provide apparatus for applying a patch to a subject, the patch having a number of projections thereon, the apparatus including:

a) opposable jaws movable between open and engaging positions, wherein in the open position the jaws can receive at least part of the subject, and in the engaging position the jaws can engage the at least part of the subject; and, b) a patch support for supporting a patch, and wherein the patch support is for urging the patch against the at least part of the subject.

Typically the apparatus is for applying the patch to thereby at least partial control at least one application parameter.

Typically the at least one application parameter is controlled to thereby at least partially control a depth of penetration of the projections.

Typically the at least one application parameter includes at least one of:

a) an application force; and,
b) an application velocity.

Typically the apparatus is adapted to apply a patch at a velocity of at least 1 m/s.

Typically the apparatus includes a retaining system for retaining the jaws in the engaging position.

Typically the apparatus includes a biasing mechanism for urging the jaws towards the engaging position.

Typically the biasing mechanism is used to control application parameters.

Typically the apparatus includes a releasable stop for holding the jaws in the open position, release of the stop causing the jaws to be urged into the engaging position.

Typically the apparatus includes a releasable clip that engages when the jaws are in the engaging position.

Typically the apparatus includes first and second arms, each arm having a first end defining the jaws.

Typically the arms include second ends opposite the first ends, the arms being connected at the second ends.

Typically the arms include second ends opposite the first ends, the arms being connected at a point between the first and second ends such that urging the second ends towards each other causes the jaws to move towards the open position.

Typically the arms are pivotally connected.

Typically the arms are flexible arms.

Typically the arms are made of a resilient material.

Typically the arms are made of at least one of:

a) plastic;
b) metal;
c) composite material; and,
d) a polymer.

Typically the patch support is mounted on one of the first and second arms.

Typically the apparatus includes a third arm mounted to the first and second arms, the patch support being provided on the third arm.

Typically one of the first and second arms includes an aperture aligned with the patch support on the third arm so that the patch extends through the aperture when engaging the subject, in use.

Typically the aperture is for applying a force to a tissue surface of the subject prior to the patch being applied, to thereby at least one of:

a) compress the tissue;
b) stretch the tissue; and,
c) pre-stress the tissue.

Typically the apparatus further includes a biasing mechanism for urging the first and second arms together so that the aperture applies the force to the tissue surface.

Typically the apparatus further includes a fourth arm mounted to the first and second arms, a patch support being provided on the fourth arm.

Typically one of the first and second arms includes an aperture aligned with the patch support on the fourth arm so that the patch extends through the aperture when engaging the subject, in use.

Typically the aperture is for applying a force to a tissue surface of the subject prior to the patch being applied, to thereby at least one of:

a) compress the tissue;
b) stretch the tissue; and,
c) pre-stress the tissue.

Typically the apparatus further includes a biasing mechanism for urging the first and second arms together so that the aperture applies the force to the tissue surface.

Typically at least one arm includes a housing for receiving the patch when the jaws are in the engaging positions.

Typically the housing is for at least one of:

a) containing a material to be applied to patch for delivery to the subject; and,
b) receiving a sample from the subject.

Typically the apparatus includes a patch.

Typically the patch includes projections having channels therethrough for at least one of:

a) delivering fluid to the subject; and,
b) extracting fluid from the subject.

Typically the apparatus includes a reservoir in fluid communication with the channels for at least one of:

a) providing fluid for delivery to the subject; and,
b) receiving fluid extracted from the subject.

Typically the reservoir is provided on at least one jaw.

Typically the patch is mounted on a first side of a jaw and the reservoir is provided on a second opposing side of the jaw.

Typically fluid is delivered or extracted by at least one of:

a) using a moveable jaw;
b) deformation of the reservoir;
c) a syringe;
d) a plunger;
e) a plunger cap;
f) a mechanical actuator;
g) a manual actuator; and,
h) an electronic actuator.

Typically fluid is delivered by at least one of:

a) infusion; and,
b) urging the fluid through the channels.

Typically fluid is extracted by capillary action.

Typically the projections have a density of at least one of:

a) between 1,000-30,000 projections/cm$^2$;
b) less than 1,000 projections/cm$^2$; and,
c) less than 100 projections/cm$^2$.

Typically the projections have a length of at least one of a) between 10 to 200 μm; and,
b) greater than 200 μm.

Typically the projections have a length of 90 μm

Typically the projections have a radius of curvature of at least one of:

a) greater than 0.5 μm;
b) greater than 1 μm; and,
c) greater than 5 μm.

Typically the projections include a support section and a targeting section.

Typically the targeting section has a diameter of less than at least one of:

a) 50 μm;
b) 100 μm;

c) 150 μm; and,
d) 400 μm.

Typically a length for the targeting section is at least:
a) less than 50 μm; and,
b) less than 100 μm; and,
c) less than 300 μm.

Typically a length for the support section is at least one of:
a) for epidermal delivery <200 μm;
b) for dermal cell delivery <1000 μm;
c) for delivery to basal cells in the epithelium of the mucosa 600-800 μm; and,
d) for lung delivery of the order of 100 μm.

Typically the projections are shaped to at least partially control a depth of penetration of the projection in use.

Typically the projections have a stepped configuration.

Typically the projections have a supporting section having a diameter greater than a diameter of a targeting section.

In a second broad form the present invention seeks to provide a method for applying a patch to a subject, the method including:
a) positioning at least part of a subject between opposable jaws providing in an open position; and,
b) causing the jaws to move to an engaging position in which the jaws can engage the at least part of the subject, so that a patch can engage the at least part of the subject.

Typically the method includes using a retaining system for retaining the jaws in the engaging position.

Typically the method includes using a biasing mechanism for urging the jaws towards the engaging position.

Typically the method includes releasing a stop to cause the jaws to be urged into the engaging position.

Typically the apparatus includes first and second arms, each arm having a first end defining the jaws, and wherein the method includes using the arms to move the jaws into the engaging position.

Typically the apparatus includes a third arm mounted to the first and second arms, the patch support being provided on the third arm, and the method including applying the patch to the subject using the third arm.

Typically the method includes using an aperture of at least one of the first and second supports to apply a force to a tissue surface of the subject prior to the patch being applied, to thereby at least one of:
a) compress the tissue;
b) stretch the tissue; and,
c) pre-stress the tissue.

Typically the method includes using a biasing mechanism for urging the first and second arms together so that the aperture applies the force to the tissue surface.

Typically the method includes using a patch including projections having channels therethrough to at least one of:
a) deliver fluid to the subject; and,
b) extract fluid from the subject.

Typically the method includes delivering or extracting fluid using at least one of:
a) using a moveable jaw;
b) deformation of the reservoir;
c) a syringe;
d) a plunger;
e) a plunger cap;
f) a mechanical actuator;
g) a manual actuator; and,
h) an electronic actuator.

BRIEF DESCRIPTION OF THE DRAWINGS

An example of the present invention will now be described with reference to the accompanying drawings, in which.

FIGS. 2A and 2B are schematic diagrams of a first example of apparatus for applying a patch to a subject;

FIGS. 3A to 3C are schematic diagrams of a second example of apparatus for applying a patch to a subject;

FIG. 11A is a schematic diagram of a third example of apparatus for applying a patch to a subject;

FIGS. 11B and 11C are schematic diagrams of an example well;

FIGS. 16A and 16B are SEM images of example uncoated patches;

FIGS. 16C and 16D are SEM images of example coated patches;

FIG. 17A is a Cryo-SEM image of penetration of projections into mouse ear;

FIG. 17B is a cross sectional view of the penetration of projections into mouse ear;

FIGS. 18A to 18F are Cryo-SEM images showing the skin surface after patch application at different application velocities;

FIG. 19A is a graph of raw data showing projection penetration at different application velocities;

DETAILED DESCRIPTION OF THE PREFERRED EMBODIMENTS

An example of apparatus for delivering material to, retrieving material from, or detecting analytes in, a subject, will now be described with reference to FIGS. 1A to 1F.

In this example, the apparatus includes a patch 100 having a number of projections 110 provided on a surface 121 of a substrate 120. The projections 110 and substrate 120 may be formed from any suitable material, but in one example, are formed from a silicon type material, allowing the device to be fabricated using processes such as vapour deposition, silicon etching, Deep Reactive Ion Etching (DRIE), or the like. The projections are therefore typically solid, non-porous and non-hollow.

However, this is not essential and alternative materials may be used such as organosilicates (eg aminosilanes), polymers, or the like, and alternative manufacturing techniques may also be used, such as molding or the like.

In the example shown, the patch has a width W and a breadth B with the projections 110 being separated by spacing S.

Figure 1A:
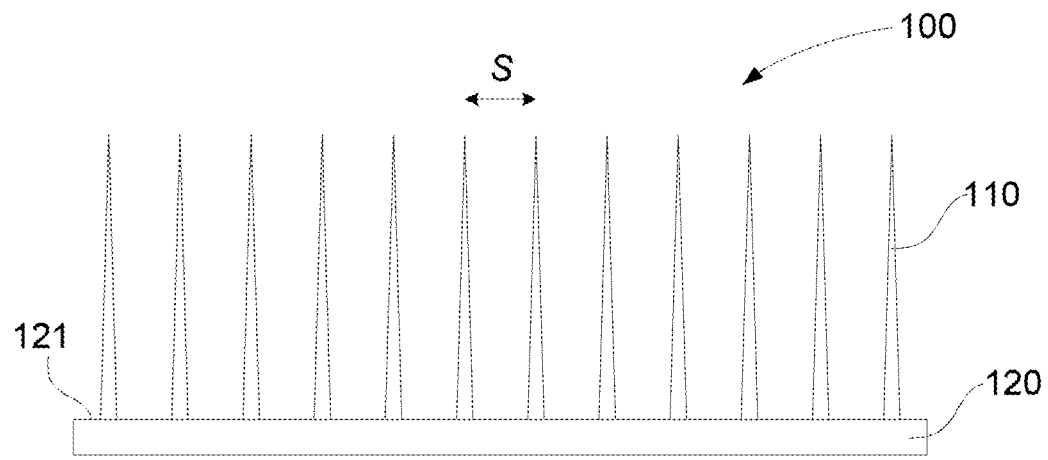
—FIGS. 1A and 1B are schematic side and plan views, respectively, of an example of device for delivery of material to targets within a body.
Figure 1B:
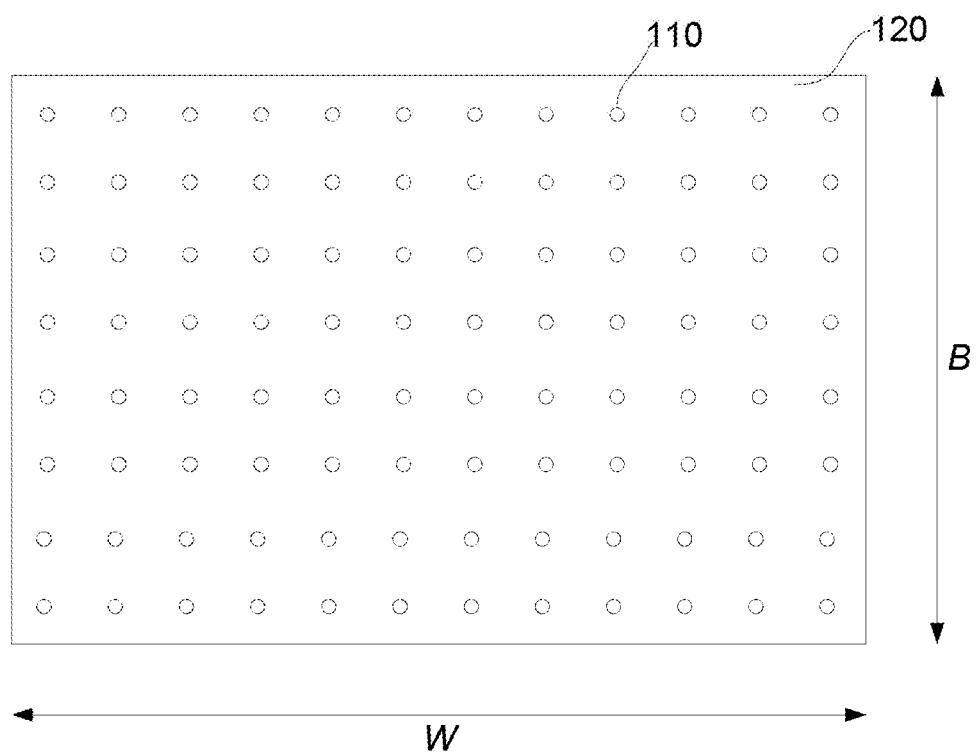
Figure 1C:
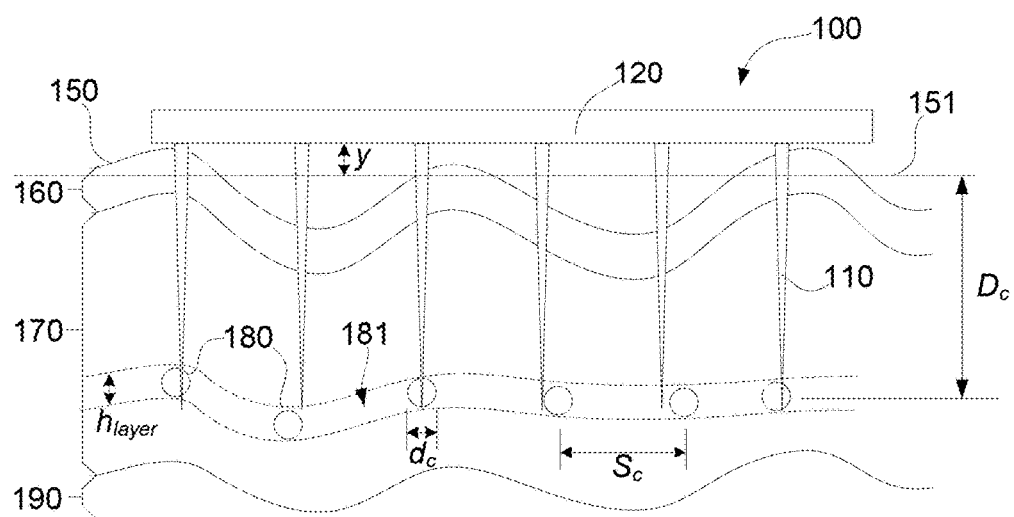
FIG. 1C is a schematic diagram of an example of the device of FIG. 1A in use.

In use, the patch 100 is positioned against a surface of a subject, allowing the projections to enter the surface and detect analytes, such as biological markers, remove analytes or other material, or deliver material. An example of this is shown in FIG. 1C. In this example, the patch 100 is urged against a subject's skin shown generally at 150, so that the projections 110 pierce at least the Stratum Corneum 160, and enter the Viable Epidermis 170.

In one example, this allows the projections 110 to contact targets of interest 180, allowing analytes therein to be detected, material to be delivered thereto, or material to be retrieved therefrom. Alternatively, the projections may merely be required to enter the Viable Epidermis 170, or dermis 190, without the need to contact any specific targets 180. This can be used to allow deliver material to, or target analytes in the subject's ISF. By configuring the projections with an appropriate length, and/or by applying the patch in a controlled manner, this allows the depth of projection penetration to be varied through the epidermis layer 170 and dermis 190. The projections 110 may also be adapted to enter a lower capillary layer, or other region of the subject, depending on the targets of interest.

In the example of FIG. 1C the targets 180 are provided in a single layer 181 with each target being within a layer, the layer being situation at an approximate depth $D_c$ below the Stratum Corneum 160. In this example, the layer height $h_{layer}$ is approximately equal to the diameter of the targets $d_c$, with the targets separated by a spacing $S_c$. However, alternatively the targets 180 can be dispersed throughout the Viable Epidermis 170, so that the target layer 181 will have a layer height $h_{layer}$ greater than that of the cell diameter, meaning cells can be provided at different depths. It would be appreciated by persons skilled in the art that in this instance the targets may therefore be Langerhans Cells, or the like. Additionally, the surface 150 includes undulations, resulting in a mean surface level 151 shown by dotted lines, with the patch base 120 resting against the surface 150 at a distance y above the mean level 151. These parameters regarding the location of the targets 180 and the patch 100 can be used to determine the preferred geometry of the projections 110, increasing the chance of analytes of interest being detected.

Figures 1D, 1E, 1F:
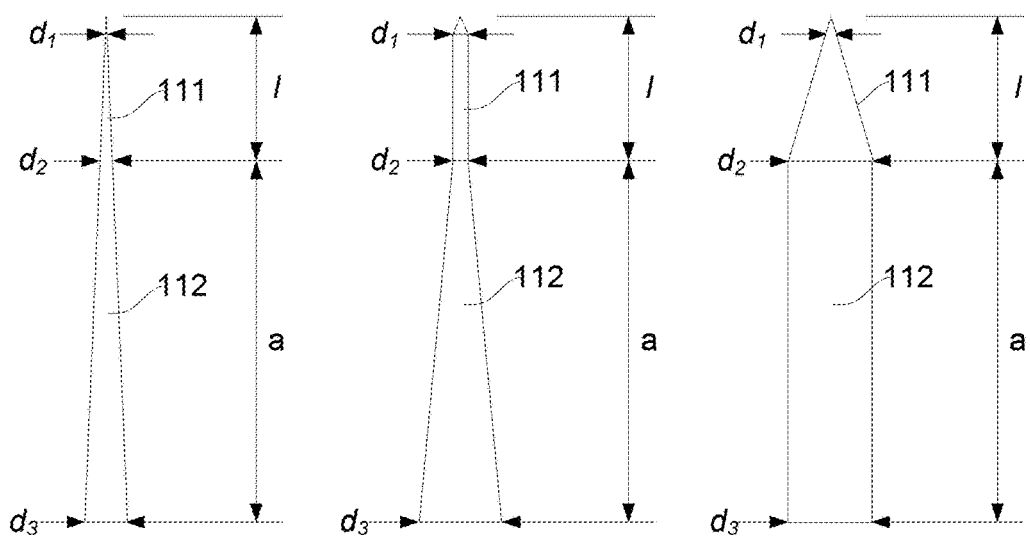
FIGS. 1D to 1F are schematic diagrams of examples of projections used in the device of FIG. 1A.

It will be appreciated that the projections can have a variety of shapes, and examples of suitable projection shapes are shown in more detail in FIGS. 1D, 1E and 1F.

In one example, the projection includes a targeting section 111, intended to target analytes, deliver material or stimulus, or extract material, and a support section 112 for supporting the targeting section 111. However, this is not essential, and a single element may be used.

In the example of FIG. 1D, the projection is formed from a conically shaped member, which tapers gradually along its entire length. In this example, the targeting section 111 is therefore defined to be the part of the projection having a diameter of less than $d_2$, but it will be appreciated that in this instance the distinction between targeting and supporting sections is arbitrary.

In FIGS. 1E and 1F, the structure of the projection may vary along its length to provide a defined targeting section 111 with a designed structure. In the example of FIG. 1E, the targeting section 111 is in the form of a substantially cylindrical shape, such that the diameter $d_1$ is approximately equal to the diameter $d_2$, with a tapered support section, such that the diameter $d_2$ is smaller than the diameter $d_3$. In contrast, in the example of FIG. 1F, the targeting section 111 is in the form of taper such that the diameter $d_1$ is smaller than the diameter $d_2$, with a cylindrical support section, such that the diameter $d_2$ is substantially equal to the diameter $d_3$.

In general, the support section 112 has a length a, whilst the targeting section 111 has a length l. The diameter of the tip is indicated by $d_1$, whilst the diameter of the support section base is given by $d_3$.

In use, the patch 100 can be used to allow analytes to be detected within specific targets within the body, the interstitial fluid (ISF) and/or the blood supply. The patch can also be used to detect analytes within any tissue within the subject, as well as deliver material or stimulus to, or sample, the subject. The configuration of the patch may therefore depend on the intended use.

Thus, for example, if the patch is configured so as to ensure that the projections contact specific targets such as cells, then it may be necessary to select a more specific arrangement of projections than if delivery is provided more generally to the blood. To achieve this, the device can be provided with a particular configuration of patch parameters to ensure specific targeting. The patch parameters can include the number of projections N, the spacing S between projections, the projection size and shape, as well as the surface roughness, or any other suitable parameter.

In one specific example, a patch having a surface area of approximately 0.16 cm$^2$ has projections provided at a density of between 1,000-30,000 projections/cm$^2$, and typically at a density of approximately 20,000 projections/cm$^2$. However, alternative dimensions can be used. For example, a patch for an animal such as a mouse may have a surface area of 0.32 to 0.48 cm$^2$, whereas as a patch for a human may have a surface area of approximately 1 cm$^2$. A variety of surface areas can be achieved by mounting a suitable number and arrangement of patches on a common substrate.

The projections 110 typically have a length that depends on the intended use. For example, in detecting analytes in the epidermis, the projections typically have a length of between 10 to 200 μm and typically less than 90 μm. However, the projection length could be less than 1000 μm for analytes in dermal layers, 600-800 μm for basal cells in the epithelium of the mucosa and approximately 100 μm for lung targets. It will also be appreciated that other configurations could also be used, allowing the projections to be used to target analytes in any epithelial or any other accessible surface of the subject. This could include internal surfaces such as organs/vasculature, with this being achieved by mounting the patches on endoscopes or the like.

In addition to projection length, the depth of projection penetration can be also depend on other variables, such as the manner in which the patch is applied, including the velocity, force and strain rate of the application, and other mechanical properties of the patch.

If distinct targeting section and support sections are provided, the targeting section typically has a diameter of less than 1 μm and more typically less than 0.5 μm. The length of the targeting section is typically less than 100 μm, less than 10 μm and typically less than 5 μm. The projection tips also typically have a radius of curvature in the region of 1 μm or less, although larger curvatures such as 5 μm, and smaller curvatures, such as below 0.5 μm may be used.

However, it will be appreciated that other dimensions and patch configurations may be used, and that the arrangements above are for the purpose of example only.

An example of apparatus for applying a patch to a subject, to deliver material to, retrieve material from, or detect analytes in the subject will now be described with reference to FIGS. 2A and 2B.

In this example, the patch is to be applied to a subject S and in particular to a part of the subject S such as section of tissue, shown generally at T. This can include a skin fold, or exposed skin area such as ear lobe, webbing between fingers/thumb, the cheek, mucosal sites, digits, or the like. However this is not essential and the patch may be applied to any part of a subject as will be apparent from the description below.

In this example, the apparatus 200 includes first and second opposable jaws 211, 212 movable between an open position shown in FIG. 2A and an engaging position shown in FIG. 2B. In the open position the jaws can receive at least part of the subject, in this case the tissue T. The jaws can then be moved to the engaging position, to thereby engage the tissue T, as shown in FIG. 2B.

The apparatus 200 also includes a patch support for supporting a patch shown generally at 100. In this example, the patch support is provided by a surface of the first jaw 211 such that when the jaws 211, 212 engage the subject, the patch 100 is urged against the subject by the first jaw 211.

However, alternative arrangements can be used, as will now be described with reference to FIGS. 3A to 3C.

In this example, the apparatus 300 again includes first and second opposable jaws 311, 312 movable between open and engaging positions as shown in FIGS. 3A and 3B. In this example, the patch support 313 is provided on a separate third jaw. In this instance after the jaws 311, 312 have engaged the tissue T the patch support 313 is urged towards the tissue T so that the patch 100 is applied to the tissue T. In one example, the patch 100 extends through an aperture provided in the first jaw 311, although this is not essential, and alternatively the patch may be applied offset from the first jaw 311. This arrangement can be used to allow the first jaw 311 to pre-stress, compress or tension the skin, prior to insertion of the patch, thereby making patch insertion more reliable and consistent, as will be described in more detail below.

Accordingly, it will be appreciated that the above described techniques provide a mechanism for applying a patch to a subject. In particular, in these examples, the apparatus includes jaws movable between open and engaging positions allowing at least part of a subject to be engaged by the jaws. With the jaws engaged, the patch is applied to the subject.

In one example, the apparatus is for applying the patch to thereby at least partial control at least one application parameter, the at least one application parameter relating to the application of the patch, and including parameters such as the force or velocity with which the patch is applied. If the patch is provided on one or both of the jaws, the application parameter(s), such as the force or velocity with which the patch is applied, will vary depending on the closing of the jaws. Accordingly, the closing mechanism used will typically be arranged to allow a desired application force or velocity to be achieved.

In another example, the patch can be provided on a separate member or arm which then engages the tissue, allowing the application parameters to be controlled independently of the closing of the jaws. This can be used to allow greater control over the application parameters, as well as allowing the skin or tissue to be pre-tensioned before the patch is applied to the subject, as will be described in more detail below.

In either case, the apparatus permits application with different velocities and/or forces, which can help ensure adequate penetration of the patch projections. In particular, the surface of the skin is resilient, and will therefore tend to resist penetration of the skin by the projections. In one example, the projections typically have a length in the range 10 to 200 μm, which is sufficiently short to allow the skin to deform and resist penetration if the patch is not applied with sufficient force and/or velocity. Additionally, skin properties can vary between people in the population from age, sex, chemical damage etc., meaning it is desirable for the apparatus to remove as much variability as possible in respect of the application process. By allowing the application parameters to be adjusted by controlling the closure of the jaws, or the separate application of the patch, this allows the apparatus to assist in ensuring adequate penetration of the projections.

In particular, the velocity of patch application corresponds to the velocity at which the patch is moving when the patch hits the surface of the tissue T. The patch velocity has a direct bearing a strain-rate effect in the mechanical properties of the skin, and therefore utilising a sufficiently high velocity can help ensure consistent penetration. In one example, a velocity of below 8 m/s is used, with the velocity more typically being in the region of 1-3 m/s, although this may vary depending on the nature of the patch and the projections thereon, and accordingly, lower velocities may be more appropriate depending on the patch configuration. Additionally, the force can be used in a quasi-static application, where the patch impacts on the tissue surface with minimal velocity, and penetration of the projections is ensured by maintaining a force on the patch. It will be appreciated that a combination of these techniques may also be used.

The application parameters that are selected will depend on a number of factors, such as the location of targets within the subject, and patch parameters, such as the number of projections, the spacing between projections, the projection size and shape, as well as the surface roughness. Thus, for example, if the patch is to be used to deliver material to a greater target depth within the subject, then the application velocity may need to be greater than if shallow delivery is required. Similarly, the ability of the projections to penetrate the tissue surface will also depend on the geometry of the projections, so that for example, narrow projections may penetrate more easily than wide or stepped projections. Furthermore, longer projections may require a greater delivery velocity, whereas a patch having a lower density of projections may require a lower velocity.

Accordingly, in one example, the application parameters may be determined based on the patch parameters and the intended use of the patch. However, this is not essential, and in general, suitable application parameters can be determined that allow a wide range of patch geometries and intended usages to be accommodated.

A number of specific examples of apparatus for applying patches to a subject will now be described in more detail.

In the example of FIGS. 4A to 4D, the apparatus 400 includes first and second arms 401, 402 having first ends defining the jaws 411, 412. The arms include pivot mounts 421, 422 which are coupled together via a pivot 430. A resilient member, such as a spring 431, is coupled to the pivot 430 and engages the arms 401, 402 urging the jaws 411, 412 to be biased towards a closed position, shown in FIGS. 4A and 4B.

The patch 100 may be mounted on one or more of the jaws 411, 412, with a patch being shown mounted on the first jaw 411 in this example. Mounting may be achieved in any one of a number of manners, and in one example, this is achieved using an adhesive, such as a double sided adhesive tape. The adhesive tape may be adapted to release upon the application of a force, such as a shear force, thereby allowing the patch 100 to be removed and the apparatus 400 reused. Alternatively other suitable mounting techniques, such as the use of a socket adapted to receive the patch 100 using a friction fit, interference fit, or similar, can be used.

Figure 4A:
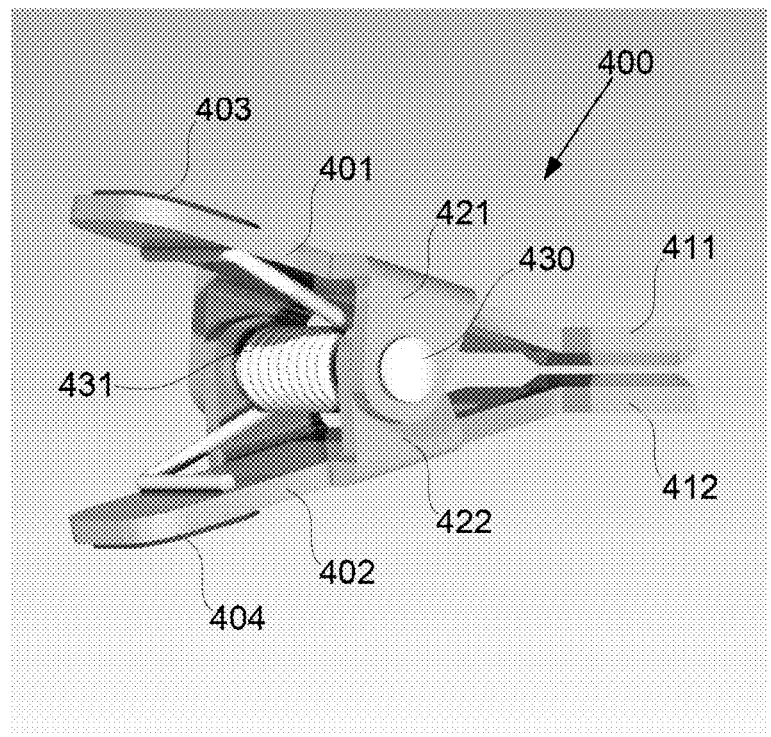
FIGS. 4A to 4D are schematic diagrams of a first specific example of apparatus for applying a patch to a subject.
Figure 4B:
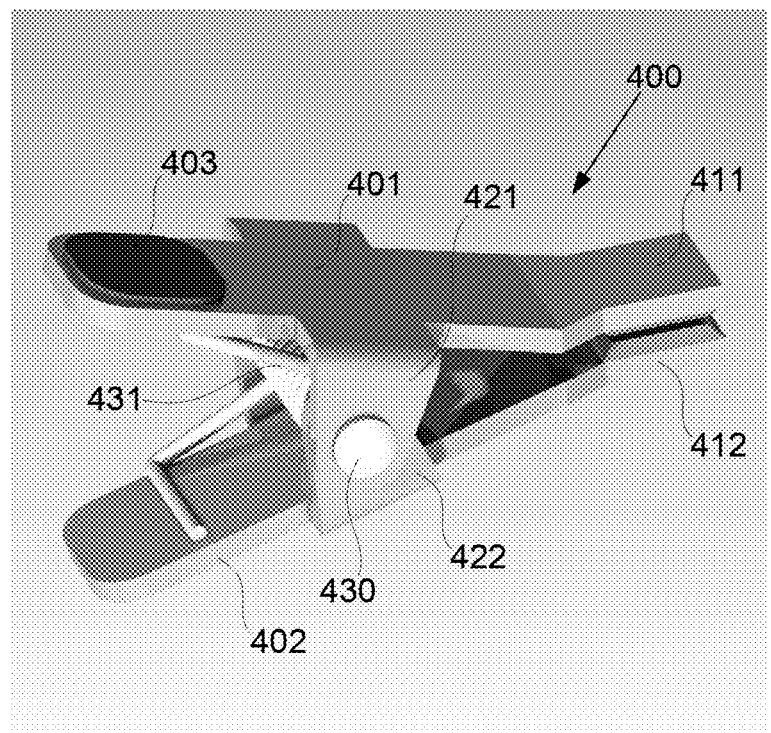
Figure 4C:
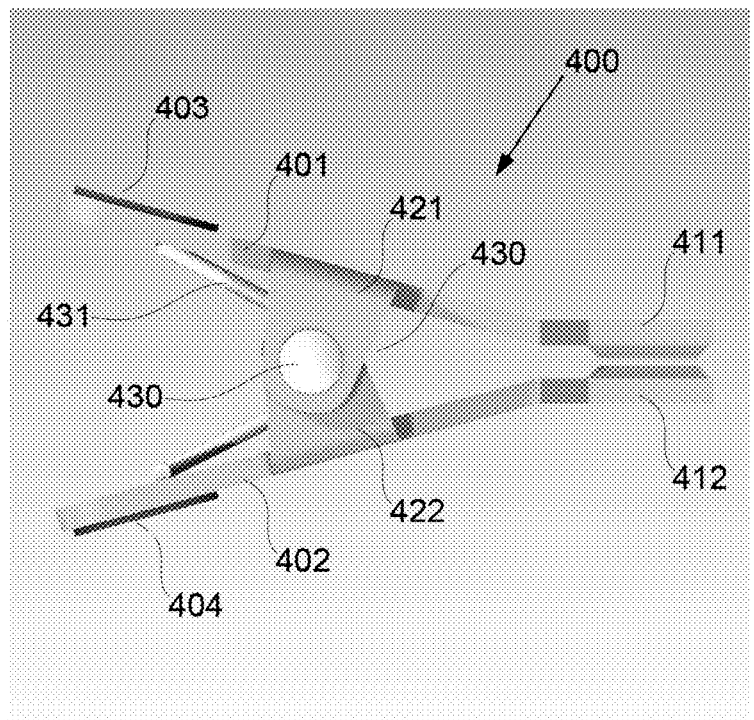
Figure 4D:
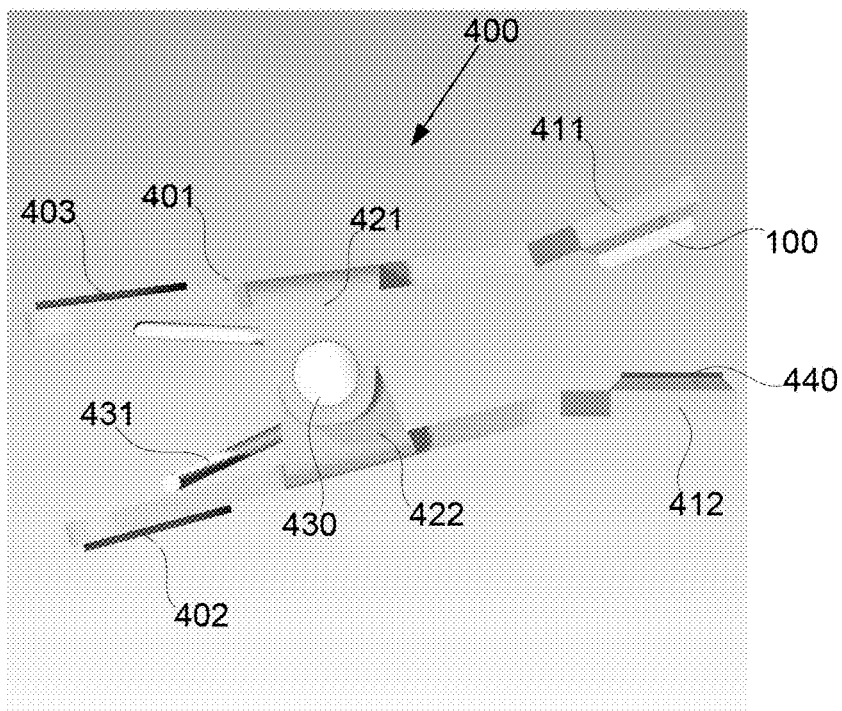

In one example, the arms include second ends defining grips 441, 442 allowing a user to apply a force to the arms 401, 402 thereby moving the arms 401, 402 to the open position shown in FIG. 4D. It will be appreciated by a person skilled in the art that when a part of the subject, such as tissue T, is positioned between the jaws and the jaws are released, the spring 431 will urge the jaws 411, 412 towards the closed position. However, with tissue T present between the jaws 411, 412, the jaws 411, 412 will engage the tissue and be held in an engaging position. Accordingly, in this example, the jaws have a closed position in addition to the engaging position, although this is not essential.

In the event that a patch is mounted on only one of the jaws 411, 412, the other jaw 412, 411 may include a resilient pad, for example made of rubber or the like. This can be used to prevent damage occurring to the patch 100 when the jaws are in the closed position, as well as increasing comfort to a subject in use.

In one example, in use, the jaws 411, 412 are fully opened, before the tissue T is provided between the jaws 411, 412. The jaws 411, 412 are then released, allowing the jaws 411, 412 to engage the tissue T under action of the spring 431. Releasing can be achieved by releasing the grips 441, 442. Alternatively, the arms 401, 402 can be held in the open position by a stop, which is then removed to allow the jaws 411, 412 to close. This can be achieved by insertion of the part of the subject, as will be described in more detail below with respect to FIGS. 12A to 12C.

In any event, releasing the jaws 411, 412 from the open position allows the tension in the spring to be used to urge the jaws 411, 412 into the engaging position, thereby controlling the application parameters, and in particular the force and/or velocity with which the patch contacts the subject's skin. This can be used to ensure penetration of the skin by the projections. It will be appreciated from this that the spring tension and strength will typically be selected depending on the circumstances in which the patch is to be used.

In this regard, the application parameters required will typically be determined based on factors such as the skin to which the patch is to be applied, as well as patch parameters, such as the size, geometry and spacing of the projections on the patch. Once determined, the require application parameters can be used to determine required spring properties, thereby allowing the apparatus to be configured for use. In one example, this would be achieved during a design process, with the spring configuration being fixed in the final device. However, this is not essential, and a spring having a variable tension could be used allowing the application parameters to be adjusted prior to use, for example depending on the patch to be used, and/or the nature of the subject to which the patch is applied.

Additionally, the spring tension can be used to ensure that the patch is retained in place with a predetermined force for a required application period, which is typically in the order of a few seconds. This therefore allows the apparatus 400 to not only apply the patch, as is the case of many prior art devices, but also retain the applied patch in place for a required time period.

Figure 5A:
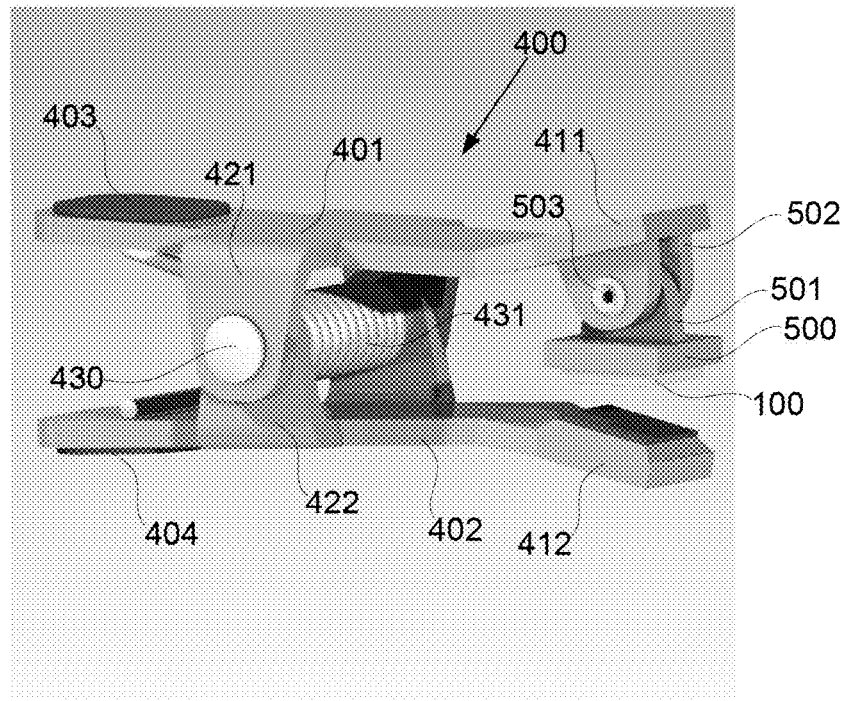
FIGS. 5A to 5C are schematic diagrams of a second specific example of apparatus for applying a patch to a subject.
Figure 5B:
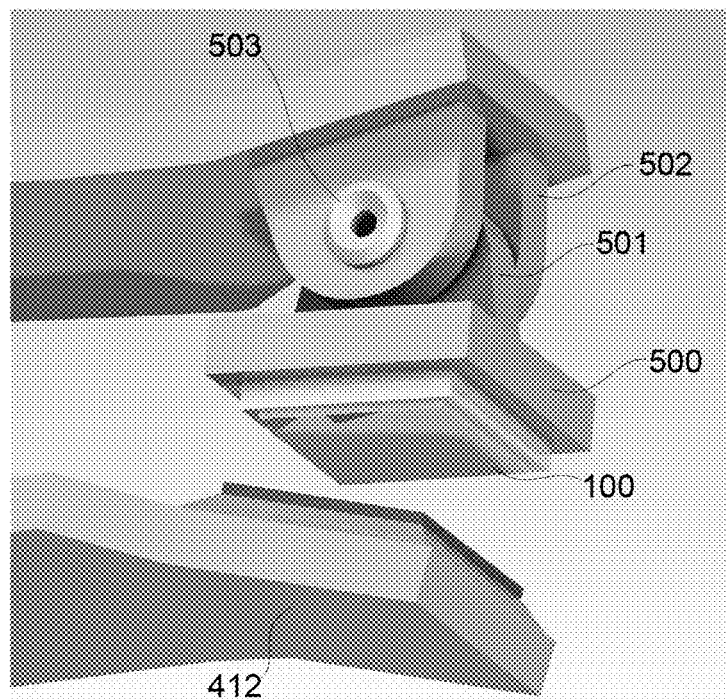
Figure 5C:
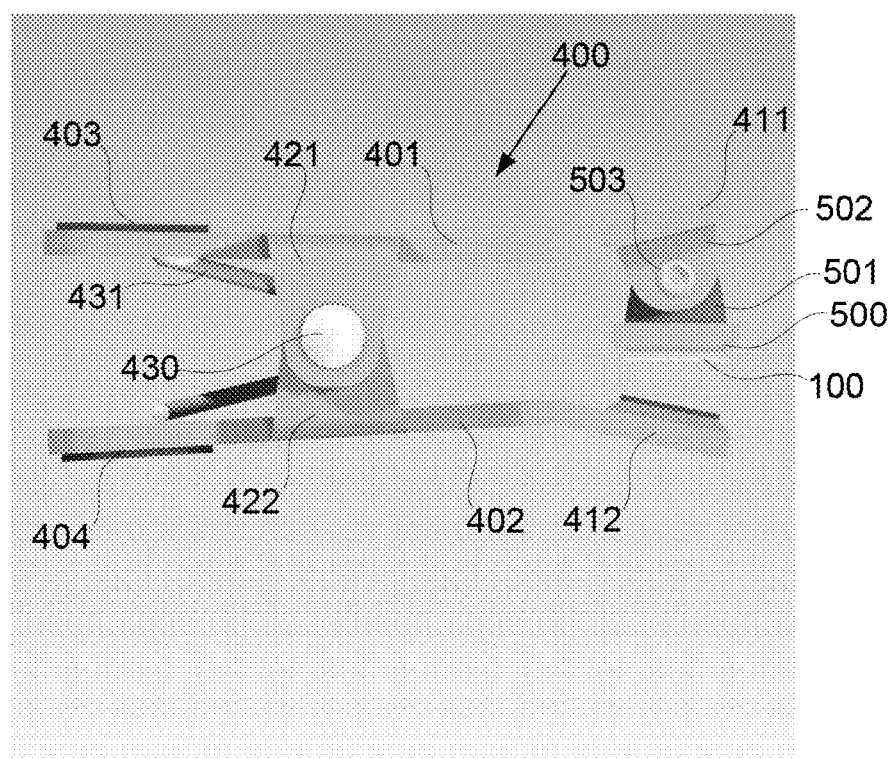

A second specific example apparatus, which is a modified version of the apparatus of FIGS. 4A to 4D is shown in FIGS. 5A to 5C.

In this example, instead of the patch being attached directly to the first jaw 411, the patch is attached to a patch mount 511 having a pivot support 512. A corresponding pivot support 513 is provided on the first jaw 411, allowing the patch mount 511 to be pivotally coupled to the first jaw 411. This can be used to help align the patch 100 parallel to the surface of the tissue T to which the patch is being applied. In particular, if the patch is aligned offset from parallel, one edge of the patch 100 will engage the skin before the other side, causing the patch mount to pivot and align the patch in a parallel manner during the application. This further helps even penetration of the projections into the subject.

A third specific example of apparatus for applying a patch will now be described with reference to FIGS. 6A to 6D.

In this example, the apparatus 600 includes first and second arms 601, 602 having respective first ends defining jaws 611, 612. In this example, second ends of the arms 601, 602 are coupled via a connector shown generally at 630. The connector is arranged to allow relative movement of the first and second arms 601, 602, so that the arms can be moved between open and engaging positions.

In one example, the connector 630 is made of a flexible material and is integrally formed with each of the first and second arms 601, 602 such that the arms 601, 602 and the connector 630 comprise a single piece of material. In one example, the arms 601, 602 and the connector 630 are made of a resilient, lightweight and tough material. Whilst any suitable material may be used, typically the material is metal, plastic, composite or polymer material such as PVC (Polyvinyl Chloride), or the like. It will be appreciated that this allows the arms 601, 601 and connector 630 to be manufactured utilising an injection moulding or other similar process, making the apparatus cheap and easy to manufacture.

In this example, the arms are naturally biased towards the open position shown in FIGS. 6A to 6D. In this example, the apparatus 600 can include a retaining system in the form of a clip having two cooperating clip portions 631, 632. The clip portions 631, 632 are designed so that the clip portion 631 acts as a plug, which is inserted into and engages the clip portion 632, which in this case acts as a socket. The engagement is typically achieved utilising a friction or interference fit allowing the clip to be selectively engaged or disengaged, although this is not essential, and any suitable arrangement may be used. In any event, the retaining system allows the jaws 611, 612 to held in the engaging position in use.

It will be noted that in this arrangement, there is no closed position for the jaws 611, 612, with the jaws being held apart even in the engaging position. This can be advantageous as it reduces the likelihood of damage that could arise if patches 611, 612 on each of the jaws were urged together during transport, manufacture or the like.

Figure 6A:
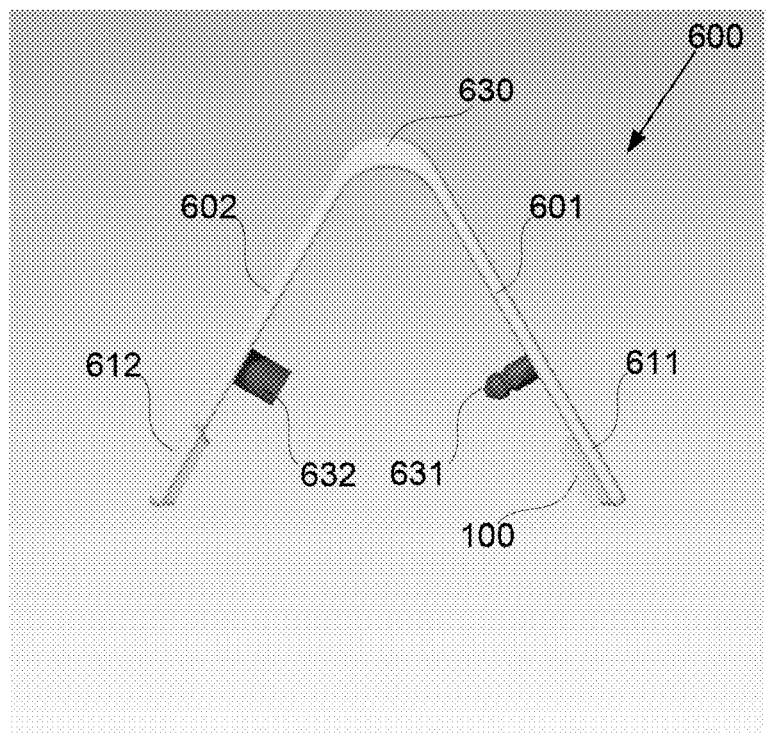
FIGS. 6A to 6D are schematic diagrams of a third specific example of apparatus for applying a patch to a subject.
Figure 6B:
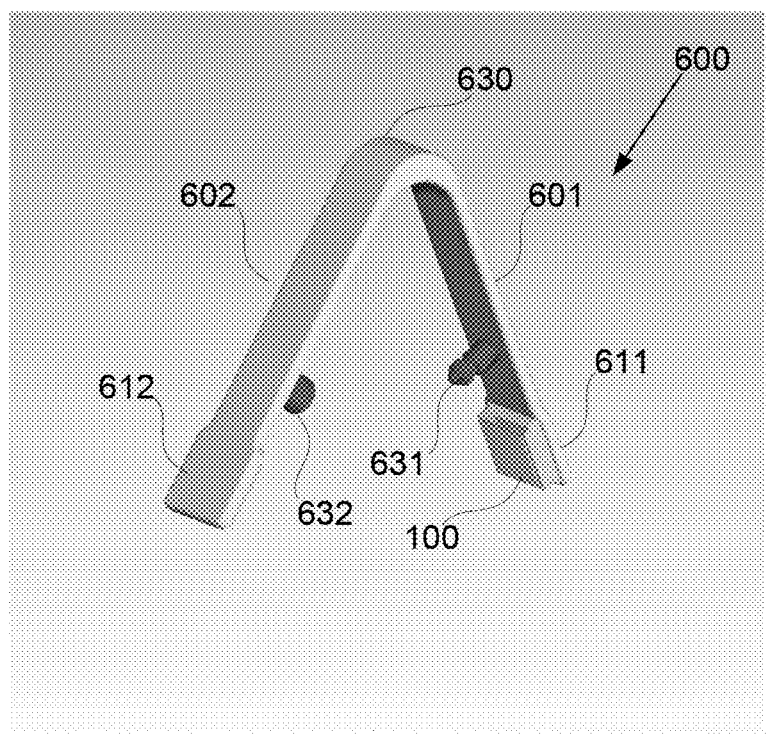
Figure 6C:
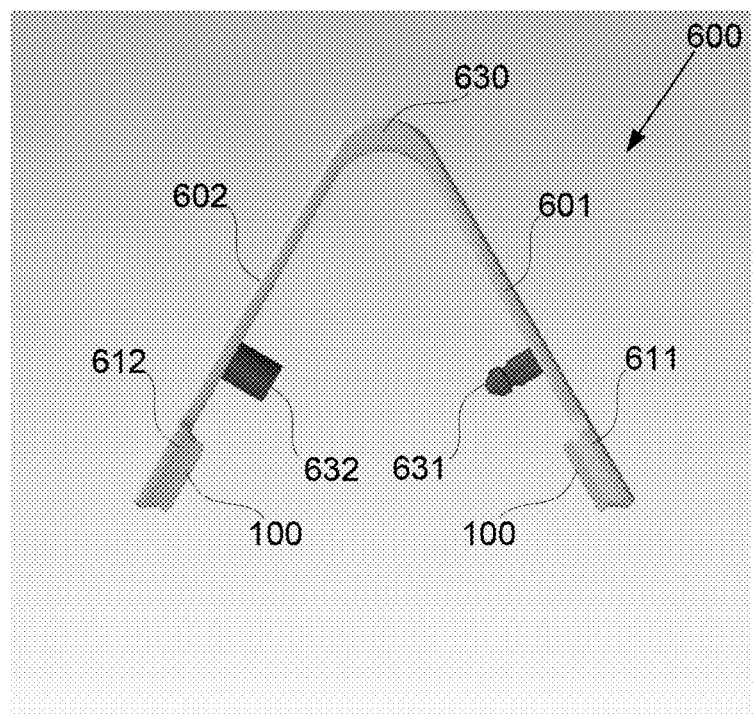
Figure 6D:
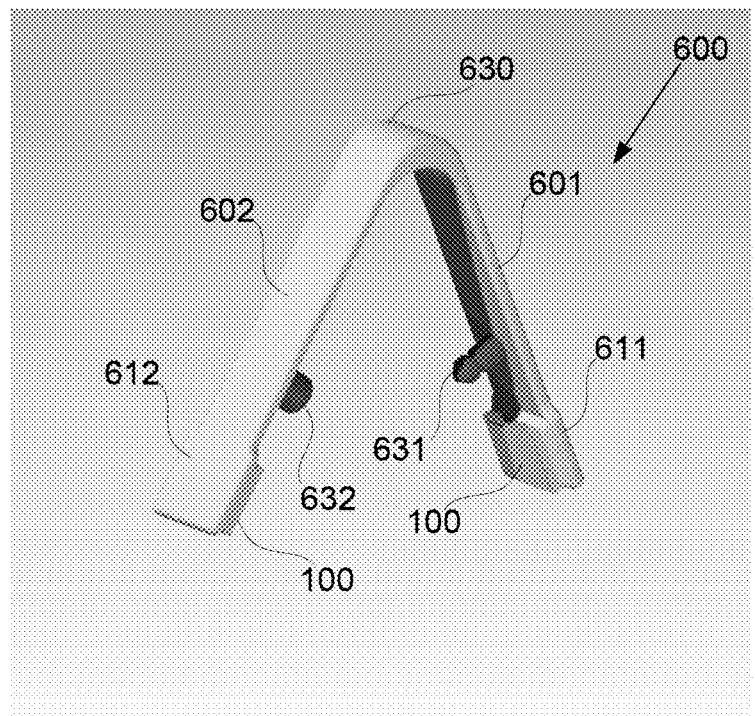

A patch 100 may be mounted on one of the jaws 611, as shown in FIGS. 6A and 6B, or alternatively may be provided on both jaws 611, 612, as shown in FIGS. 6C and 6D. In either case, in use an operator will release the clip 631, 632 allowing the arms 601, 602, and hence the jaws 611, 612 to be urged into the open position under action of the connector 630. Once the part of the subject is provided between the jaws 611, 612, the arms 601, 602 can be urged together so that the clip portions 631, 632 engage and retain the apparatus 600 in the engaging position.

It will be appreciated that in contrast to the examples described above with respect to FIGS. 4 and 5, in this example engagement of the patch with the subject can be manually controlled, as opposed to being controlled by the spring or other biasing member. This can therefore lead to reduced control over the application parameters, such as the force and velocity with which the patch is urged against the subject, with this largely being controlled by the pressure applied to the arms 601, 602 by the operator. Whilst this is acceptable in many circumstances, it can be desirable to ensure a greater degree of consistency in the application parameters, and accordingly a separate applicator device can be used to control the closure of the jaws, thereby ensuring consistent patch application with the above described example.

A further possibility is to use a different application technique, as will now be described with reference to a fourth specific example shown in FIGS. 7A to 7F.

In this example, the apparatus 700 includes first and second arms 701, 702 coupled together via a connector 730. The first and second arms 701, 702 define first and second jaws 711, 712. The arms 701, 702 are also coupled to respective clip portions 731, 732 which engage in a manner similar to that described above with respect to the clip portions 631, 632 in the example above.

In this example, instead of mounting a patch on a respective one of the jaws 711, 712, the patch 100 is coupled to a third arm 703, having a third jaw 713. The third arm 703 is coupled to the first and second arms 701, 702, typically by attaching the third arm 703 to the connector 730, using a coupling 753. However, this is not essential, and the first, second and third arms can be integrally formed as a single piece.

Figure 7A:
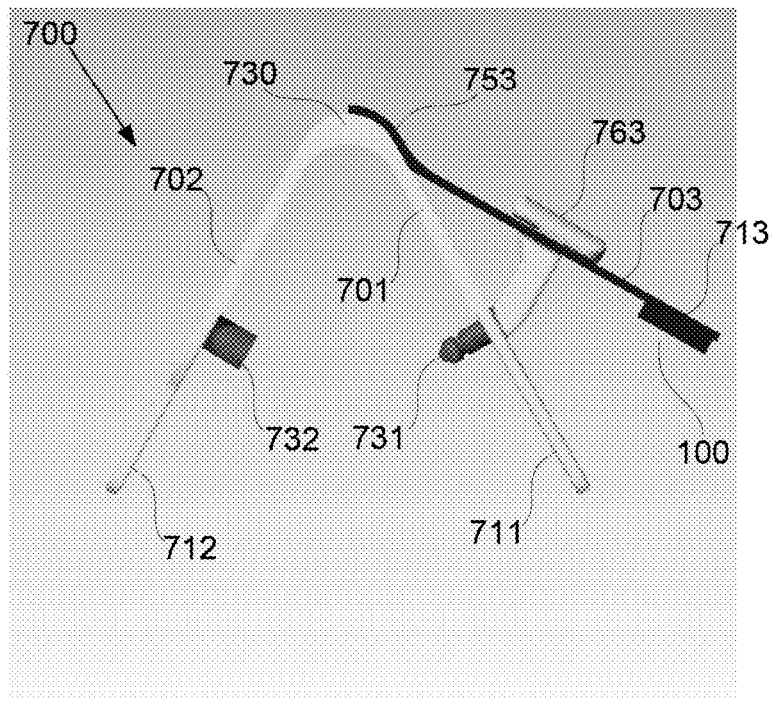
FIGS. 7A to 7F are schematic diagrams of a fourth specific example of apparatus for applying a patch to a subject.
Figure 7B:
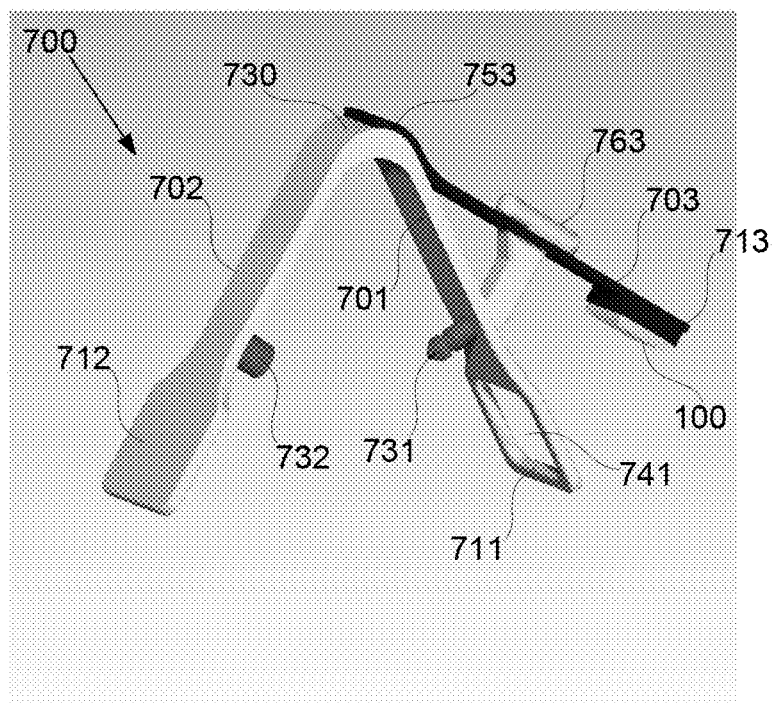
Figure 7C:
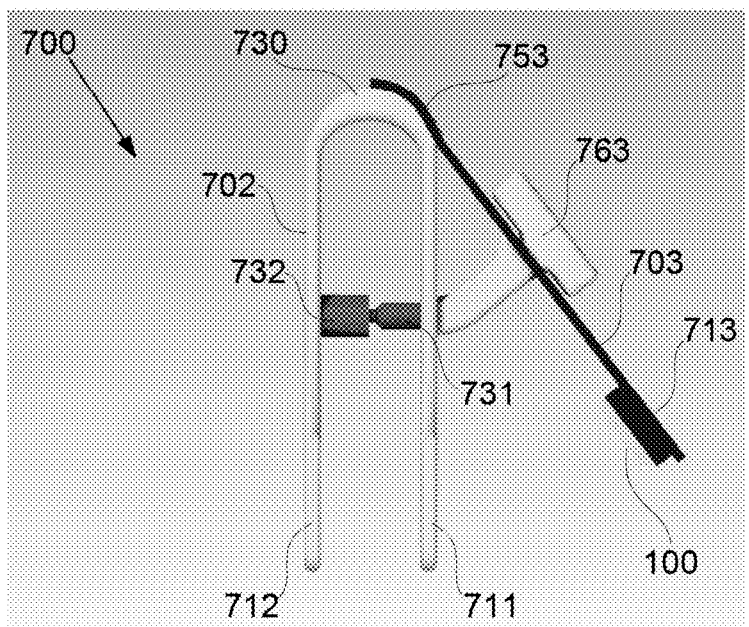
Figure 7D:
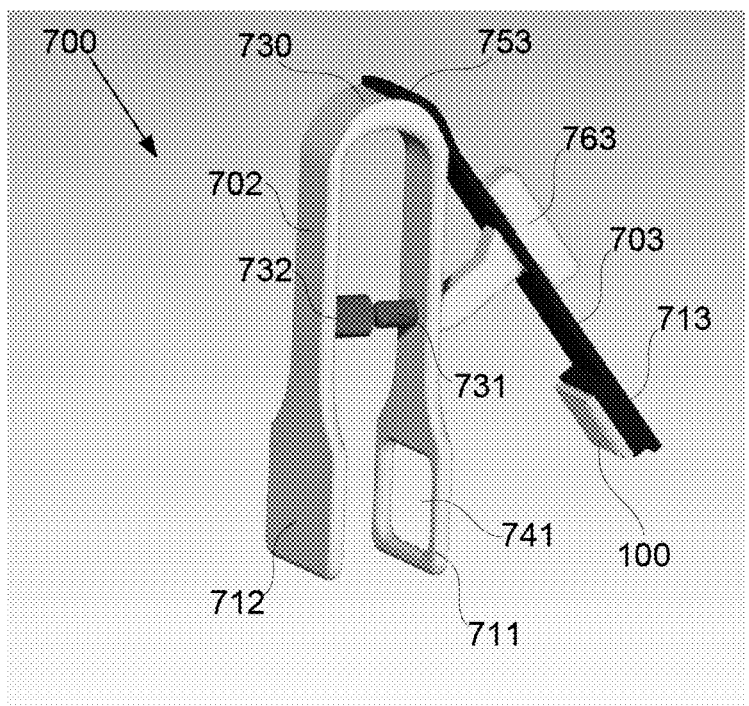
Figure 7E:
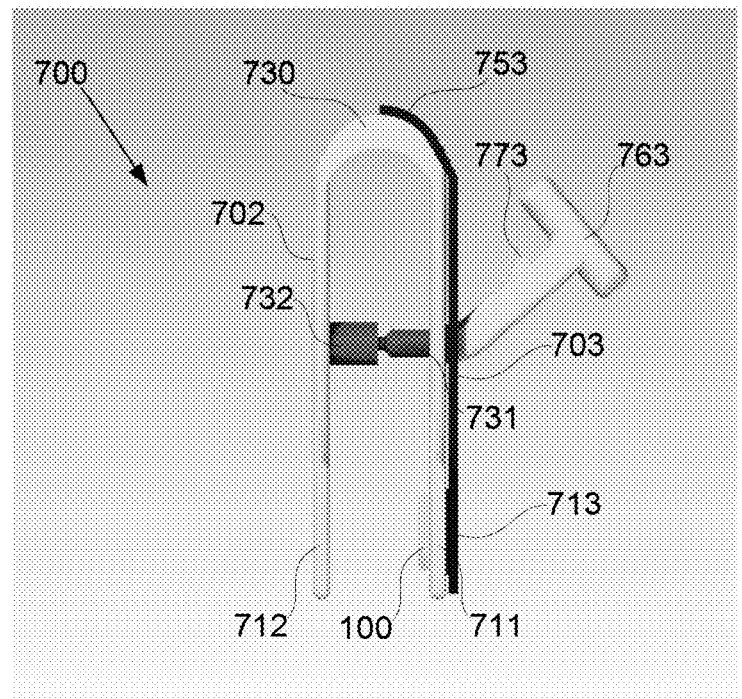
Figure 7F:
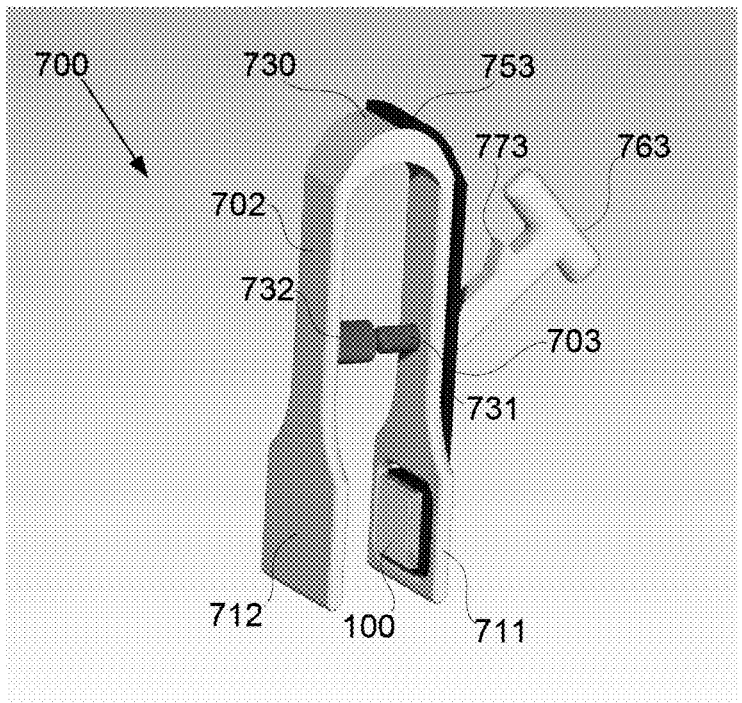
Figure 8A:
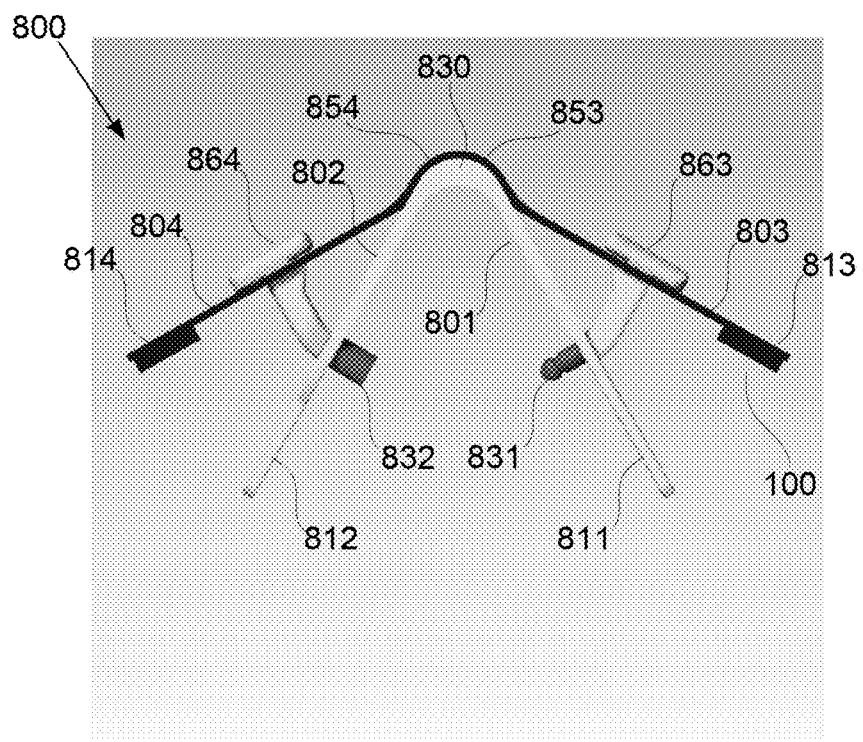
FIGS. 8A to 8F are schematic diagrams of a fifth specific example of apparatus for applying a patch to a subject.
Figure 8B:
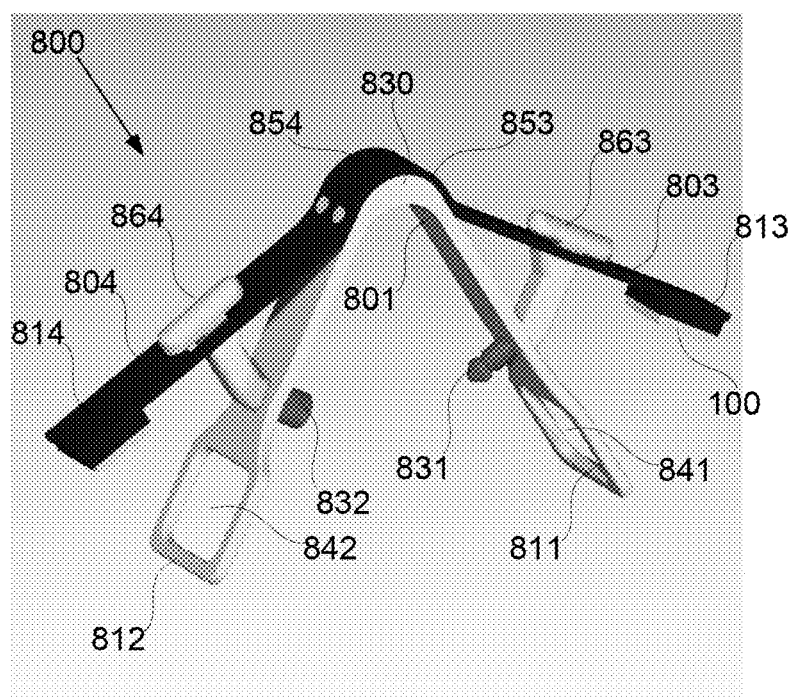
Figure 8C:
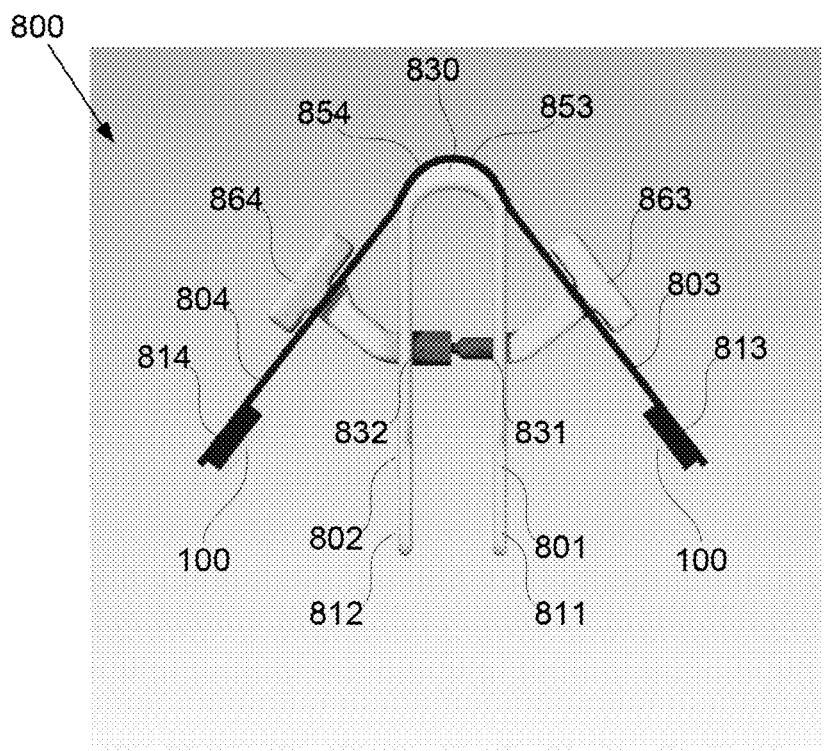
Figure 8D:
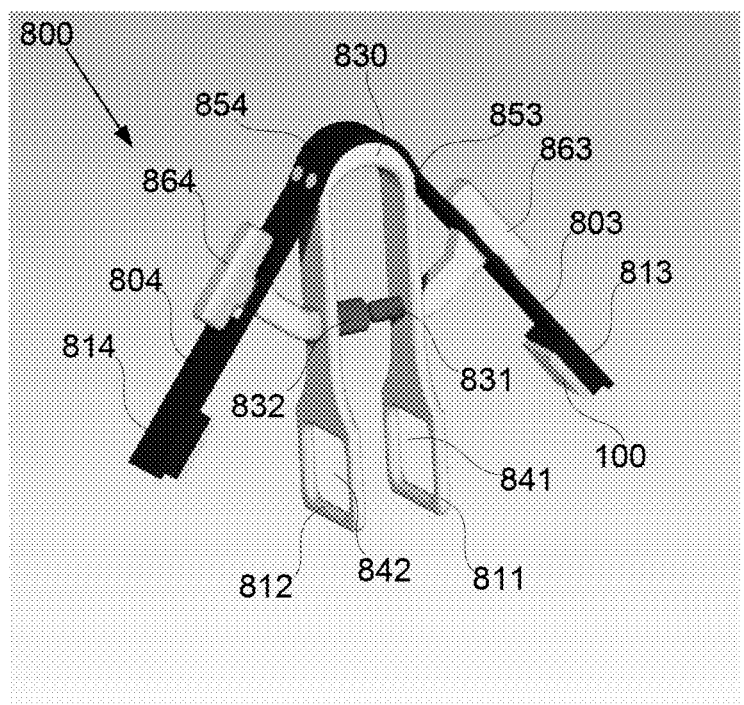
Figure 8E:
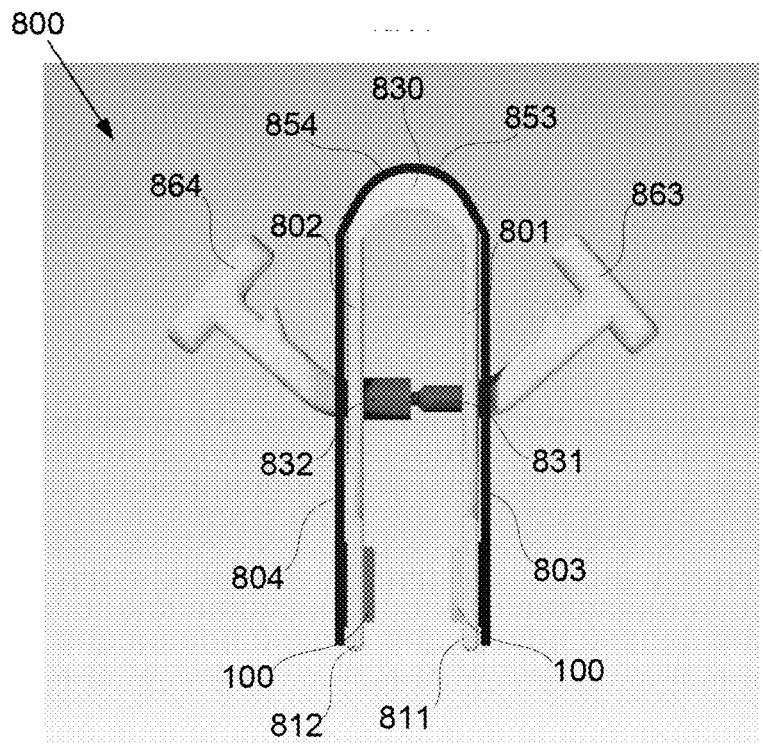
Figure 8F:
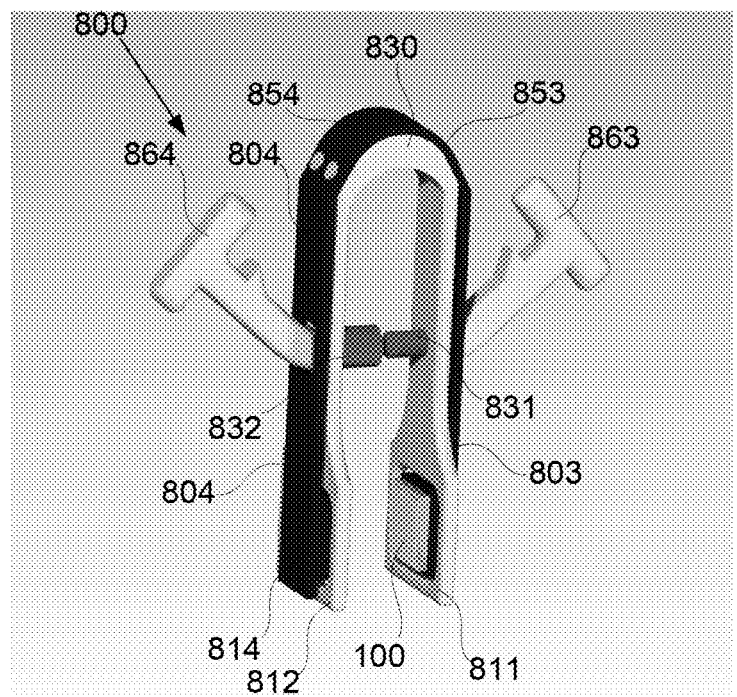

In any event, the third arm 703 and/or the coupling 753 are arranged to bias the third arm towards an engaging position shown in FIGS. 7E and 7F. This may be achieved in any suitable manner, but in one example is achieved by manufacturing the third arm 713, and/or the coupling 753, from a resilient material such as plastic, metal, or the like.

To allow the third arm 703 to be provided in the open position shown in FIGS. 7A to 7D, a restraining clip 763 is provided, which in this instance is coupled to the first arm 701. The restraining clip 763 includes a projection 773 that engages the third arm 703, thereby retaining the third arm 703 in the open position when not in use. Upon movement of the retaining clip 763, the projection disengages the third arm 703, allowing the third arm 703 to be urged towards the engaging position.

In this example, the first jaw 711 also includes an aperture 741 which aligns with the patch 100 mounted on the third jaw 713, allowing the patch 100 to extend therethrough, when in the engaging position. The aligning aperture 741 can be used to compress the skin to ensure a more rigid material into which the projections will enter, facilitating penetration, with control of compression being provided by an urging means, such as a flexible member, tension spring, or the like, as will be described in more detail below.

In use, the clip portions 731, 732 are initially released, allowing the arms 701, 702 to move to the open position shown in FIGS. 7A and 7B, with tissue then being positioned between the jaws 711, 712. During transport, or following a prior use, all the arms 701, 702, 703 may initially be the engaging position, and accordingly, it may also be necessary to urge the third arm 703 into the open position shown in FIGS. 7A and 7B.

The arms 701, 702 are then urged together so that the clip portions 731, 732 engage, with the tissue being engaged by the jaws 711, 712, whilst the third arm 703 remains in the open position, as shown in FIGS. 7C and 7D. It will be appreciated that this causes tissue to be gripped by the jaws 711, 712 so that the patch may be subsequently applied. In this regard, the use of the aperture 741 allows a force to be applied to tissue of the subject, thereby ensuring that the skin or other tissue within the confines of the aperture 741 is stretched, compressed, or pre-stressed. This assists in presenting a consistent and/or substantially flat surface for the subsequent application of the patch 100, which can further help ensure consistent application.

The magnitude of the applied force can be controlled based on the use of a biasing mechanism, such as a spring, flexible or resilient member, or another engaging part of the device, which is adapted to urge the aperture 741 against the tissue. Thus, for example, the connector 730 could be made from a flexible elastic or otherwise resilient material, allowing the jaws 711, 712 to be urged together by a restoring force induced when the jaws 711, 712 are urged apart. However, other arrangements can be used, such as by having the connector 730 include a pivot, with a spring being used to urge the jaws 711, 712 together.

Accordingly, it will be appreciated that the aperture 741 can act not only to provide alignment ensuring that the patch 100 impinges on the region of skin within the aperture 741, but also to allow the skin to be stretched and/or pre-stressed, thereby providing an optimum surface for penetration of the patch projections.

Finally, the retaining clip 763 is released and in particular, the retaining clip 763 is moved so that the engaging projection 773 disengages from the third arm 703, thereby allowing the third arm 703 to move towards the engaging position. At this point, the patch 100 extends through the aperture 741 and engages the subject. It will be appreciated from this that the application parameters, including the application force and/or the application velocity will be controlled based on the resilience of third arm 703 and/or the coupling 753, thereby helping ensure consistent application parameters are used.

A fifth specific example arrangement will now be described with reference to FIGS. 8A to 8F.

In this example, reference numerals are increased by 100 to represent similar components to the example of FIGS. 7A to 7F. It will be appreciated from this, for example, that the apparatus 800 also includes first, second and third arms 801, 802, 803 that function in a manner similar to the first, second and third arms 701, 702, 703 described above.

In addition, in this example, a fourth arm 804 is provided having a fourth jaw 814 for receiving a patch 100. In this example, the patch 100 provided on the fourth jaw 814 is adapted to extend through an aperture 842 provided in the second jaw 812, so that the patch 100 on the fourth arm 804 can be deployed in a manner similar to the patch 100 on the third arm 803.

Accordingly, this arrangement allows two patches to be independently applied to the subject without overtly increasing the size of the apparatus. It will also be appreciated that this can be advantageously used to allow different application parameters to be achieved, for example by having differential resilience for the third and fourth arms 803, 804. This can be used to allow a range of different application parameters to be provided for in a single apparatus, which in turn can be used to ensure successful delivery of patches across a wide variety of subject skin types, application locations, or the like.

It will be appreciated that the ability to apply two different patches independently allows two different vaccines to be applied at the same time. For example, two patches could be used, each having a respective vaccine, allowing multiple vaccines to be administered in a single procedure. Additionally/alternatively, the patches may be arranged to be applied to different types of tissue surface. For example, the patches could be applied to the cheek, with one patch being for application to the buccal mucosa and one for application to the skin. Thus, it will be appreciated that patches can contain different patches and/or be configured for application to different tissue types.

A number of further variations will now be described.

As described above, the ability of patch projections to penetrate tissue may depend on the patch parameters, such as the projection size and shape. An example of this will now be described with reference to FIGS. 9A and 9B.

Figure 9A:
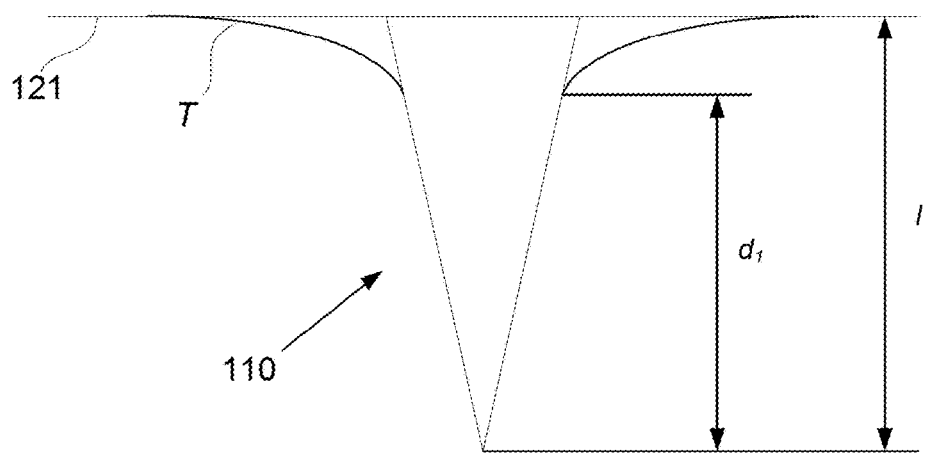
FIG. 9A is a schematic diagram of the penetration of tissue by a first example projection.
Figure 9B:
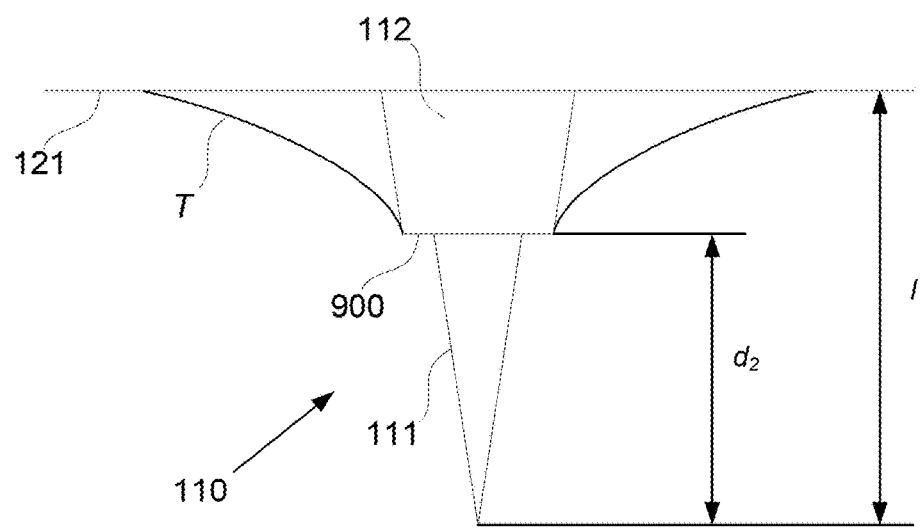
FIG. 9B is a schematic diagram of the penetration of tissue by a second example projection.

In the example of FIG. 9A, the projection 110 is a continuously tapered projection, such that the outer surface of the projection is conically shaped. In this instance, if the patch is applied with a sufficiently high velocity the projection 110 will tend to penetrate until the tissue surface T nears the patch substrate 120. As shown in this example, the skin typically deforms in a region immediately surrounding the projection 110, with the skin bowing away from the patch surface 121, so that the depth of penetration $d_1$ is less than the length of the projection l. However, if the application velocity is not sufficiently high, the projection will only penetrate partially, with the degree of difference between the depth of penetration $d_1$ and the length of the projection l depending on the application velocity. As a result, this can lead to variations in the depth of penetration in use.

Accordingly, in one example, the projections are shaped so as to limit the depth of penetration of the projections to thereby allow a consistent depth of penetration to be achieved. Any suitable form of shaping may be used, but in one example, the projections 110 have a stepped configuration an example of which will now be described with reference to FIG. 9B.

In this example, the projection 110 includes a targeting section 111 and a support section 112. The supporting section 112 has a greater diameter than the targeting section 111, thereby defining a step 900 between the targeting and supporting sections. In this example, upon the step meeting the tissue surface T, the step 900 presents a flat annular surface to the tissue surface T, thereby preventing further penetration. As a result, as long the application velocity is sufficiently high to allow penetration of the projection 110, the projection will penetrate to a depth $d_2$, which corresponds to the length of the targeting section 111. Accordingly, the arrangement of FIG. 9B can help ensure a consistent penetration depth based on the geometry of the projections, thereby allowing a degree of variation in the application velocity without adversely affecting projection penetration.

An example of an apparatus for applying and oscillating patch will now be described with reference to FIGS. 10A and 10B.

Figure 10A:
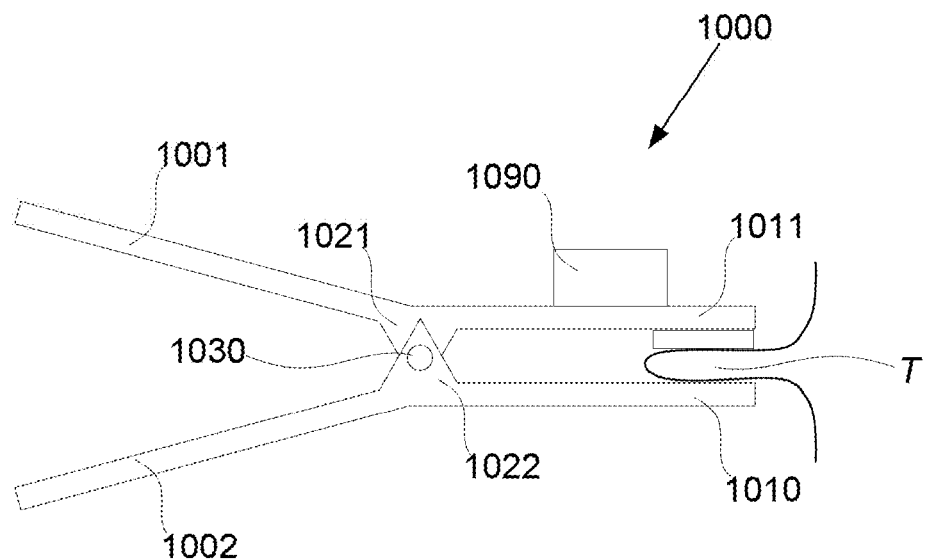
FIGS. 10A and 10B are schematic diagrams of examples of apparatus for applying and oscillating a patch.
Figure 10B:
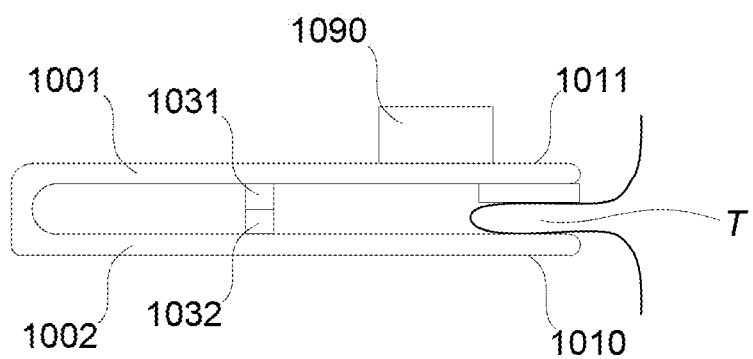

In the example of FIG. 10A, the apparatus 1000 includes first and second arms 1001, 1002, having respective jaws 1011, 1012. The arms are connected via pivot mounts 1021, 1022 and a pivot 1030, in a manner similar to that described above with respect to the apparatus 400. The arrangement shown in FIG. 10B is similar to that of FIGS. 6A to 6D, and therefore includes a connector 1030 and clip portions 1031, 1032.

In both cases, the apparatus includes an oscillator 1090 for oscillating one of the jaws 1011. The oscillator 1090 will typically be adapted to vibrate, with vibrations being transmitted along the arm 1001 to thereby oscillator the jaw 1011. Accordingly, it will be appreciated that the oscillator 1090 can be any suitable device for causing vibrations, such as a motor with an offset cam, wind-up device, or the like.

By oscillating the jaw 1011, this will cause small amounts of movement of the projections 110 within the subject, resulting in relative movement between the tissue T and the projections 110. The apparatus 1000 is typically configured so that the movement does not result in projections exiting the tissue T, and accordingly, the magnitude of the oscillation is typically smaller than the height of the projections 110.

In the event that the projection 110 is coated to deliver material to the subject, relative movement of the projection and tissue creates a shear force that can assist in dislodging the coating, thereby maximising the amount of material delivered to the subject. Similarly, if the projection 110 is being used to recover a sample, relative movement will assist in improving wettability of the projections 110, thereby improving the ability of the patch to extract a sample from the subject.

It will be appreciated that the use of an oscillator can also be implemented with an arrangement of apparatus similar to that shown in FIGS. 7 and 8.

As described above, the patch can be used to deliver a material to or retrieve material from a subject. In delivering material to a subject, the material may be pre-coated onto the patch, for example using a dry coating method. However, this is not essential, and in some circumstances it is desirable to be able to coat the patch shortly before use. Similarly, in the case of retrieving material from the subject, it can be desirable to allow the retrieved material to be stored for subsequent analysis, or combined with an indicator material to allow an indicator test to be performed.

In each of these cases, this may be performed by insertion of the patch into a suitable material either prior to or post application. Whilst this can be performed when the patch is not attached to the apparatus, as an alternative, the apparatus can include a well for storing material. An example of this is shown in FIGS. 11A to 11C.

In this example, the apparatus 1100 includes first and second arms 1101, 1102, having respective jaws 1111, 1112. The arms are connected via pivot mounts 1121, 1122 and a pivot 1130, in a manner similar to that described above with respect to the apparatus 400, although it will be appreciated that arrangements similar to those described in FIGS. 6 to 8 may also be used.

In any event, in this example, the patch 100 is mounted to a first jaw 1111, with a well 1120 being provided on the second jaw 1112. In one example, the well includes a housing 1130 defining a cavity 1140 optionally containing a substance 1150. A sealing film 1160 may also be optionally provided to assist in retaining the substance within the cavity. The substance can include a reagent for use in an indicator test, a material for delivery to the subject, or a solution for storing a retrieved sample.

In this arrangement, when the jaws 1111, 1112 are in a closed position, the projections 110 extend into the substance 1150. Accordingly, in use, the apparatus 1100 can be supplied with the jaws 1111, 1112 closed, so that the projections are contained in the substance 1150. The jaws 1111, 1112 can then be opened, allowing the substance to be delivered to the subject. Following use, the jaws can be returned to the closed position, thereby storing the used patch safely within the cavity. This prevents accidental contamination of other individuals with the used patch.

In one example, the substrate 120 engages the housing 1130, for example using a clip fit, friction fit, interference fit or the like. By providing a sealing engagement, this assists with retaining the substance 1150 within the cavity 1140 when not in use. This can also be used to allow agitation of the substance, thereby ensuring coating on the patch projections, or removal of material from the patch after use. Additionally, this can be used to allow the apparatus to be disposed of as a single unit, with the substance and used patch being contained, which can be useful in disposal of potentially contagious or otherwise hazardous material.

In one example, the use of a piercable sealing film 1160, can also reduce the chance of the substance exiting the cavity 1140 when the jaws are in the open position. This arrangement can be used to provide apparatus for delivering solutions, such as vaccines, without requiring an operator to apply the liquid to the patch prior to use. This makes the apparatus suitable for use in remote regions, by ensuring that the solution remains free of contaminants until required.

It will be appreciated that even in absence of a substance 1150, the arrangement is still suitable for collecting material from a subject and retaining this for subsequent analysis without the need for separate storage apparatus.

It will be appreciated that the use of a well can also be implemented with an arrangement of apparatus similar to that shown in FIGS. 7 and 8.

Figure 12A:
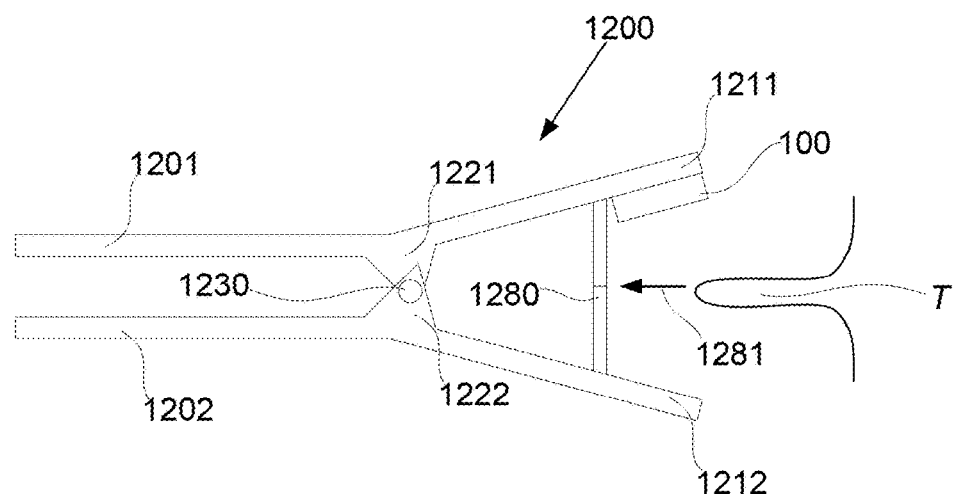
FIGS. 12A and 12B are schematic diagrams of a fourth example of apparatus for applying a patch to a subject.
Figure 12B:
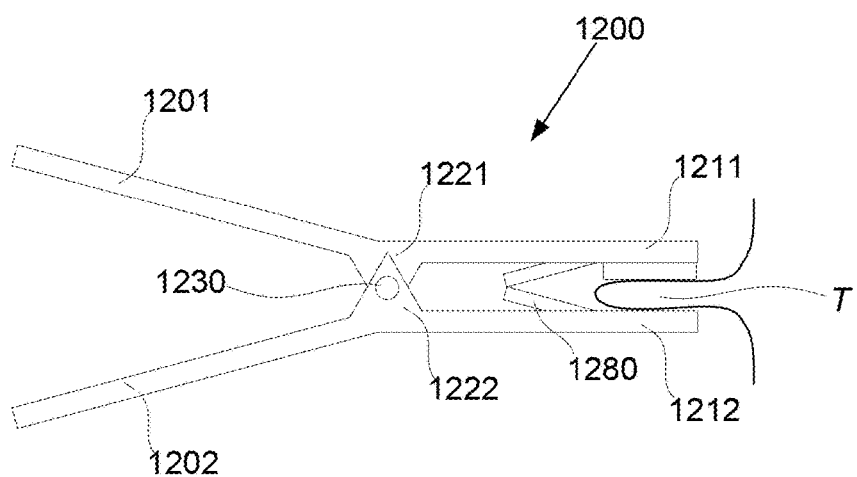

An example of apparatus including a stop to allow controlled deployment will now be described with reference to FIGS. 12A and 12B.

In this example, the apparatus 1200 includes first and second arms 1201, 1202, having respective jaws 1211, 1212. The arms are connected via pivot mounts 1221, 1222 and a pivot 1230, with a spring (not shown for clarity) also being provided to bias the arms 1201, 1202 into a closed position in a manner similar to that described above with respect to the apparatus 400. Although a spring is described, it will be appreciated that pivoting can be achieved in any suitable manner, such as through the use of a compliant or flexible material that allows cantilevered deflection of the jaws.

In this example, the apparatus also includes a hinged stop 1280. When the jaws 1211, 1212 are moved into the open position, the stop 1280 engages, thereby preventing closure of the jaws 1211, 1212. As tissue T, or another part of the subject is inserted between the jaws 1211, 1212, as shown by the arrow 1281, the tissue T engages the stop 1280, causing this to hinge, thereby allowing the jaws to engage the tissue T as shown.

Accordingly, it will be appreciated that this provides a mechanism for automatically applying the patch when at least part of the subject is correctly inserted between the jaws 1211, 1212. This arrangement can also be used to allow the apparatus 1200 to be transported with a patch 100 mounted thereon, without risk of the patch 100 being damaged by contacting another patch or the second jaw 1212.

It will be appreciated that the use of a stop can also be implemented with an arrangement of apparatus similar to that shown in FIGS. 7 and 8.

An example of apparatus for applying a micro-fluidic patch to a subject will now be described with reference to FIGS. 13A and 13B.

In this example, the apparatus 1300 includes first and second opposable jaws 1311, 1312. The jaws 1311, 1312 are typically provided on respective arms, which may connected via a pivot, similar to the pivot 430 of FIGS. 4A to 4D or 5A to 5C, or via a connector, similar to the connector 630 of FIGS. 6A to 6D.

Figure 13A:
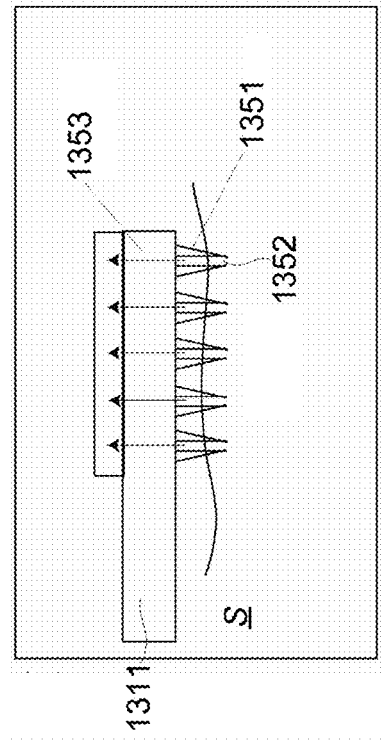
FIGS. 13A and 13B are schematic diagrams of examples of apparatus for applying a micro-fluidic patch to a subject.

In the example of FIG. 13A, the first jaw 1311 includes a micro-fluidic patch 1350 mounted on a first side, with a reservoir 1360 provided on an opposing second side of the first jaw 1311. In contrast, in the example of FIG. 13B, the micro-fluidic patch 1350 is mounted to the reservoir 1360, which is in turn mounted to the jaw 1311.

In either case, the micro-fluidic patches 1350 include hollow projections that are in fluid communication with the reservoir 1360, allowing liquid to be delivered to the projections, or to allow liquid to be delivered from the projections and received by the reservoir, as will be described in more detail below.

Figure 13C:
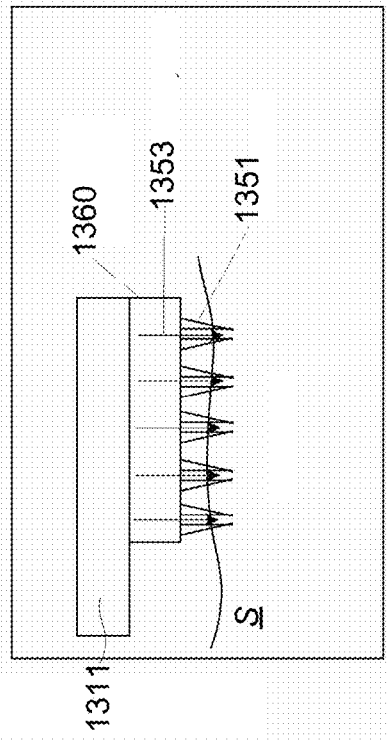
FIG. 13C is a schematic diagram of an example of apparatus for applying a micro-fluidic patch to a subject to remove fluid from a subject.

As shown in more detail in FIG. 13C, the first jaw 1311 includes a micro-fluidic patch 1350 mounted on a first side, with a reservoir 1360 provided on an opposing second side of the first jaw 1311. The patch 1350 includes hollow projections 1351, defining fluid channels 1352 extending up the length of the projections 1351. The fluid channels 1352 are in fluid communication with the reservoir 1360, as shown by the arrows 1353. It will be appreciated that this is typically achieved by having the channels 1352 extend through a patch substrate (not shown) and through the respective jaw 1311. As an alternative to requiring the channels extend through the jaw 1311, the patch 1350 and reservoir 1360 can be integrally formed, with the patch 1350 and reservoir 1360 being supported by the jaws 1311, for example by having the patch mounted in an aperture similar to the aperture 741 of FIGS. 7A to 7D.

Figure 13B:
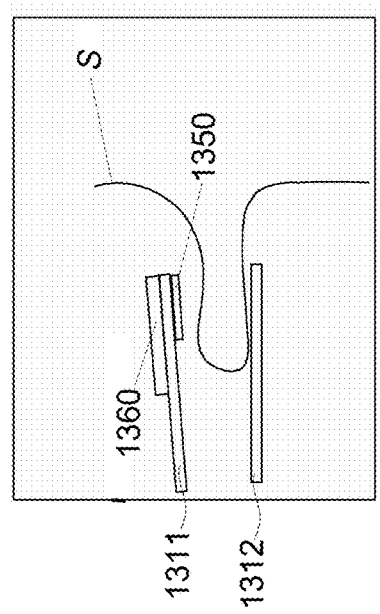
Figure 13D:
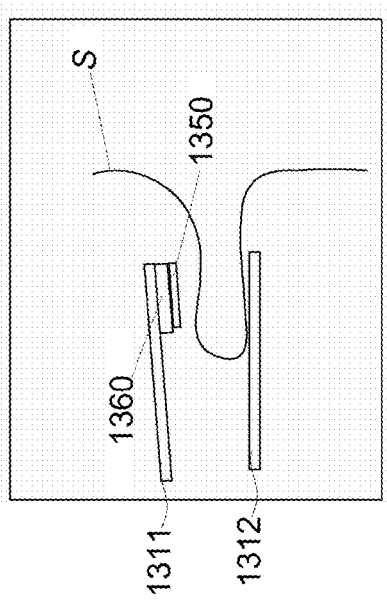
FIG. 13D is a schematic diagram of an example of apparatus for applying a micro-fluidic patch to a subject to deliver fluid to a subject.

In contrast, in the example of FIG. 13B, and as shown in more detail in FIG. 13D, the micro-fluidic patch 1350 is mounted to the reservoir 1360, which is in turn mounted to the jaw 1311. Accordingly, this avoids the need for channels to extend through the jaw 1311, as will be appreciated by persons skilled in the art.

The above described arrangements can be use to extract fluids from the subject for storage in the reservoir 1360, or alternatively, deliver fluids from the reservoir 1360, to the subject.

In the case of extraction of fluids, which is typically performed using the arrangement of FIG. 13C, extraction can be achieved using any suitable mechanism. For example, this may occur through capillary action, depending on the diameter and arrangement of the fluid channels 1352. Alternatively, the pressure of the patch being applied to the subject can cause fluid to be urged along the channels 1352 and into the reservoir 1360. A further alternative is for the reservoir 1360 to be configured to allow a reduced pressure to be applied to the fluid channels 1352, thereby allowing the fluid to be drawn into the reservoir. In one example, this could be achieved by having the internal volume of the reservoir 1360 expand when the jaw 1311 applies the patch to the subject, thereby reducing the pressure in the reservoir 1360.

In the case of delivery of fluid, which is typically performed using the arrangement of FIG. 13D, the action of urging the patch 1350 and jaw 1311 against the subject can be used to urge fluid along the channels 1352 and into the subject. However, it will be appreciated that this is not essential and other delivery mechanisms may be used, for example to allow fluid to be delivered by infusion, or the like.

A number of further examples will now be described with reference to FIGS. 13E to 13H.

Figure 13E:
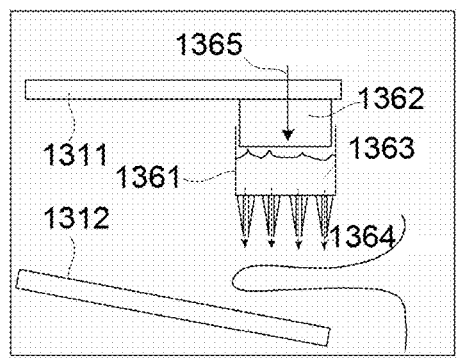
FIG. 13E is a schematic diagram of a second example of apparatus for applying a micro-fluidic patch to a subject to deliver fluid to a subject.

In the example of FIG. 13E, the reservoir 1360 includes a reservoir body 1361 and a plunger cap 1362, which sealingly engages the body 1361 to allow a fluid 1362 to be contained therein. The plunger cap 1362 is attached to the jaw 1311, so that as the patch 1350 is urged against the subject S, the cap is urged into the reservoir body 1361 as shown by the arrow 1365, thereby displacing the fluid 1363, and urging this via the channels 1352 into the subject, as shown by the arrows 1364. It will be appreciated that the plunger cap could be designed to be held in position prior to application using a friction, interference or other mechanism to ensure that projections penetrate the subject prior to the fluid infusion commencing.

Figure 13F:
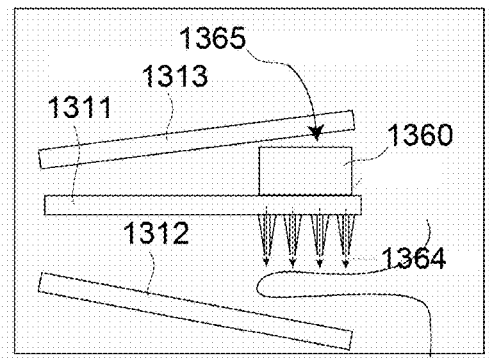
FIG. 13F is a schematic diagram of a third example of apparatus for applying a micro-fluidic patch to a subject to deliver fluid to a subject.

In the example of FIG. 13F, the patch 1350 is mounted on a first side of the jaw 1311, with a reservoir 1360 provided on an opposing second side of the first jaw 1311. An additional third jaw 1313 is provided, for example in an arrangement similar to that shown in FIGS. 7A to 7F, so that the reservoir 1360 is provided between the first and third jaws 1311, 1313. In this example, the reservoir 1360 includes a deformable body that is adapted to deform as the third jaw 1313 is urged towards the first jaw 1311. Accordingly, in use the first and second jaws 1311, 1312 are closed to apply the patch 1350 to the subject S. The third jaw 1313 is then closed as shown by the arrow 1365, allowing the reservoir 1360 to be deformed and the fluid therein urged through the channels 1352 and into the subject, as shown by the arrows 1364.

Figure 13G:
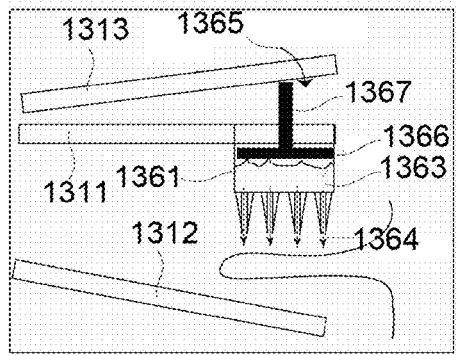
FIG. 13G is a schematic diagram of a fourth example of apparatus for applying a micro-fluidic patch to a subject to deliver fluid to a subject.

In the FIG. 13G example, the reservoir 1360 includes a reservoir body 1361 coupled to the jaw 1311. A plunger 1367 is provided in the reservoir body 1361, with an actuating arm 1366 extending through the first jaw 1311. An additional third jaw 1313 is provided, for example in an arrangement similar to that shown in FIGS. 7A to 7F. In use, the first and second jaws 1311, 1312 are closed to apply the patch 1350 to the subject S. The third jaw 1313 is then closed, thereby urging the plunger 1365 into the reservoir 1360, thereby displacing the fluid therein and urging this through the channels 1352 and into the subject, as shown by the arrows 1364.

Figure 13H:
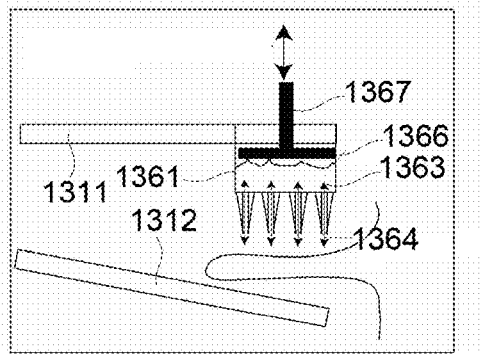
FIG. 13H is a schematic diagram of a fifth example of apparatus for applying a micro-fluidic patch to a subject.

In the example of FIG. 13H, the reservoir 1360 includes a reservoir body 1361 coupled to the jaw 1311. A plunger 1367 is provided in the reservoir body 1361, with an actuating arm 1366 extending through the first jaw 1311. In use, the first and second jaws 1311, 1312 are closed to apply the patch 1350 to the subject S. The plunger 1367 may then be moved either towards or away from the patch 1360, thereby allowing fluid to be supplied to or extracted from the subject.

It will be appreciated that a number of variations on the above example arrangements can be used to displace fluid from or draw fluid into a reservoir. For example, a plunger or other similar arrangement could be moved using any suitable actuator, such as an electronic device, manual press, button, or the like. It will also be appreciated that a syringe or other compressing or tensioning device could be used to alter the effective internal volume of the reservoir.

Accordingly, it will be appreciated that in the examples of FIGS. 13A to 13H, hollow projections are used to either deliver a fluid, such as a fluid containing a drug, vaccine or bioactive molecules, from a reservoir into the subject, or to extract a fluid sample from the subject through the hollow projections.

The fluid reservoir can be located on either side of the jaws used to apply the patches to the subject. Closing of the jaws to apply the patch to the subject can be used to urge fluid into the skin, or fluid can be delivered via infusion, with the patch typically being applied to the subject prior to the deliver of fluid through the projections, although this can occur simultaneously. Similarly samples can be extracted using a variety of mechanisms, such as capillary action. However, other separate mechanisms could be used, allowing fluid to delivered or extracted by mechanisms including one or more of a moveable jaw, deformation of the reservoir, a syringe, a plunger, a plunger cap, a mechanical actuator, a manual actuator; and an electronic actuator.

Example experiments to demonstrate the effectiveness of the apparatus will now be described.

Figures 14A, 14B, 14C:
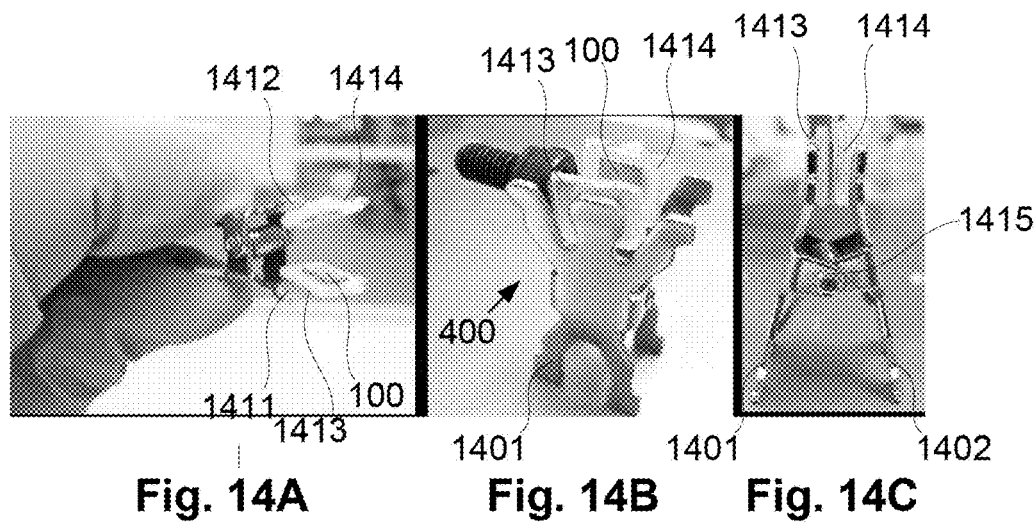
FIGS. 14A to 14C are images of an example of an experimental apparatus for applying a patch to a subject.

An example prototype apparatus for applying a patch for proof of concept experiments is shown in FIGS. 14A to 14C.

As shown, the apparatus includes first and second arms 1401, 1402 having first ends defining the jaws 1411, 1412. The arms 1401, 1402 are mounted about a spring loaded pivot 1415 with a patch 100 mounted on one or both substrates 1413, 1414 on each of the jaws 1411, 1412, as shown. Again, although a spring loaded pivot is described, it will be appreciated that pivoting can be achieved in any suitable manner, such as through the use of a compliant material, or the like.

Figures 15A, 15B:
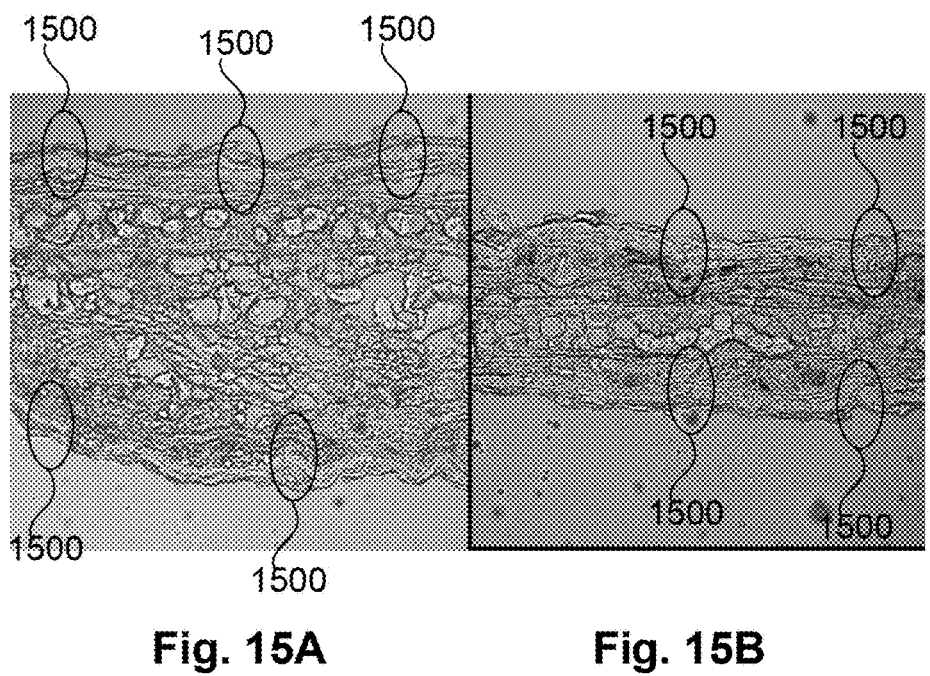
FIGS. 15A and 15B are images of two 16 μm thick sections of skin where dye has been delivered using the apparatus of FIGS. 14A to 14C.

In this example, the patches were coated with a dye, allowing the dye to be delivered to a sample. Preliminary experimental data is shown in FIGS. 15A and 15B, which show two 16 μm thick sections of skin (viewed as cross-sections) where dye has been delivered using the two patches 100 simultaneously, as shown at 1500 (only some delivery sites identified for clarity). This penetration profile is consistent and similar in depth achieved with more complex prior art approaches, such as a 'conventional' spring loader applicator, shown to achieve strong immune responses.

An experiment to demonstrate the effect of projection shape on penetration depth will now be described with reference to FIGS. 16 and 17.

In this example, projection patches were synthesised from silicon using a process of Deep Reactive Ion Etching in accordance with the techniques described in copending patent application number PCT/AU2009/000142. The projections were solid silicon, sputter coated with a thin layer of gold (400-1500 nm in thickness). An individual patch is 5×5 mm in size and the central 4×4 mm area contains 3364 projections. The distance between the centres of adjacent projections is 70 μm. The patches have 65 μm long projections consisting of 50 mm conical targeting section atop a 15 μm cylindrical supporting section.

The morphology of patches and coating were characterised by a Philips XL30 scanning electron microscope with all samples being tilted at 45° for scanning electron microscopy (SEM). SEM images of example uncoated patches are shown in FIGS. 16A and 16B. Active coatings (fluorescent or antigenic) were dry coated on the surface of the projections such that the coating dissolves once wetted in the skin for the vaccine delivery. 8 μL solution of 0.4% Vybrant® DiD (a lipophilic fluorescent dye, Molecular Probes Inc., Eugene, Oreg.) and 1.5% Methylcellulose was coated on the projections and then dried using a nitrogen jet method described in copending patent application PCT/AU2008/001903. The dye highlights the needle penetration tracks when released from the projections. SEM images of example uncoated patches are shown in FIGS. 16C and 16D.

Concentrations of DiD in solution were titrated to ensure that the projection track is clear in the skin. The amount of vaccine coated on the patches was determined with six coated patches that were dipped in 200 μl of water overnight to thoroughly remove the coated vaccine. Then the patches are removed from the solutions and the UV-Vis absorption spectra of all the solution samples were scanned. The UV absorbance (at 280 nm) of all samples was recorded and compared with the absorbance of standard samples, so the amount of coated vaccine on each patch can be calculated. The standard samples are different volumes of coating solution diluted in 200 μl of water.

The tissue used for the experiments was mouse ear skin from 7 week old C57BL/6 female mice. Experimentation was performed in-vivo, with five ears (n=5) being used per group for all experiments (one patch per ear).

Two example application techniques were used—by hand and using a spring-loaded applicator device. Patches were maintained on the skin for five minutes, with parameters as shown in Table 1 below.

TABLE 1

| Application Method | Velocity | Maintaining Load (N) |
|---|---|---|
| Hand | ~0 m/s | 12.2 ± 1.2 |
| Velocity | 0.56 m/s | 0.6 |
| Velocity | 1.22 m/s | 0.6 |
| Velocity | 1.96 m/s | 0.6 |
| Velocity | 2.54 m/s | 0.6 |

During application, and placement on the skin, the apparatus for applying the patch was maintained in a fixed stand to avoid deviations in its location. Hand application loads were measured by applying 10 patches to ears whilst supported by a balance, giving an application load of 12.2±1.2 N (n=20 measurements).

Previous studies had highlighted that affixing the patch to a plunger for application resulted in the patch bouncing upon impact beyond ~1.5 m/s. This is detrimental to the drug/dye release as the projections must remain wetted for a period of time. To avoid this, an attachment can be used to ensure that when the patch was applied to the skin, regardless of the application velocity, it would remain there. This was done using a semi-rigid carbon tab with the side facing the skin being adhesive to thereby affixing the patch to the skin. The other side possessed an adhesive to allow the carbon tab to be attached to the bottom of the spring device. However, with the apparatus described above, this is not essential as the biasing mechanism can assist in retaining the patch in position as previously described. The patch was positioned 1 mm above the skin with four velocities being used for application, 0.56 m/s, 1.22 m/s, 1.96 m/s and 2.54 m/s.

After patch application, the ears were excised and the skin prepared for confocal microscopy section dye measurement. To do this the skin was fixed in 2% paraformaldehyde in 0.1M phosphate buffer pH=7.4, preceding cryo-preservation in accordance with Lutty et al. [24]. Once frozen, 10 μm thick sections of skin were cut on a cryostat before imaging on a Zeiss LSM510 Meta confocal microscope (Carl Zeiss, Inc., Germany). Vybrant® DiD was excited using a 633 nm laser with emission collected from 650-710 nm. SEM images in FIGS. 17A and 17B show holes 1700 where projections have penetrated the skin, with FIG. 17B showing the dye delivered. The dye tracks were measured using a Zeiss LSM Image Viewer program to determine the delivery depth of dye payload. This shows successful delivery beyond the stratum corneum, indicating the apparatus is capable of delivering molecules into the skin.

FIGS. 18A to 18F show penetrative channels through the stratum corneum to lower layers of the skin after application of a patch at velocity. At 0.56 m/s velocity, shown in FIGS. 18A and 18D there is high variability in both the size of the projection holes, and the number of sites adequately punctured. Increasing to 1.22 m/s in FIGS. 18B and 18E there is increased site coverage with large holes. Application at 1.96 m/s shown in FIGS. 18C and 18F appears to give a much clearer penetration, up to the "step" in the projection in many cases. At this velocity >95% of the projections on an patch pierce the skin, with the majority giving clear puncture as shown in F.

The holes that are created vary in size, depending upon the velocity with which the patch was applied to the skin. The size of holes created increases with the application velocity of the patch. For example, at 1.96 and 2.54 m/s velocity, Cryo-SEM data show that there are significant holes created over almost the complete 4 mm×4 mm area of the patch. At lower velocities (<1.22 m/s), holes are also created although the diameter and coverage of these is variable and reduced. The lowest device applied velocity (0.56 m/s) resulted in significant indentation of the surface but a low overall penetration of the skin surface (30% or lower).

Figure 19B:
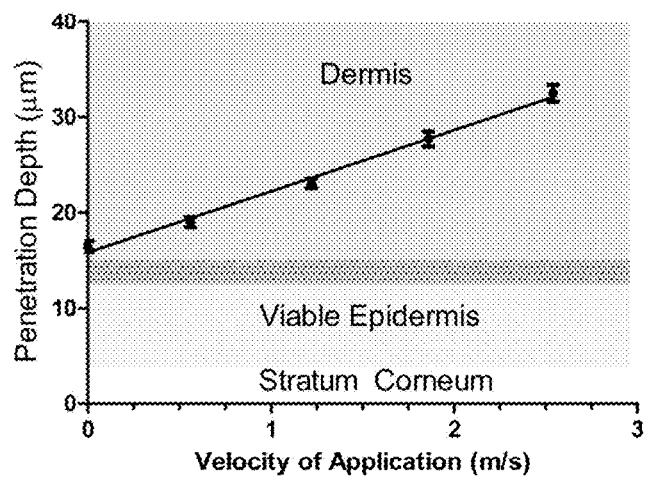
FIG. 19B is a graph of collapsed data showing projection penetration at different application velocities.
Figure 19C:
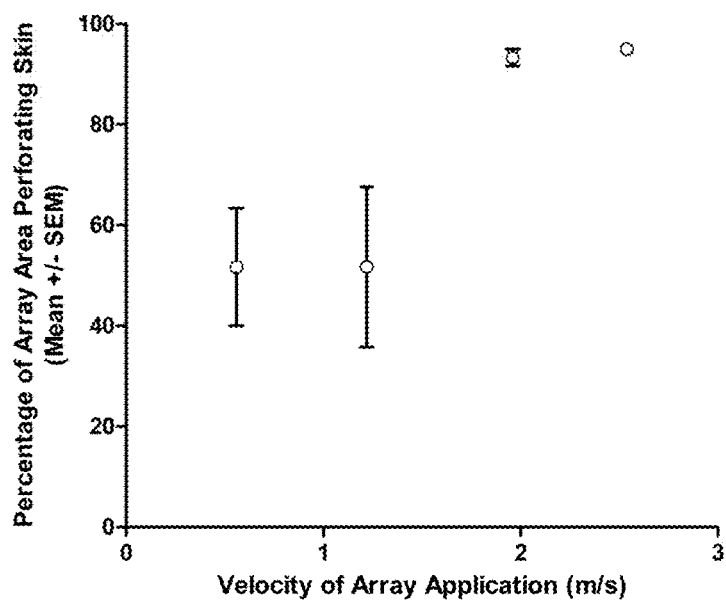
FIG. 19C is a graph showing the percentage of projections piercing the skin surface at different application velocities.

The dye delivery experiment shows a strong linear proportionality relationship exists between application velocity and penetration depth. FIGS. 19A and 19B show the raw and collapsed data for projection penetration respectively, with the percentage of projections from each patch actually piercing the skin surface being shown in FIG. 19C. Each data point represents a projection delivery site at the maximum depth of its dye delivery. As velocity increases, the depth of penetration is increased. Application at 0.56 m/s results in penetration that will deliver almost all payload delivered into the VE or above. Increasing this to 1.96 m/s results in delivery to both VE and dermis.

A graph of mechanical skin Young's modulus from literature is included in FIG. 19A showing the layer properties as projections enter skin. For each point, there will be significant payload delivery at depths up to that maximum location. Using a non-parametric Kurskall-Wallis test these data were found to all be statistically independent apart from the comparison between the hand application and 0.56 m/s application.

In FIG. 20 the raw data is presented in histogram profile form, indicating the distribution of penetration depths measure by dye delivery. The data show that at lower velocities there are two distinct peaks of penetration, one around the basal layer of the epidermis—one reaching into the dermis. This indicates an effect decelerating the projections as they enter the skin (or more correctly, the skin is deflecting further from the projections at this point). A lower application velocity will therefore result in the patch stopping in this layer, with an increased velocity overcoming this barrier for deeper delivery.

Surface data from microscopy allows deduction of the quality of skin puncture and the percentage projections on the patch that puncture the skin. This was done using a Scanning Electron Microscope (SEM) fitted with a cryo-stage and preparation chamber (Oxford Conn.—1500 and Philips XL30 SEM, Philips, Netherlands). For these experiments the patches were coated as described above. The patch was applied to the skin in the same manner as in the dye studies. The patch and skin assembly was then slush frozen in liquid nitrogen ($LN_2$) and transferred to a cryo-preservation chamber under vacuum. At this point the patch was removed from the skin and the skin then sputter coated with a thin (few nanometers) layer of gold for imaging purposes. This technique ensures that the holes in the surface of the skin are as they would be in-situ. Skin morphology changes are restricted by the projections during the freezing, allowing accurate quantification. Imaging is then performed by SEM.

The Cryo-SEM images are shown in FIG. 21. This shows that where the patch is removed an upper layer of corneocytes has remained on the projections. The frozen corneocytes reveal penetration profiles and show the bulk behaviour of the outermost layer of skin. It is clear that for the case shown (1.96 m/s) that the step in conical projection geometry is acting to restrain entrance to the skin. This is also evident in the preceding figure where there are circular impressions around projection holes at higher velocities indicative of the step reaching the skin. This highlights that the projection geometry can be used to limit projection penetration.

An experiment to quantify the delivery of ovalbumin antigen to skin was performed using a radiaoactive assay. Each patch was coated 7.5 μl of methylcellulose containing 25 nCi of $^{14}C$ Ovalbumin. The patches were coated as described above, with the mass of antigen coated on the patch being found to be 0.54±0.04 μg.

After application the patches were removed from the skin and the skin wiped 20 times with a damp cotton bud to remove all antigen deposited on the surface of the ear. The bud stem was then cut off and the heads collected in scintillation vials with 1 ml of PBS added and mixed. The used patches were also collected in scintillation vials with 1 ml of PBS. Each ear was then excised and placed in a 10 ml Reactivial® (Thermoscientific, Rockford USA) and 750 ul of tissue solubiliser solution (Soluene-350, Perkin Elmer) heated in at 60° C. for 2-4 hours to solubilise the tissue. Vials containing the cotton bud swabs, the used patches and the solubilised ears were then transferred to scintillation vials and 10 ml of Scintillation liquid (Hionic-Fluor Perkin Elmer) added. All vials were then counted in a liquid scintillation counter for 2 min each sample. n=4 ears were used per group. Sums of radioactive counts were compared to a single coated patch for comparison and to determine losses.

FIG. 22A shows the dose of Ovalbumin protein delivered per patch with varied application velocities, using radioactive quantification. Three bars are present for each application method/velocity, showing the mass of payload remaining on the patch, delivered onto the surface of the skin, or delivered within the skin. Bars are mean with Standard Error of Mean (SEM).

Of importance for immune response generation is the percentage payload delivered to the skin shown in FIG. 22B. This shows that as the velocity of application was increased a greater percentage of the payload was delivered into the skin. This has a linear fit of $R^2$=0.999, comparable with the dye delivery data. In all cases the majority of payload remained on the patch. The payload on the skin indicated antigen reaching the skin surface from either the edge of projections or the base of the patch. Between 1.22 m/s and 1.96 m/s there was a significant increase (more than double) in payload deposited on the skin surface. This was mirrored with a reduction in the remaining mass on the patches. Non-parametric Kurskal-Wallis tests gave medians as statistically different ($p<0.05$). Total system loss was less than 2% during processing.

Experimentation to determine the level of immune response at different applications was performed using C57BL/6 mice. Patches were coated with coating solution as described above containing Ovalbumin Protein (Sigma Aldrich) 10 mg/ml as an antigen and Quil-A 2 mg/ml as an adjuvant. Two patches were applied to each mouse (one to each ear), whilst they were anaesthetised, using 5 mice per group and maintained on the skin for five minutes each after initial application. A positive control of 30 μg OVA protein and 10 mg Quil-A injected intramuscularly to the thigh was used, with a negative control of non-immunised mice. Mice were eye-bled and sera extracted 63 days after immunisation. Assessment of total anti-OVA IgG was then performed using an Enzyme Linked Immunosorbent Assay (ELISA)

Antibodies (IgG) generated by the vaccinations were measured by Enzyme-Linked Immuno Sorbent Assay (ELISA). Proteins were adsorbed to the plates at a concentration of 50 μg/ml in 0.1M $NaHCO_3$ overnight at 4° C., and residual binding sites blocked with a 3% BSA in PBS pH 7.4. Test sera were diluted in 1% BSA and 0.02% Tween-20 in PBS. Sera were allowed to react for 2 h at 23° C. Plates were washed with 0.02% Tween-20 in PBS and sheep anti-mouse sheep anti-mouse Ig-horseradish peroxidase antibody added and was allowed to react at 23° C. for 1.5 hours. 50 µl of ABTS solution (25 mg ABTS dissolved in 50 ml of 80 mM citrate-phosphate buffer pH 4.5, containing 18 µl of 30% $H_2O_2$) was added to each well and the $O.D._{405}$ recorded.

Figure 22A:
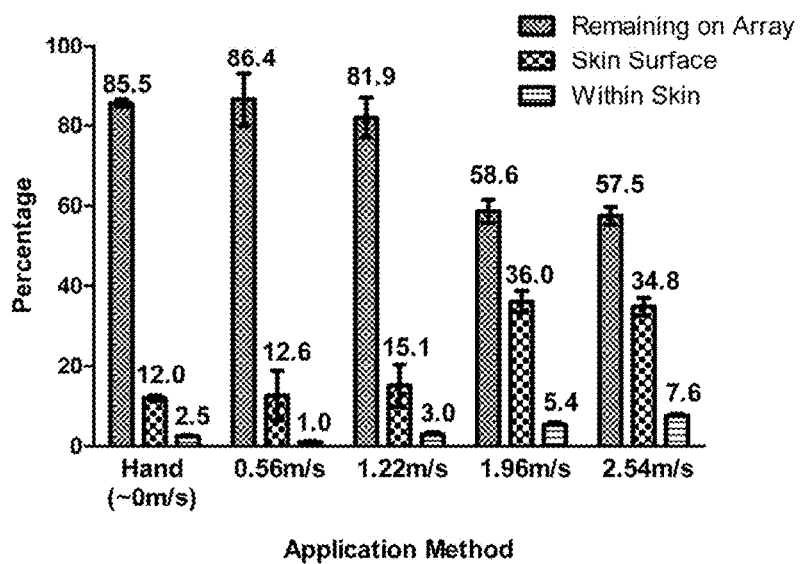
FIG. 22A is a graph showing the dose of Ovalbumin protein delivered per patch for different application velocities.
Figure 22B:
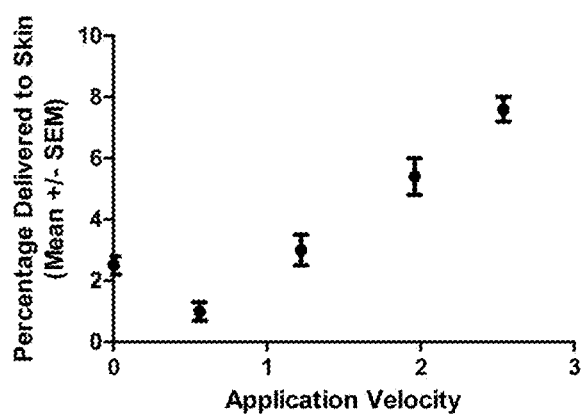
FIG. 22B is a graph showing the payload percentage delivered to skin for different application velocities.
Figure 22C:
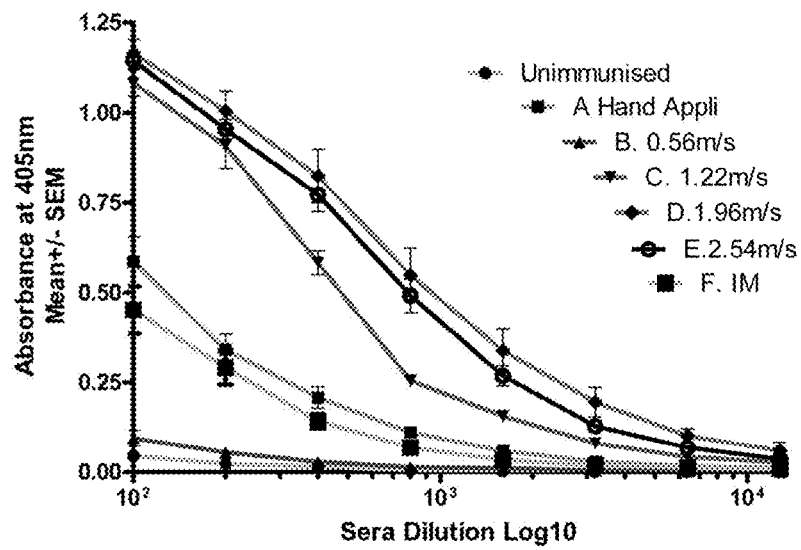
FIG. 22C is a graph showing the immune response of mice immunised using patches at different application velocities.

The immune response of mice immunised using patches are shown in FIG. 22C. The total anti-ovalbumin protein antibody levels increase as velocity of application increases, to plateau around 1.96 m/s. Beyond this velocity there is no statistical change in total antibody levels generated. At 0.56 m/s there is an undetectable level of antibody generation. Hand application of the patches result in variable immune response over the five animals, ranging from zero immune response, to significant positive responses. Sera dilutions showed that application of an patch at 1.22 m/s or above gives an antibody response significantly higher than that of an intramuscular injection of 30 µg.

Figure 23:
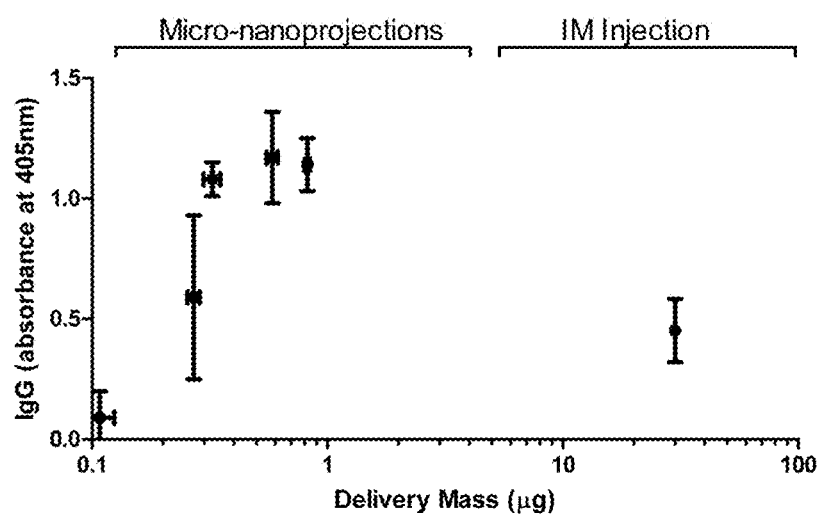
FIG. 23 is a graph showing the variation of immune response with payload delivery.

As the velocity is increased the payload that is delivered into the skin is increased. Combining data of delivery mass from FIGS. 22A and 22B, and the 1:100 dilution immune response shown in FIG. 22C, the dose dependency of the total IgG generation can be determined. FIG. 23 shows this with the lower delivery mass giving a lower IgG generation. The higher velocities (above 1.22 m/s) delivered a mass of antigen that resulted in a maximum IgG generation, with the response reaching a plateau.

The results from the experiments are summarised in Table 2 below.

TABLE 2

| Application Velocity | Penetration Depth (um) | Delivery Volume (µg) | Immune Response (mean absorbance at 1:100 dilution) |
|---|---|---|---|
| Hand (~0 m/s) | 16.5 ± 5.3 | 0.20 ± 0.03 | 0.59 ± 0.34 |
| 0.56 m/s | 19.0 ± 5.0 | 0.50 ± 0.03 | 0.09 ± 0.11 |
| 1.22 m/s | 23.1 ± 5.3 | 0.60 ± 0.05 | 1.08 ± 0.07 |
| 1.96 m/s | 27.7 ± 7.7 | 1.08 ± 0.06 | 1.17 ± 0.19 |
| 2.54 m/s | 32.5 ± 8.2 | 1.52 ± 0.04 | 1.14 ± 0.11 |

Accordingly, the experiments show that skin can be controllably penetrated for the delivery of biomolecules, using a patch applied at varied velocities. The linear increase in penetration depth, from 25% to 75% of total needle length with velocity indicates skin's strong strain-rate dependant behaviour. Ear damage showed that application of increased force would not be a practical solution for patch application.

Deflection has previously been found to be a limiting factor for successful penetration so is best mitigated. The penetration of the skin surface (the SC) at lower velocity is limited by the large deflections that the skin undergoes prior to puncture. For mouse ear, local compression is focussed down to the cartilage on the ventral side by the projections, with the skin on the dorsal side of the ear experiencing a more distributed pressure field.

However, at high strain rates (>5000% per sec) skin behaves up to 60% stiffer in Young's modulus. This provides for a significantly lower deflection of the skin prior to critical puncture stress. Assuming that the stratum corneum would initially curve around projection tips (<0.5 µm diameter), a strain rate at least an order of magnitude higher can be achieved with the above described apparatus using a sufficiently high application velocity.

Furthermore, the use of a stepped projection can be used to control the depth of penetration, even at high velocity. In particular, at 2.54 m/s application, the surface of the skin shows circular indentations as a result of the step in geometry of the projections contacting the skin surface. When these reach the surface they present a larger area to the corneocytes that they are touching, allowing the patch to be decelerated and penetration stopped. Accordingly, the step in the geometry of the projections, can be used to target specific cells or layers of cells in the skin.

The experiments also show that patch placement on the skin can vary penetration performance. When the patch reaches the skin it contacts a non-flat surface with considerable variation over the area of a 4 mm×4 mm patch, due to macro-scale misalignments and micro-scale undulations, including hairs, hair follicles and any dirt on the skin surface.

Ideal placement of a patch on skin would be with the projections normal to the skin. This is not easy at projection scale to get exact and at low velocities, if one corner reaches the skin first, then those projections will penetrate slowing the patch and reducing the velocity of the remaining projections. At higher velocities one corner penetrating first is less of a problem as the patch will still have enough momentum to continue compressing the skin and allowing the other projections to penetrate. This provides another reason for the use of a higher application velocity, such as above 1 m/s.

Figure 24:
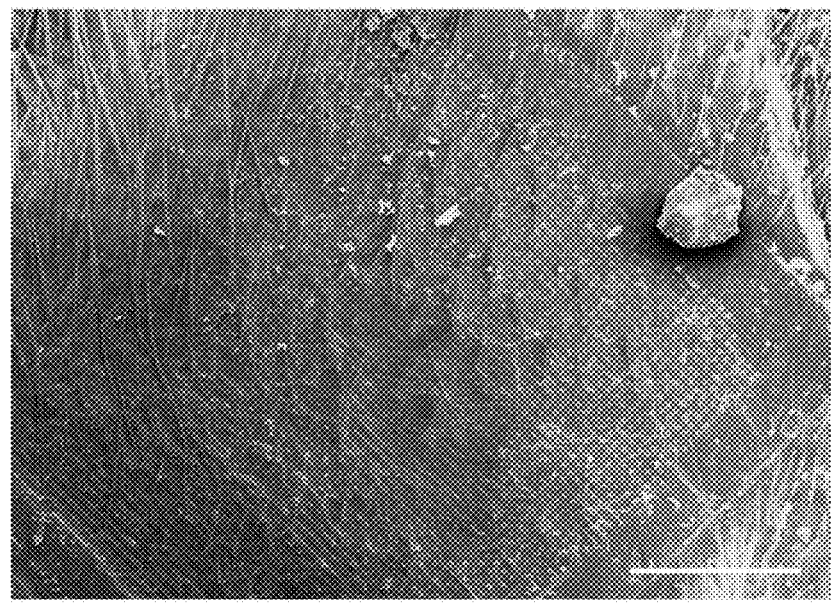
FIG. 24 is a Cryo-SEM image of mouse ear skin after application of a patch.
Figure 25A:
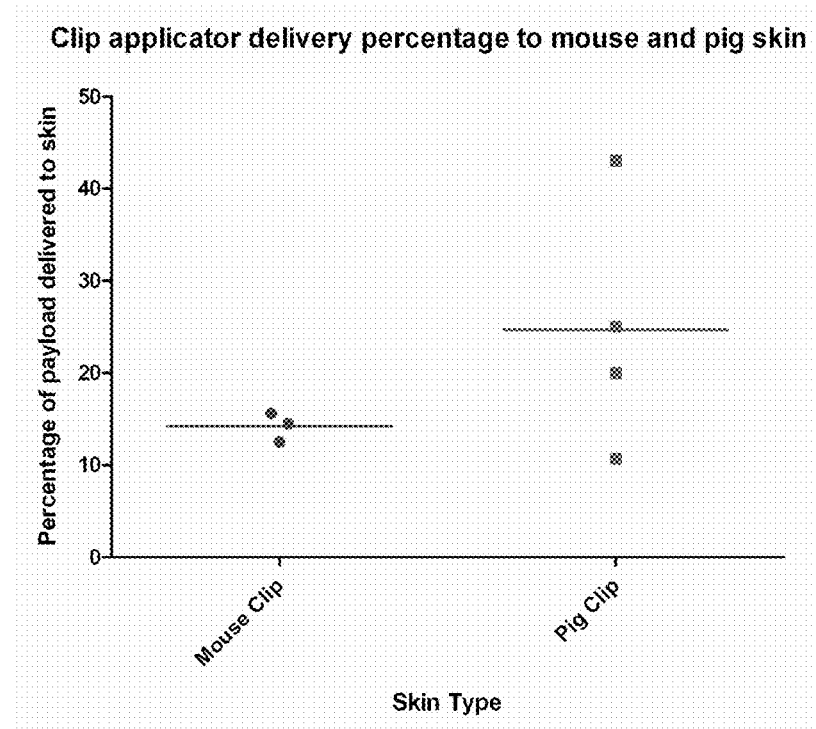
FIG. 25A is a graph showing a comparison of payload delivery to a mouse and pig ear using the applicator of FIGS. 14A to 14C.
Figure 25B:
FIGS. 25B and 25C are graphs showing an example of a comparison of vaccination of mice using Fluvax 2010 with the applicator of FIGS. 14A to 14C compared to positive and negative controls; and, FIG. 26 is a graph showing an example of a comparison of vaccination of mouse buccal mucosal tissue using Fluvax 2010 with the applicator of FIGS. 14A to 14C compared to a number of controls.
Figure 25C:
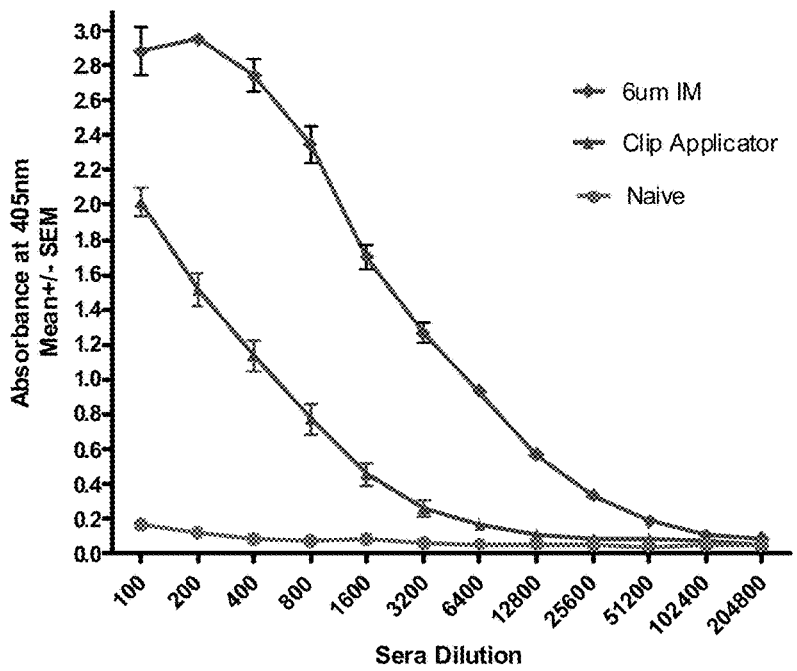

The scale of the projections can also impact on the application of the patch, with edges of patches contacting the skin during application, as shown in FIG. 24. In this example, if the patch was applied at 0.56 m/s or by hand would result in them taking the decelerating load instead of the projections. This would reduce penetration at these conditions. At higher velocities the increased rigidity will ensure that this contact will not happen until the projections have penetrated the skin, increasing efficiency. The benefit of this is the increase in penetrated surface area.

The method of patch attachment in this experiment avoided any bouncing of the patch on the skin. If the patch were to bounce on the skin then during the first penetration (milliseconds or less) full dissolution of the coating would be required as the projections will not always locate with the original holes in the second impact. The second impact will not result in deep holes so bouncing will generally reduce delivery volume. The additional adhesive around the patch on the carbon tab formed a temporary bond with the skin surface ensuring that the projections on the patch are maintained beneath the SC after application. This method can be used to help material to be delivered in a solid manner into the skin and not only onto the surface after creating holes in the skin.

Examining the penetration of adjacent stratum corneum punctures indicates that there are no variations between whether projections punctured through the centre of a corneocyte or between corneocytes. The stratum corneum is made up of on average of 11 randomly arranged layers of corneocytes (in the mouse) so even hitting between two corneocytes would result in hitting more centrally on layers below. Probabilistically, a similar path overall will be taken by all projections—the bulk resistance to penetration provided by the SC will be the same for each projection.

As the projections enter the skin they will firstly pass through the SC, which will slow the patch, before penetrating into and through the mechanically weak VE. At 70% hydration, the VE is highly influential on the bulk viscoelastic properties of the skin. A cylindrical projection pushing through the skin surface experiences a gradual rise in resistance through the VE. The projections would have experienced an additional increased resistance as they push deeper due to their conical shape requiring the surface of the SC to continue to tear. As the projections reach the dermis they will experience a step increase in resistance due to the greater mechanical strength of this layer.

Figure 20:
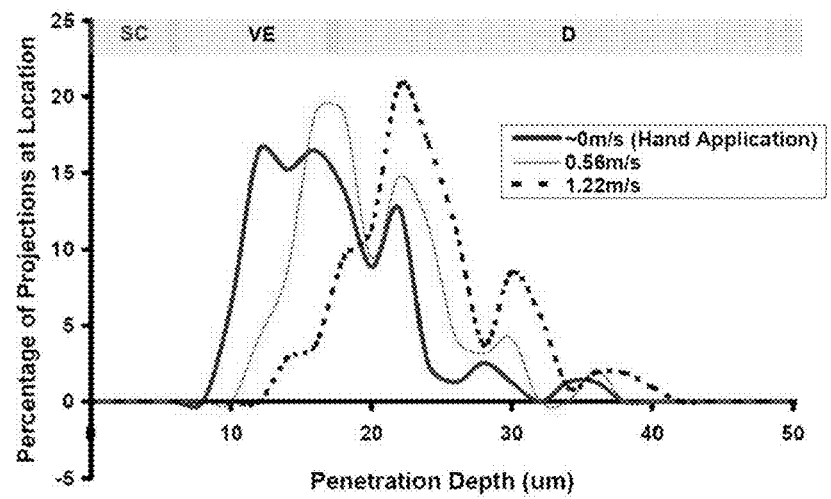
FIG. 20 is a histogram of the percentage of projections at a given depth for different application velocities.
Figure 21:
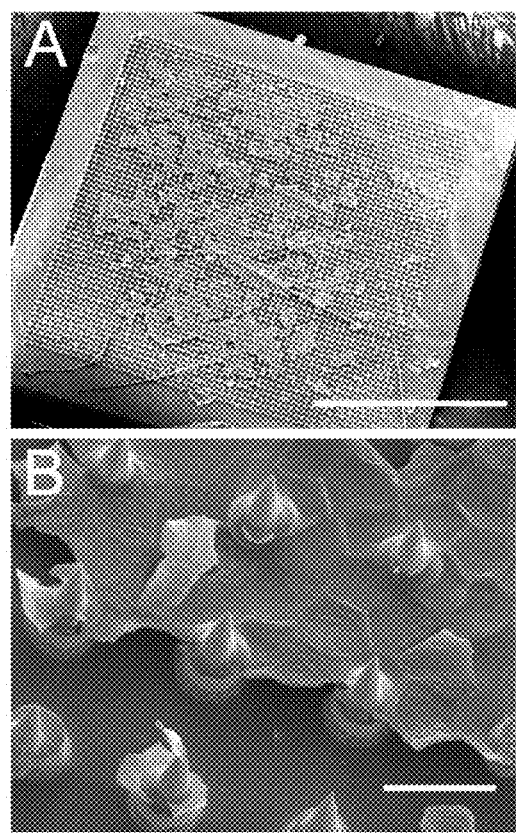
FIG. 21 shows example SEM images of a patch after application to mouse ear skin.

The quasi-static variation in mechanical strength of skin from literature is shown on FIG. 19A highlighting the changes with depth. This is determined to be a factor at lower application velocities shown in FIG. 20 where there are a number of projections being restrained at this point—indicated by a peak on the histogram around the VE-dermis junction, around 17 μm. If the velocity is increased beyond 1.22 m/s this change in property does not cause the projections to stop completely at the boundary. The benefit of this behaviour is that it may be exploited to accurately position projections in the VE, which is useful in vaccination.

The coating release into skin data have shown that there is a dramatic increase in the volume of antigen that can be delivered by exploiting the skin's mechanical properties, and application parameters. FIGS. 22A and 22B and Table 2 show that antigen delivery ranged from ~0 to ~0.75 μg per patch depending on application method. Application of patches to the skin resulted in payload being deposited within the skin, on the surface of the skin or remaining on the patch. FIGS. 22A and 22B also show that the majority of payload remains on the patch after application, with the delivery percentage variable dependant on velocity of patch application. From 1.22 m/s to 1.96 m/s there is a clear drop in the payload remaining on the patch, with an increase in that on the skin surface. This indicates at this point that the skin is deflecting round the projections and contacting the base of the patch where payload will attach to the surface. FIG. 22B shows that the increase of payload delivered within the skin is linear (R2=0.999) with velocity, mirroring the penetration data in FIGS. 19A to 19C.

Hand application of the patch gave greater delivery than application at 0.56 m/s. This is not in agreement with the penetration depth results but may be explained by the mode with which the patch is held on the ear. During hand application the patch will be constantly moved at small amplitudes around several axes which will work more payload off the projections and into the skin. This would not happen in the steady amplitude holding of the spring applicator. However, it will be appreciated that a similar effect can be achieved through the use of an oscillator, as outlined above.

Figure 26:
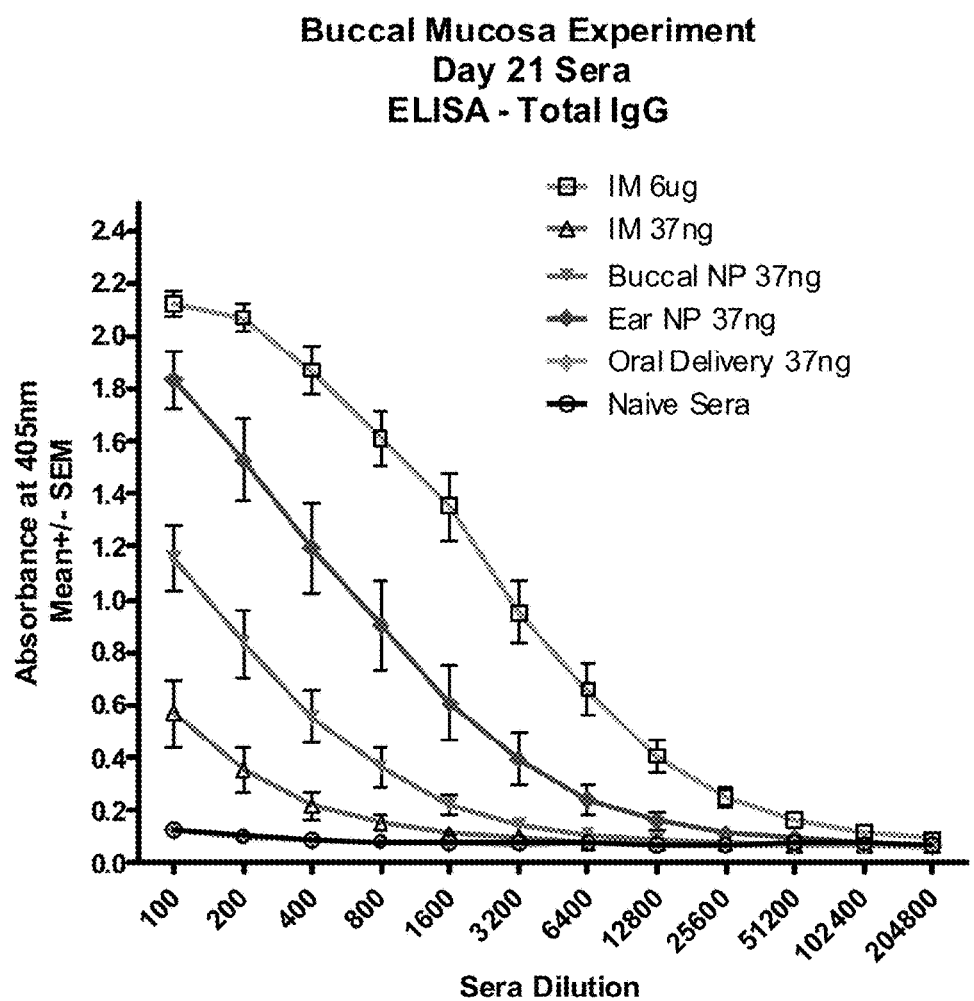

FIG. 23 shows data from the release and immune experiments combined indicating that the amount of antigen delivered can vary significantly. Although the depth of delivery is also increased as projections penetrate, their conical shapes would result in a majority of payload being deposited in the viable epidermis. Therefore velocity controlled delivery volume is assumed the dominant mechanical factor in immune total anti-OVA IgG generation. Hand application gives high standard error of mean in IgG generation which may be attributed to the sensitivity of the area of the does curve upon which it lies. This shows that apparatus for applying a patch can significantly improve the performance of the patch and reduce variations arising due to manual application.

Total anti-OVA IgG values show that the patch has generated a stronger immune response than the intramuscular injection. Previous studies use OVA protein as an antigen but boost to get required antibody levels. These data show that there is not a requirement for this boost. The design of the patch is capable of delivering selectively to a high percentage of epidermal langerhans cells and dermal dendritic cells which may account for this increased efficiency.

Using the dermis or projection geometry to arrest the movement of projections into the skin, the VE may be presented with a large surface area of vaccine, significantly increasing performance. The presence of the VE-Dermis mechanical discontinuity has great potential for targeting in this area. Importantly, if the dermis is the required target site, or a combination of both, then velocity and geometry may be modified to overcome this "barrier".

Further experiments were performed to assess the effectiveness of the applicator and patch to elicit an immunological response.

In one experiment, patches were applied to mouse and pig ear skin to assess the ability of the applicator and patch to deliver Fluvax. The patches applied were 4×4 mm patches having 110 μm long projections coated as described in the examples above with C14 labelled radioactive Ovalbumin mixed with Fluvax 2010. The patches were applied using the applicator of FIGS. 14A to 14C, with the applicator being released so that the patch impinged upon the ear at a velocity of approximately 1-2 m/s. The patches were retained in position for 2 minutes with a mean holding force of 1.9 N (+/−8% SD). Bleed was 14 days after immunisation.

The percentage of volume of material coated on the array that is delivered into the skin was then quantified for both fresh mouse skin and pre-frozen pig skin, with the results being shown in FIG. 25A. This shows successful delivery, and highlights the consistency of the delivery ability when the skin is consistent as in the case of mouse ear skin.

The immune response (1:200 dilution) generated for Fluvax 2010 when a coated patch is applied to each ear of a mouse (5 mice used) as compared to a positive control of 6 μg Fluvax IM vaccinated mice and a negative control using Naïve serum was then determined. A total of 506 ng was coated per patch, which gives a delivery per patch of around 71 ng. FIG. 25B shows the immune response at 1:100 sera dilution, whilst full dilution curves are shown in FIG. 25C. These highlight that a similar immunological response is achieved using the patch and applicator as compared to the positive control, despite an approximately 40 fold reduction in vaccine used.

In another experiment, vaccine is delivered to the buccal mucosal surface of a mouse cheek using the patch and applicator, to generate an immunological response. Again, the patches applied were 4×4 mm patches having 110 μm long projections coated as described in the examples above with C14 labelled radioactive Ovalbumin mixed with Fluvax 2010. The patches were applied using the applicator of FIGS. 14A to 14C, with the applicator clip being applied quasi-statically as there is very little space in the mouth to fit the patch. The patches were retained in position for 2 minutes with a mean holding force of 1.9 N (+/−8% SD). Bleed was 21 days after immunisation.

Delivery to the mucosal surface of the mouse cheek was measured as detailed above to be 19.6%+/−4.9% (standard deviation). This delivery includes the amount of vaccine delivered on the surface of the mucosa due to difficulty removing surface antigen due to the small mouse mouth area.

The results were compared with a number of controls, including a positive intramuscular control with very high dose, a standard spring applicator delivery to the ear, delivering vaccine intramuscularly by needle and syringe with the same dose as the patch, with full dilution curves are shown in FIG. 26. This highlights that the immune response from clip applicator to the cheek is better than that delivered by traditional IM injection.

Whilst the results shown detail quasi-static application, it will be appreciated that this was due to the use of a prototype device and the limited space available in the mouse mouth, and that in practice dynamic application could also be used for delivery to the buccul mucosa. For example, in humans, there is additional space within the mouth, making dynamic delivery feasible, whilst in animals such as mice or the like, this could be achieved with refinement of the applicator and/or patch design, for example through use of a reduced size patch. As dynamic application can assist with projection penetration, it will therefore be appreciated that further improved results would be expected with dynamic, as opposed to quasi-static application. Accordingly, the experiments demonstrate mechanically and biologically that by both design and application of patches, their performance can be significantly enhanced, and in particular can be used to enable the skin properties to be used to precisely position projections within the skin.

In particular, a velocity in the range 1.22 to 2.54 m/s can increase the depth to which 65 µm long projections may deliver antigen, increasing this from 16.5 µm to at least 32.5 µm. The viable epidermis to dermis mechanical strength change and the projection geometry can also be used for precise placement of projections in the skin. This change in depth of antigen delivery as velocity is increased allows a significant increase in ovalbumin antigen delivery, which in turn results in a strong immune response. Accordingly, the above described apparatus can help provide precise targeting through selection of appropriate application parameters and projection geometry selected based on the skin mechanical properties.

Accordingly, it will be appreciated that the above described arrangements provide apparatus for applying patches to a subject. The apparatus generally includes two jaws that may be biased open or closed. The jaws can be moved to an engaging position so that the jaws engage the subject, thereby allowing a patch to be applied. The patch may be mounted to one of the jaws so that the patch is applied as the jaws engage the subject, or may alternatively, be provided on a separate support, such as an arm, allowing the patch to be applied independently of the jaws.

In the event that the patch is mounted to jaws that are biased closed, the biasing can be used to control application parameter, such as the application force and/or velocity, thereby providing consistency of application. In the event that the patch is mounted to a biased open jaw, then a manually applied force can be used to urge the patch against the subject. However, this is not essential, and a separate device may be used to apply a force to close the jaws, thereby ensuring consistency of patch application.

The above described apparatus is simple and cheap to manufacture. In particular, in some examples, the apparatus may be a single piece of flexible metal, plastic, composite or polymer material. This makes the apparatus suitable for use in a wide range of applications, as well as allowing the device to be manufactured as a disposable device, thereby reducing concerns regarding the need to clean and/or sterilise equipment to be used on multiple subjects. However, the use of a disposable device is not essential, and the apparatus can instead be re-used with patches being fitted to the apparatus as required. In this instance, this can be achieved using a range of techniques, such as releasable adhesives, friction or interference fits, or the like. In one example, this can involve the use of replaceable cartridges for the patches.

The apparatus is easy to use, thereby allowing untrained operators to successfully apply patches, which is useful in environments where access to health professionals is limited, for example in remote regions. The apparatus is also compact, thereby allowing the apparatus to be easily transported, thereby further assisting in distribution of the apparatus.

The apparatus can be used to apply one or more patches. Furthermore, whilst the patches described above typically use a number of projections typically having a length of the order of 10 to 200 µm, this is not essential, and the apparatus can be used with any configuration of patch that is adapted to be applied to a subject. This can include patches having varying number of projections from one upwards, as well as including projections having lengths outside the ranges specified.

The small size of the apparatus allows patches to be applied to a range of suitable tissue sites, such as the ear lobes, webbing between fingers, other soft sites, folds of tissue, the inside of the cheek, or the like. This is in contrast to prior art applicators, which are typically of a large size and therefore prevent patches being applied to parts of the subject, such as the cheek, where access is limited.

The apparatus can be used to retain the patch in position after deployment. This can be useful in ensuring material is delivered to, or retrieved from a subject. However, this is not essential, and alternatively the patch may be held in position after deployment, for example through the use of an adhesive backing or the like.

Additionally, by using the apparatus with jaws biased towards the engaging position, this can help reduce the occurrence of patch bounce, where the patch effectively bounces under action of the skins natural resilience, which can in turn result in poor deployment of the patch.

In some example, the apparatus can be used to pre-tension the skin prior to patch application. This can be achieved by using a jaw having an aperture, which is urged against the subject's skin to thereby create tension. The patch is then applied aligned with the aperture, thereby ensuring the patch is applied against the tensioned skin, which in turn can assist with ensuring adequate penetration of the skin by the projections.

The apparatus can be configured to allow variety of application velocities and/or forces to be achieved, for example by providing different spring tensions.

The apparatus can be used not only in delivering material to a subject, but also for analyte detection and retrieval of material from a subject. In one example, the apparatus can include a well allow material to be stored for delivery, or to be stored post removal from the subject.

Whilst the above described examples focus on one particular example patch, it will be appreciated that the apparatus could be used with a wide range of patches, and that the example patches described with respect to FIGS. 1A to 1F are for the purpose of example only. In particular, it is possible to use the apparatus with prior art patches, including patches having longer and less densely spaced projections, including patches having 100 projections/$cm^2$ or less.

A number of further variations and options for use with the above described devices will now be described.

Herein, the terms "projection", "micro-nanoprojection", "nanoneedle", "nanoprojection", "microprojection", "needle", "microneedle", "rod" etc are used interchangeably to describe the projections.

A further feature is that the projections may be used for delivery not only through the skin but through other body surfaces, including mucosal surfaces, to cellular sites below the outer layer or layers of such surfaces. The apparatus can therefore also be used with "internal sites", below the outer layer(s) of skin and other tissues for which the devices of the present invention are to be used.

The device is suitable for intracellular delivery. The device is suitable for delivery to specific organelles within cells. Examples of organelles to which the device can be applied include a cell nucleus, or endoplasmic reticulum, for example.

In one example the device is provided having a needle support section, that is to say the projections comprise a suitable support section, of sufficient length to reach the desired site and a (needle) delivery end section having a length no greater than 20 microns and a maximum width no greater than 5 microns, preferably no greater than 2 microns.

In one example, the maximum width of the delivery end section is no greater than 1000 nm, even more preferably the maximum width of the delivery end section is no greater than 500 nm.

In a further example, the device is for mucosal delivery. This device may have a needle support section, that is to say the projections comprise a suitable support section, of sufficient length to reach the desired site, such as of length at least 100 microns and a (needle) delivery end section having a length no greater than 20 microns and a maximum width no greater than 5 microns, preferably no greater than 2 microns.

In one example, the device of the invention is for delivery to lung, eye, cornea, sclera or other internal organ or tissue. In a further example, the device is for in-vitro delivery to tissue, cell cultures, cell lines, organs, artificial tissues and tissue engineered products. This device typically has a needle support section, that is to say the projections comprise a suitable support section, of length at least 5 microns and a needle delivery end section having a length no greater than 20 microns and a maximum width no greater than 5 microns, preferably no greater than 2 microns.

In one example, the device comprises projections in which the (needle) delivery end section and support length, that is to say the "needle support section", contain a bioactive material across the whole or part of its length. The (needle) delivery end section and support length may be layered so that they contain material in selective areas thereof. This may depend upon the bioactive material being used or the target selected for example.

In a further example, a bioactive material is releasably incorporated into the material of which the needle, or projection, is composed. All, or part of the projection may be constructed of a biocompatible, biodegradable polymer (such as Poly Lactic Acid (PLA), PolyGlycolic Acid (PGA) or PGLA or Poly Glucleic Acid), which is formulated with the bioactive material of choice. The projections may then be inserted into the appropriate target site and, as they dissolve, the bioactive material will enter the organelle(s)/cells.

Examples of bioactive materials, which are not intended to be limiting with respect to the invention include polynucleotides and nucleic acid or protein molecules, antigens, allergens, adjuvants, molecules, elements or compounds. In addition, the device may contain materials such as biosensors, nanosensors or MEMS.

Illustrative material that can be delivered may include any or more of: small chemical or biochemical compounds including drugs, metabolites, amino acids, sugars, lipids, saponins, and hormones; macromolecules such as complex carbohydrates, phospholipids, peptides, polypeptides, peptidomimetics, and nucleic acids; or other organic (carbon containing) or inorganic molecules; and particulate matter including whole cells, bacteria, viruses, virus-like particles, cell membranes, dendrimers and liposomes.

The material can be selected from nucleic acids, illustrative examples of which include DNA, RNA, sense oligonucleotides, antisense oligonucleotides, ribozymes, small interfering oligonucleotides (siRNAs), micro RNAs (miRNAs), repeat associated RNAs (rasiRNA), effector RNAs (eRNAs), and any other oligonucleotides known in the art, which inhibit transcription and/or translation of a mutated or other detrimental protein. In illustrative examples of this type, the nucleic acid is in the form of an expression vector from which a polynucleotide of interest is expressible. The polynucleotide of interest may encode a polypeptide or an effector nucleic acid molecule such as sense or antisense oligonucleotides, siRNAs, miRNAs and eRNAs.

The material can be selected from peptides or polypeptides, illustrative examples of which include insulin, proinsulin, follicle stimulating hormone, insulin like growth factor-1, insulin like growth factor-2, platelet derived growth factor, epidermal growth factor, fibroblast growth factors, nerve growth factor, colony stimulating factors, transforming growth factors, tumor necrosis factor, calcitonin, parathyroid hormone, growth hormone, bone morphogenic protein, erythropoietin, hemopoietic growth factors, luteinizing hormone, glucagon, glucagon like peptide-1, anti-angiogenic proteins, clotting factors, anti-clotting factors, atrial natriuretic factor, plasminogen activators, bombesin, thrombin, enkephalinase, vascular endothelial growth factor, interleukins, viral antigens, non-viral antigens, transport proteins, and antibodies.

The material can be selected from receptor ligands. Illustrative examples of receptors include Fc receptor, heparin sulfate receptor, vitronectin receptor, Vcam-1 receptor, hemaglutinin receptor, Pvr receptor, Icam-1 receptor, decay-accelerating protein (CD55) receptor, Car (coxsackievirus-adenovirus) receptor, integrin receptor, sialic acid receptor, HAVCr-1 receptor, low-density lipoprotein receptor, BGP (biliary glycoprotein) receptor, aminopeptidase N receptor, MHC class-1 receptor, laminin receptor, nicotinic acetylcholine receptor, CD56 receptor, nerve growth factor receptor, CD46 receptor, asialoglycoprotein receptor Gp-2, alpha-dystroglycan receptor, galactosylceramide receptor, Cxcr4 receptor, Glvr1 receptor, Ram-1 receptor, Cat receptor, Tva receptor, BLVRcp1 receptor, MHC class-2 receptor, toll-like receptors (such as TLR-1 to -6) and complement receptors.

The material can be selected from antigens including endogenous antigens produced by a host that is the subject of the stimulus or material delivery or exogenous antigens that are foreign to that host. The antigens may be in the form of soluble peptides or polypeptides or polynucleotides from which an expression product (e.g., protein or RNA) is producible.

Suitable endogenous antigens include, but are not restricted to, cancer or tumor antigens. Non-limiting examples of cancer or tumor antigens include antigens from a cancer or tumor selected from ABL1 proto-oncogene, AIDS related cancers, acoustic neuroma, acute lymphocytic leukemia, acute myeloid leukemia, adenocystic carcinoma, adrenocortical cancer, agnogenic myeloid metaplasia, alopecia, alveolar soft-part sarcoma, anal cancer, angiosarcoma, aplastic anemia, astrocytoma, ataxia-telangiectasia, basal cell carcinoma (skin), bladder cancer, bone cancers, bowel cancer, brain stem glioma, brain and CNS tumors, breast cancer, CNS tumors, carcinoid tumors, cervical cancer, childhood brain tumors, childhood cancer, childhood leukemia, childhood soft tissue sarcoma, chondrosarcoma, choriocarcinoma, chronic lymphocytic leukemia, chronic myeloid leukemia, colorectal cancers, cutaneous T-cell lymphoma, dermatofibrosarcoma protuberans, desmoplastic small round cell tumor, ductal carcinoma, endocrine cancers, endometrial cancer, ependymoma, oesophageal cancer, Ewing's Sarcoma, Extra-Hepatic Bile Duct Cancer, Eye Cancer, Eye: Melanoma, Retinoblastoma, Fallopian Tube cancer, Fanconi anemia, fibrosarcoma, gall bladder cancer, gastric cancer, gastrointestinal cancers, gastrointestinal-carcinoid-tumor, genitourinary cancers, germ cell tumors, gestational-trophoblastic-disease, glioma, gynecological cancers, haematological malignancies, hairy cell leukemia, head and neck cancer, hepatocellular cancer, hereditary breast cancer, histiocytosis, Hodgkin's disease, human papillomavirus, hydatidiform mole, hypercalcemia, hypopharynx cancer, intraocular melanoma, islet cell cancer, Kaposi's sarcoma, kidney cancer, Langerhan's cell histiocytosis, laryngeal cancer, leiomyosarcoma, leukemia, Li-Fraumeni syndrome, lip cancer, liposarcoma, liver cancer, lung cancer, lymphedema, lymphoma, Hodgkin's lymphoma, non-Hodgkin's lymphoma, male breast cancer, malignant-rhabdoid tumor of kidney, medulloblastoma, melanoma, Merkel cell cancer, mesothelioma, metastatic cancer, mouth cancer, multiple endocrine neoplasia, mycosis fungoides, myelodysplastic syndromes, myeloma, myeloproliferative disorders, nasal cancer, nasopharyngeal cancer, nephroblastoma, neuroblastoma, neurofibromatosis, Nijmegen breakage syndrome, non-melanoma skin cancer, non-small-cell-lung-cancer (NSCLC), ocular cancers, esophageal cancer, oral cavity cancer, oropharynx cancer, osteosarcoma, ostomy ovarian cancer, pancreas cancer, paranasal cancer, parathyroid cancer, parotid gland cancer, penile cancer, peripheral-neuroectodermal tumours, pituitary cancer, polycythemia vera, prostate cancer, rare cancers and associated disorders, renal cell carcinoma, retinoblastoma, rhabdomyosarcoma, Rothmund-Thomson syndrome, salivary gland cancer, sarcoma, schwannoma, Sezary syndrome, skin cancer, small cell lung cancer (SCLC), small intestine cancer, soft tissue sarcoma, spinal cord tumors, squamous-cell-carcinoma-(skin), stomach cancer, synovial sarcoma, testicular cancer, thymus cancer, thyroid cancer, transitional-cell-cancer-(bladder), transitional-cell-cancer-(renal-pelvis-/-ureter), trophoblastic cancer, urethral cancer, urinary system cancer, uroplakins, uterine sarcoma, uterus cancer, vaginal cancer, vulva cancer, Waldenstrom's macroglobulinemia, Wilms' tumor. In certain examples, the cancer or tumor relates to melanoma. Illustrative examples of melanoma-related antigens include melanocyte differentiation antigen (e.g., gp100, MART, Melan-A/MART-1, TRP-1, Tyros, TRP2, MC1R, MUC1F, MUC1R or a combination thereof) and melanoma-specific antigens (e.g., BAGE, GAGE-1, gp100In4, MAGE-1 (e.g., GenBank Accession No. X54156 and AA494311), MAGE-3, MAGE4, PRAME, TRP21N2, NYNSO1a, NYNSO1b, LAGE1, p97 melanoma antigen (e.g., GenBank Accession No. M12154) p5 protein, gp75, oncofetal antigen, GM2 and GD2 gangliosides, cdc27, p21ras, gp100$^{Pmel117}$ or a combination thereof. Other tumour-specific antigens include, but are not limited to: etv6, aml1, cyclophilin b (acute lymphoblastic leukemia); Ig-idiotype (B cell lymphoma); E-cadherin, α-catenin, β-catenin, γ-catenin, p120ctn (glioma); p21ras (bladder cancer); p21ras (biliary cancer); MUC family, HER2/neu, c-erbB-2 (breast cancer); p53, p21ras (cervical carcinoma); p21ras, HER2/neu, c-erbB-2, MUC family, Cripto-1protein, Pim-1 protein (colon carcinoma); Colorectal associated antigen (CRC)-CO17-1A/GA733, APC (colorectal cancer); carcinoembryonic antigen (CEA) (colorectal cancer; choriocarcinoma); cyclophilin b (epithelial cell cancer); HER2/neu, c-erbB-2, ga733 glycoprotein (gastric cancer); α-fetoprotein (hepatocellular cancer); Imp-1, EBNA-1 (Hodgkin's lymphoma); CEA, MAGE-3, NY-ESO-1 (lung cancer); cyclophilin b (lymphoid cell-derived leukemia); MUC family, p21ras (myeloma); HER2/neu, c-erbB-2 (non-small cell lung carcinoma); Imp-1, EBNA-1 (nasopharyngeal cancer); MUC family, HER2/neu, c-erbB-2, MAGE-A4, NY-ESO-1 (ovarian cancer); Prostate Specific Antigen (PSA) and its antigenic epitopes PSA-1, PSA-2, and PSA-3, PSMA, HER2/neu, c-erbB-2, ga733 glycoprotein (prostate cancer); HER2/neu, c-erbB-2 (renal cancer); viral products such as human papillomavirus proteins (squamous cell cancers of the cervix and esophagus); NY-ESO-1 (testicular cancer); and HTLV-1 epitopes (T cell leukemia).

Foreign antigens are suitably selected from transplantation antigens, allergens as well as antigens from pathogenic organisms. Transplantation antigens can be derived from donor cells or tissues from e.g., heart, lung, liver, pancreas, kidney, neural graft components, or from the donor antigen-presenting cells bearing MHC loaded with self antigen in the absence of exogenous antigen.

Non-limiting examples of allergens include Fel d 1 (i.e., the feline skin and salivary gland allergen of the domestic cat *Felis domesticus*, the amino acid sequence of which is disclosed International Publication WO 91/06571), Der p I, Der p II, Der fI or Der fII (i.e., the major protein allergens from the house dust mite dermatophagoides, the amino acid sequence of which is disclosed in International Publication WO 94/24281). Other allergens may be derived, for example from the following: grass, tree and weed (including ragweed) pollens; fungi and molds; foods such as fish, shellfish, crab, lobster, peanuts, nuts, wheat gluten, eggs and milk; stinging insects such as bee, wasp, and hornet and the chimomidae (non-biting midges); other insects such as the housefly, fruitfly, sheep blow fly, screw worm fly, grain weevil, silkworm, honeybee, non-biting midge larvae, bee moth larvae, mealworm, cockroach and larvae of *Tenibrio molitor* beetle; spiders and mites, including the house dust mite; allergens found in the dander, urine, saliva, blood or other bodily fluid of mammals such as cat, dog, cow, pig, sheep, horse, rabbit, rat, guinea pig, mouse and gerbil; airborne particulates in general; latex; and protein detergent additives.

The material can be pathogenic organisms such as, but are not limited to, viruses, bacteria, fungi parasites, algae and protozoa and amoebae. Illustrative viruses include viruses responsible for diseases including, but not limited to, measles, mumps, rubella, poliomyelitis, hepatitis A, B (e.g., GenBank Accession No. E02707), and C (e.g., GenBank Accession No. E06890), as well as other hepatitis viruses, influenza, adenovirus (e.g., types 4 and 7), rabies (e.g., GenBank Accession No. M34678), yellow fever, Epstein-Barr virus and other herpesviruses such as papillomavirus, Ebola virus, Chikungunya virus, influenza virus, Japanese encephalitis (e.g., GenBank Accession No. E07883), dengue (e.g., GenBank Accession No. M24444), hantavirus, Sendai virus, respiratory syncytial virus, othromyxoviruses, vesicular stomatitis virus, visna virus, cytomegalovirus and human immunodeficiency virus (HIV) (e.g., GenBank Accession No. U18552). Any suitable antigen derived from such viruses are useful in the practice of the present invention. For example, illustrative retroviral antigens derived from HIV include, but are not limited to, antigens such as gene products of the gag, pol, and env genes, the Nef protein, reverse transcriptase, and other HIV components. Illustrative examples of hepatitis viral antigens include, but are not limited to, antigens such as the S, M, and L proteins of hepatitis B virus, the pre-S antigen of hepatitis B virus, and other hepatitis, e.g., hepatitis A, B, and C, viral components such as hepatitis C viral RNA. Illustrative examples of influenza viral antigens include; but are not limited to, antigens such as hemagglutinin and neuraminidase and other influenza viral components. Illustrative examples of measles viral antigens include, but are not limited to, antigens such as the measles virus fusion protein and other measles virus components. Illustrative examples of rubella viral antigens include, but are not limited to, antigens such as proteins E1 and E2 and other rubella virus components; rotaviral antigens such as VP7sc and other rotaviral components. Illustrative examples of cytomegaloviral antigens include, but are not limited to, antigens such as envelope glycoprotein B and other cytomegaloviral antigen components. Non-limiting examples of respiratory syncytial viral antigens include antigens such as the RSV fusion protein, the M2 protein and other respiratory syncytial viral antigen components. Illustrative examples of herpes simplex viral antigens include, but are not limited to, antigens such as immediate early proteins, glycoprotein D, and other herpes simplex viral antigen components. Non-limiting examples of varicella zoster viral antigens include antigens such as 9PI, gpII, and other varicella zoster viral antigen components. Non-limiting examples of Japanese encephalitis viral antigens include antigens such as proteins E, M-E, M-E-NS 1, NS 1, NS 1-NS2A, 80% E, and other Japanese encephalitis viral antigen components. Representative examples of rabies viral antigens include, but are not limited to, antigens such as rabies glycoprotein, rabies nucleoprotein and other rabies viral antigen components. Illustrative examples of papillomavirus antigens include, but are not limited to, the L1 and L2 capsid proteins as well as the E6/E7 antigens associated with cervical cancers, See Fundamental Virology, Second Edition, eds. Fields, B. N. and Knipe, D. M., 1991, Raven Press, New York, for additional examples of viral antigens.

Illustrative examples of fungi include *Acremonium* spp., *Aspergillus* spp., *Basidiobolus* spp., *Bipolaris* spp., *Blastomyces dermatidis*, *Candida* spp., *Cladophialophora carrionii*, *Coccoidiodes immitis*, *Conidiobolus* spp., *Cryptococcus* spp., *Curvularia* spp., *Epidermophyton* spp., *Exophiala jeanselmei*, *Exserohilum* spp., *Fonsecaea compacta*, *Fonsecaea pedrosoi*, *Fusarium oxysporum*, *Fusarium solani*, *Geotrichum candidum*, *Histoplasma capsulatum* var. *capsulatum*, *Histoplasma capsulatum* var. *duboisii*, *Hortaea werneckii*, *Lacazia loboi*, *Lasiodiplodia theobromae*, *Leptosphaeria senegalensis*, *Madurella grisea*, *Madurella mycetomatis*, *Malassezia furfur*, *Microsporum* spp., *Neotestudina rosatii*, *Onychocola canadensis*, *Paracoccidioides brasiliensis*, *Phialophora verrucosa*, *Piedraia hortae*, *Piedra iahortae*, *Pityriasis versicolor*, *Pseudallesheria boydii*, *Pyrenochaeta romeroi*, *Rhizopus arrhizus*, *Scopulariopsis brevicaulis*, *Scytalidium dimidiatum*, *Sporothrix schenckii*, *Trichophyton* spp., *Trichosporon* spp., *Zygomcete fungi*, *Absidia corymbifera*, *Rhizomucor pusillus* and *Rhizopus arrhizus*. Thus, representative fungal antigens that can be used in the compositions and methods of the present invention include, but are not limited to, *Candida* fungal antigen components; histoplasma fungal antigens such as heat shock protein 60 (HSP60) and other histoplasma fungal antigen components; cryptococcal fungal antigens such as capsular polysaccharides and other cryptococcal fungal antigen components; coccidiodes fungal antigens such as spherule antigens and other coccidiodes fungal antigen components; and tinea fungal antigens such as trichophytin and other coccidiodes fungal antigen components.

Illustrative examples of bacteria include bacteria that are responsible for diseases including, but not restricted to, diphtheria (e.g., *Corynebacterium* diphtheria), pertussis (e.g., *Bordetella pertussis*, GenBank Accession No. M35274), tetanus (e.g., *Clostridium tetani*, GenBank Accession No. M64353), tuberculosis (e.g., *Mycobacterium tuberculosis*), bacterial pneumonias (e.g., *Haemophilus influenzae*), cholera (e.g., *Vibrio cholerae*), anthrax (e.g., *Bacillus anthracis*), typhoid, plague, shigellosis (e.g., *Shigella dysenteriae*), botulism (e.g., *Clostridium botulinum*), salmonellosis (e.g., GenBank Accession No. L03833), peptic ulcers (e.g., *Helicobacter pylori*), Legionnaire's Disease, Lyme disease (e.g., GenBank Accession No. U59487), Other pathogenic bacteria include *Escherichia coli*, *Clostridium perfringens*, *Pseudomonas aeruginosa*, *Staphylococcus aureus* and *Streptococcus pyogenes*. Thus, bacterial antigens which can be used in the compositions and methods of the invention include, but are not limited to: pertussis bacterial antigens such as pertussis toxin, filamentous hemagglutinin, pertactin, F M2, FIM3, adenylate cyclase and other pertussis bacterial antigen components; diphtheria bacterial antigens such as diphtheria toxin or toxoid and other diphtheria bacterial antigen components; tetanus bacterial antigens such as tetanus toxin or toxoid and other tetanus bacterial antigen components, streptococcal bacterial antigens such as M proteins and other streptococcal bacterial antigen components; gram-negative bacilli bacterial antigens such as lipopolysaccharides and other gram-negative bacterial antigen components; *Mycobacterium tuberculosis* bacterial antigens such as mycolic acid, heat shock protein 65 (HSP65), the kDa major secreted protein, antigen 85A and other mycobacterial antigen components; *Helicobacter pylori* bacterial antigen components, pneumococcal bacterial antigens such as pneumolysin, pneumococcal capsular polysaccharides and other pnermiococcal bacterial antigen components; *Haemophilus influenza* bacterial antigens such as capsular polysaccharides and other *Haemophilus influenza* bacterial antigen components; anthrax bacterial antigens such as anthrax protective antigen and other anthrax bacterial antigen components; rickettsiae bacterial antigens such as rompA and other rickettsiae bacterial antigen component. Also included with the bacterial antigens described herein are any other bacterial, mycobacterial, mycoplasmal, rickettsial, or chlamydial antigens.

Illustrative examples of protozoa include protozoa that are responsible for diseases including, but not limited to, malaria (e.g., GenBank Accession No. X53832), hookworm, onchocerciasis (e.g., GenBank Accession No. M27807), schistosomiasis (e.g., GenBank Accession No. LOS 198), toxoplasmosis, trypanosomiasis, leishmaniasis, giardiasis (GenBank Accession No. M33641), amoebiasis, filariasis (e.g., GenBank Accession No. J03266), borreliosis, and trichinosis. Thus, protozoal antigens which can be used in the compositions and methods of the invention include, but are not limited to: *plasmodium falciparum* antigens such as merozoite surface antigens, sporozoite surface antigens, circumsporozoite antigens, gametocyte/gamete surface antigens, blood-stage antigen pf 155/RESA and other plasmodial antigen components; *toxoplasma* antigens such as SAG-1, p30 and other toxoplasmal antigen components; schistosomae antigens such as glutathione-S-transferase, paramyosin, and other schistosomal antigen components; *leishmania major* and other leishmaniae antigens such as gp63, lipophosphoglycan and its associated protein and other leishmanial antigen components; and *trypanosoma cruzi* antigens such as the 75-77 kDa antigen, the 56 kDa antigen and other trypanosomal antigen components.

The material can be toxin components acting as antigens. Illustrative examples of toxins include, but are not restricted to, staphylococcal enterotoxins, toxic shock syndrome toxin; retroviral antigens (e.g., antigens derived from HIV), streptococcal antigens, staphylococcal enterotoxin-A (SEA), staphylococcal enterotoxin-B (SEB), staphylococcal enterotoxin$_{1-3}$ (SE$_{1-3}$), staphylococcal enterotoxin-D (SED), staphylococcal enterotoxin-E (SEE) as well as toxins derived from mycoplasma, mycobacterium, and herpes viruses.

In specific examples, the antigen is delivered to antigen-presenting cells. Such antigen-presenting cells include professional or facultative antigen-presenting cells. Professional antigen-presenting cells function physiologically to present antigen in a form that is recognised by specific T cell receptors so as to stimulate or anergise a T lymphocyte or B lymphocyte mediated immune response. Professional antigen-presenting cells not only process and present antigens in the context of the major histocompatability complex (MHC), but also possess the additional immunoregulatory molecules required to complete T cell activation or induce a tolerogenic response. Professional antigen-presenting cells include, but are not limited to, macrophages, monocytes, B lymphocytes, cells of myeloid lineage, including monocytic-granulocytic-DC precursors, marginal zone Kupffer cells, microglia, T cells, Langerhans cells and dendritic cells including interdigitating dendritic cells and follicular dendritic cells. Non-professional or facultative antigen-presenting cells typically lack one or more of the immunoregulatory molecules required to complete T lymphocyte activation or anergy. Examples of non-professional or facultative antigen-presenting cells include, but are not limited to, activated T lymphocytes, eosinophils, keratinocytes, astrocytes, follicular cells, microglial cells, thymic cortical cells, endothelial cells, Schwann cells, retinal pigment epithelial cells, myoblasts, vascular smooth muscle cells, chondrocytes, enterocytes, thymocytes, kidney tubule cells and fibroblasts. In some examples, the antigen-presenting cell is selected from monocytes, macrophages, B lymphocytes, cells of myeloid lineage, dendritic cells or Langerhans cells. In certain advantageous examples, the antigen-presenting cell expresses CD11c and includes a dendritic cell or Langerhans cell. In some examples the antigen-presenting cell stimulates an immune response. In other examples, the antigen-presenting cell induces a tolerogenic response.

The delivery of exogenous antigen to an antigen-presenting cell can be enhanced by methods known to practitioners in the art. For example, several different strategies have been developed for delivery of exogenous antigen to the endogenous processing pathway of antigen-presenting cells, especially dendritic cells. These methods include insertion of antigen into pH-sensitive liposomes (Zhou and Huang, 1994, *Immunomethods*, 4:229-235), osmotic lysis of pinosomes after pinocytic uptake of soluble antigen (Moore et al., 1988, *Cell*, 54:777-785), coupling of antigens to potent adjuvants (Aichele et al., 1990, *J. Exp. Med.*, 171: 1815-1820; Gao et al., 1991, *J. Immunol.*, 147: 3268-3273; Schulz et al., 1991, *Proc. Natl. Acad. Sci. USA*, 88: 991-993; Kuzu et al., 1993, *Euro. J. Immunol.*, 23: 1397-1400; and Jondal et al., 1996, *Immunity* 5: 295-302) and apoptotic cell delivery of antigen (Albert et al. 1998, *Nature* 392:86-89; Albert et al. 1998, *Nature Med.* 4:1321-1324; and in International Publications WO 99/42564 and WO 01/85207). Recombinant bacteria (eg. *E. coli*) or transfected host mammalian cells may be pulsed onto dendritic cells (as particulate antigen, or apoptotic bodies respectively) for antigen delivery. Recombinant chimeric virus-like particles (VLPs) have also been used as vehicles for delivery of exogenous heterologous antigen to the MHC class I processing pathway of a dendritic cell line (Bachmann et al., 1996, *Eur. J. Immunol.*, 26(11): 2595-2600).

Alternatively, or in addition, an antigen may be linked to, or otherwise associated with, a cytolysin to enhance the transfer of the antigen into the cytosol of an antigen-presenting cell of the invention for delivery to the MHC class I pathway. Exemplary cytolysins include saponin compounds such as saponin-containing Immune Stimulating Complexes (ISCOMs) (see e.g., Cox and Coulter, 1997, *Vaccine* 15(3): 248-256 and U.S. Pat. No. 6,352,697), phospholipases (see, e.g., Camilli et al., 1991, *J. Exp. Med.* 173: 751-754), pore-forming toxins (e.g., an α-toxin), natural cytolysins of gram-positive bacteria, such as listeriolysin O (LLO, e.g., Mengaud et al., 1988, *Infect. Immun.* 56: 766-772 and Portnoy et al., 1992, *Infect. Immun.* 60: 2710-2717), streptolysin O (SLO, e.g., Palmer et al., 1998, *Biochemistry* 37(8): 2378-2383) and perfringolysin O (PFO, e.g., Rossjohn et al., *Cell* 89(5): 685-692). Where the antigen-presenting cell is phagosomal, acid activated cytolysins may be advantageously used. For example, listeriolysin exhibits greater pore-forming ability at mildly acidic pH (the pH conditions within the phagosome), thereby facilitating delivery of vacuole (including phagosome and endosome) contents to the cytoplasm (see, e.g., Portnoy et al., *Infect. Immun.* 1992, 60: 2710-2717).

The cytolysin may be provided together with a pre-selected antigen in the form of a single composition or may be provided as a separate composition, for contacting the antigen-presenting cells. In one example, the cytolysin is fused or otherwise linked to the antigen, wherein the fusion or linkage permits the delivery of the antigen to the cytosol of the target cell. In another example, the cytolysin and antigen are provided in the form of a delivery vehicle such as, but not limited to, a liposome or a microbial delivery vehicle selected from virus, bacterium, or yeast. Suitably, when the delivery vehicle is a microbial delivery vehicle, the delivery vehicle is non-virulent. In a preferred example of this type, the delivery vehicle is a non-virulent bacterium, as for example described by Portnoy et al. in U.S. Pat. No. 6,287,556, comprising a first polynucleotide encoding a non-secreted functional cytolysin operably linked to a regulatory polynucleotide which expresses the cytolysin in the bacterium, and a second polynucleotide encoding one or more pre-selected antigens. Non-secreted cytolysins may be provided by various mechanisms, e.g., absence of a functional signal sequence, a secretion incompetent microbe, such as microbes having genetic lesions (e.g., a functional signal sequence mutation), or poisoned microbes, etc. A wide variety of nonvirulent, non-pathogenic bacteria may be used; preferred microbes are relatively well characterised strains, particularly laboratory strains of *E. coli*, such as MC4100, MC1061, DH5α, etc. Other bacteria that can be engineered for the invention include well-characterised, nonvirulent, non-pathogenic strains of *Listeria monocytogenes*, *Shigella flexneri*, mycobacterium, *Salmonella*, *Bacillus subtilis*, etc. In a particular example, the bacteria are attenuated to be non-replicative, non-integrative into the host cell genome, and/or non-motile inter- or intra-cellularly.

The dissolving multi-layered projections described above can be used to deliver one or more antigens to virtually any antigen-presenting cell capable of endocytosis of the subject vehicle, including phagocytic and non-phagocytic antigen-presenting cells. In examples when the delivery vehicle is a microbe, the subject methods generally require microbial uptake by the target cell and subsequent lysis within the antigen-presenting cell vacuole (including phagosomes and endosomes).

In other examples, the antigen is produced inside the antigen-presenting cell by introduction of a suitable expression vector as for example described above. The antigen-encoding portion of the expression vector may comprise a naturally-occurring sequence or a variant thereof, which has been engineered using recombinant techniques. In one example of a variant, the codon composition of an antigen-encoding polynucleotide is modified to permit enhanced expression of the antigen in a target cell or tissue of choice using methods as set forth in detail in International Publications WO 99/02694 and WO 00/42215. Briefly, these methods are based on the observation that translational efficiencies of different codons vary between different cells or tissues and that these differences can be exploited, together with codon composition of a gene, to regulate expression of a protein in a particular cell or tissue type. Thus, for the construction of codon-optimised polynucleotides, at least one existing codon of a parent polynucleotide is replaced with a synonymous codon that has a higher translational efficiency in a target cell or tissue than the existing codon it replaces. Although it is preferable to replace all the existing codons of a parent nucleic acid molecule with synonymous codons which have that higher translational efficiency, this is not necessary because increased expression can be accomplished even with partial replacement. Suitably, the replacement step affects 5, 10, 15, 20, 25, 30%, more preferably 35, 40, 50, 60, 70% or more of the existing codons of a parent polynucleotide.

The expression vector for introduction into the antigen-presenting cell will be compatible therewith such that the antigen-encoding polynucleotide is expressible by the cell. For example, expression vectors of this type can be derived from viral DNA sequences including, but not limited to, adenovirus, adeno-associated viruses, herpes-simplex viruses and retroviruses such as B, C, and D retroviruses as well as spumaviruses and modified lentiviruses. Suitable expression vectors for transfection of animal cells are described, for example, by Wu and Ataai (2000, *Curr. Opin. Biotechnol.* 11(2):205-208), Vigna and Naldini (2000, *J. Gene Med.* 2(5):308-316), Kay, et al. (2001, *Nat. Med.* 7(1):33-40), Athanasopoulos, et al. (2000, *Int. J. Mol. Med.* 6(4):363-375) and Walther and Stein (2000, *Drugs* 60(2): 249-271).

In one aspect, the device is provided in the form of a patch containing a plurality of needles (projections) for application to a body surface. A multiplicity of projections can allow multiple cells and organelles to be targeted and provided with a material at the same time. The patch may be of any suitable shape, such as square or round for example. The overall number of projections per patch depends upon the particular application in which the device is to be used. Preferably, the patch has at least 10 needles per mm, and more preferably at least 100 needles per mm$^2$. Considerations and specific examples of such a patch are provided in more detail below.

Examples of specific manufacturing steps used to fabricate the device are described in greater detail above. In one preferred aspect, the device of the invention is constructed from biocompatible materials such as Titanium, Gold, Silver or Silicon, for example. This may be the entire device, or alternatively it may only be the projections or the delivery end section of the projections which are made from the biocompatible materials.

As used herein, the term "analyte" refers to naturally occurring and/or synthetic compounds, which are a marker of a condition (e.g., drug abuse), disease state (e.g., infectious diseases), disorder (e.g., neurological disorders), or a normal or pathologic process that occurs in a patient (e.g., drug metabolism). The term "analyte" can refer to any substance, including chemical and/or biological agents that can be measured in an analytical procedure, including nucleic acids, proteins, illicit drugs, explosives, toxins, pharmaceuticals, carcinogens, poisons, allergens, and infectious agents, which can be measured in an analytical procedure.

Analytes may be a member of a specific binding pair (sbp), with a binding partner being other member of the specific binding pair. The analyte or the binding partner may be a ligand, which is monovalent (monoepitopic) or polyvalent (polyepitopic), usually antigenic or haptenic, and is a single compound or plurality of compounds that share at least one common epitopic or determinant site. The analyte can be a part of a cell such as a bacterium or a cell bearing a blood group antigen such as A, B, D, etc., or an HLA antigen or the analyte may be a microorganism, e.g., bacterium, fungus, protozoan, or virus. In certain circumstances the analyte may be a reference compound, a control compound, a calibrator, and the like.

The monoepitopic ligand analytes will generally be from about 100 to about 2,000 molecular weight, more usually, from about 125 to about 1,000 molecular weight. Non-limiting examples of monoepitopic analytes include drugs, e.g., drugs of abuse and therapeutic drugs, metabolites, pesticides, pollutants, nucleosides, and the like. Included among drugs of interest are the alkaloids, steroids, lactams, aminoalkylbenzenes, benzheterocyclics, purines, drugs derived from marijuana, hormones, vitamins, prostaglandins, tricyclic antidepressants, anti-neoplastics, aminoglycosides, antibiotics, nucleosides and nucleotides, miscellaneous individual drugs which include methadone, meprobamate, serotonin, meperidine, lidocaine, procainamide, acetylprocainamide, propranolol, griseofulvin, valproic acid, butyrophenones, antihistamines, chloramphenicol, anticholinergic drugs, such as atropine, their metabolites and derivatives, and so forth.

Metabolites related to diseased states include spermine, galactose, phenylpyruvic acid, and porphyrin Type 1 and so forth.

Among pesticides of interest are polyhalogenated biphenyls, phosphate esters, thiophosphates, carbamates, polyhalogenated sulfenamides, their metabolites and derivatives.

The polyvalent ligand analytes will normally be poly (amino acids), e.g., polypeptides and proteins, polysaccharides, mucopolysaccharides, nucleic acids, and combinations thereof. Such combinations include components of bacteria, viruses, chromosomes, genes, mitochondria, nuclei, cell membranes and the like.

A polynucleotide or nucleic acid is a compound or composition that is a polymeric nucleotide or nucleic acid polymer, which may include modified nucleotides.

For the most part, the polyepitopic ligand analytes to which the techniques can be applied have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight; among the hormones of interest, the molecular weights will usually range from about 5,000 to 60,000 molecular weight.

A wide variety of proteins is contemplated in the above examples, including proteins having similar structural features, proteins having particular biological functions, proteins related to specific microorganisms, particularly disease causing microorganisms, etc. Such proteins include, for example, immunoglobulins, cytokines, enzymes, hormones, cancer antigens, nutritional markers, tissue specific antigens, etc. Illustrative examples of this type include protamines, histones, albumins, globulins, scleroproteins, phosphoproteins, mucoproteins, chromoproteins, lipoproteins, nucleoproteins, glycoproteins, T-cell receptors, proteoglycans, human leukocyte antigen (HLA), unclassified proteins, e.g., somatotropin, prolactin, insulin, pepsin, proteins found in human plasma, blood clotting factors, protein hormones such as, e.g., follicle-stimulating hormone, luteinizing hormone, luteotropin, prolactin, chorionic gonadotropin, tissue hormones, cytokines, cancer antigens such as, e.g., PSA, CEA, a-fetoprotein, acid phosphatase, CA19.9 and CA125, tissue specific antigens, such as, e.g., alkaline phosphatase, myoglobin, CPK-MB and calcitonin, and peptide hormones. In other embodiments, the polypeptides of interest are mucopolysaccharides and polysaccharides.

The term analytes may also include other materials identified above with respect to material delivery.

The term subject can include any living subject, such as humans, animals, or plants, and is not intended to be limiting.

Persons skilled in the art will appreciate that numerous variations and modifications will become apparent. All such variations and modifications which become apparent to persons skilled in the art, should be considered to fall within the spirit and scope that the invention broadly appearing before described.

The claims defining the invention are as follows:

1. An apparatus for applying a patch to a subject, the apparatus comprising:
    a) opposable jaws comprising a first arm and a second arm moveable between open and engaging positions, wherein in the open position the jaws can receive at least part of the subject between the jaws, and in the engaging position the jaws can engage the at least part of the subject and wherein one of the first and second arms includes an aperture;
    b) a first patch having a number of solid projections thereon with at least one of the projections being coated;
    c) a first patch support which supports the first patch, wherein the first patch support urges the first patch against the at least part of the subject so that the projections are capable of penetrating the skin of the subject, and wherein the patch is attached to the patch support;
    d) a third arm mounted to the first and second arms, the first patch support being provided on the third arm;
    e) a first biasing mechanism that urges the jaws into the engaging position thereby applying a force to a tissue surface of the subject prior to the first patch being applied; and
    f) a second biasing mechanism that urges the third arm to deliver the first patch to the subject through the aperture at predetermined application parameters and such that the first patch is retained in place for a predetermined application period.

2. The apparatus according to claim 1, wherein the aperture is for applying a force to a tissue surface of the subject prior to the patch being applied, to thereby compress the tissue.

3. The apparatus according to claim 1, wherein the apparatus further includes a fourth arm mounted to the first and second arms, a second patch support being provided on the fourth arm and a second patch supported by the second patch support.

4. The apparatus according to claim 3, wherein one of the first and second arms includes an aperture aligned with the patch support on the fourth arm so that the patch second extends through the aperture when engaging the subject, in use.

5. The apparatus according to claim 4, wherein the aperture is for applying a force to a tissue surface of the subject prior to the patch being applied, to thereby compress the tissue.

6. The apparatus according to claim 5, wherein the second biasing mechanism urges the third arm to deliver the second patch to the subject at predetermined application parameters and such that the second patch is retained in place for a predetermined application period.

7. The apparatus according to claim 4, wherein the aperture is for applying a force to a tissue surface of the subject prior to the patch being applied, to thereby stretch the tissue.

8. The apparatus according to claim 4, wherein the aperture is for applying a force to a tissue surface of the subject prior to the patch being applied, to thereby pre-stress the tissue.

9. The apparatus according to claim 1, wherein the projections have a density of at least one of:
    a) between 1,000-30,000 projections/cm$^2$;
    b) less than 1,000 projections/cm$^2$; and,
    c) less than 100 projections/cm$^2$.

10. The apparatus according to claim 1, wherein the projections have a length of at least one of:
    a) between 10 to 200 μm; and,
    b) greater than 200 μm.

11. The apparatus according to claim 10, wherein the projections have a length of 90 μm.

12. The apparatus according to claim 1, wherein the projections have a radius of curvature of at least one of:
    a) greater than 0.5 μm;
    b) greater than 1 μm; and,
    c) greater than 5 μm.

13. The apparatus according to claim 1, wherein the projections include a support section and a targeting section.

14. The apparatus according to claim 13, wherein the targeting section has a diameter of less than at least one of:
    a) 50 μm;
    b) 100 μm;
    c) 150 μm; and,
    d) 400 μm.

15. The apparatus according to claim 13, wherein a length for the targeting section is at least:
    a) less than 50 μm;
    b) less than 100 μm; and,
    c) less than 300 μm.

16. The apparatus according to claim 13, wherein a length for the support section is at least one of:
    a) for epidermal delivery <200 μm;
    b) for dermal cell delivery <1000 μm;
    c) for delivery to basal cells in the epithelium of the mucosa 600-800 μm; and,
    d) for lung delivery of the order of 100 μm.

17. The apparatus according to claim 1, wherein the projections are shaped to at least partially control a depth of penetration of the projection in use.

18. The apparatus according to claim 17, wherein the projections have a stepped configuration.

19. The apparatus according to claim 17, wherein the projections have a supporting section having a diameter greater than a diameter of a targeting section.

20. The apparatus according to claim 1, wherein the aperture is for applying a force to a tissue surface of the subject prior to the patch being applied, to thereby stretch the tissue.

21. The apparatus according to claim 1, wherein the aperture is for applying a force to a tissue surface of the subject prior to the patch being applied, to thereby pre-stress the tissue.

* * * * *